US008420839B1

(12) United States Patent
DeLuca et al.

(10) Patent No.: US 8,420,839 B1
(45) Date of Patent: Apr. 16, 2013

(54) CRYSTALLIZATION OF 1α-HYDROXY-2-METHYLENE-18,19-DINOR-HOMOPREGNACALCIFEROL

(71) Applicant: Wisconsin Alumni Research Foundation, Madison, WI (US)

(72) Inventors: Hector F. DeLuca, Deerfield, WI (US); Rafal Barycki, Madison, WI (US); James B. Thoden, Madison, WI (US); Hazel M. Holden, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/632,791

(22) Filed: Oct. 1, 2012

Related U.S. Application Data

(60) Provisional application No. 61/543,513, filed on Oct. 5, 2011.

(51) Int. Cl.
*C07C 401/00* (2006.01)
(52) U.S. Cl.
USPC ........................................................ 552/653
(58) Field of Classification Search ............... 552/653
See application file for complete search history.

(56) References Cited

U.S. PATENT DOCUMENTS

| | | | |
|---|---|---|---|
| 5,086,191 A | 2/1992 | DeLuca et al. | |
| 5,536,713 A | 7/1996 | DeLuca et al. | |
| 5,843,928 A | 12/1998 | DeLuca et al. | |
| 6,362,350 B1 * | 3/2002 | DeLuca et al. | 552/653 |
| 6,432,936 B1 * | 8/2002 | DeLuca et al. | 514/167 |
| 6,462,031 B2 * | 10/2002 | DeLuca et al. | 514/167 |
| 6,835,723 B2 * | 12/2004 | DeLuca et al. | 514/167 |
| 7,053,075 B2 * | 5/2006 | DeLuca et al. | 514/167 |
| 7,238,681 B2 | 7/2007 | DeLuca et al. | |
| 8,188,064 B2 * | 5/2012 | Clagett-Dame et al. | 514/167 |

OTHER PUBLICATIONS

Baggiolini et al., "Stereocontrolled Total Synthesis of 1[alpha],25-Dihydroxycholecaliferol and 1[alpha],25-Dihydroxyergo- calciferol", Journal of Organic Chemistry, 1986, 51: 3098-3108.
Lythgoe et al., "Calciferol and its Relatives. Part 22. A Direct Total Synthesis of Vitamin D2 and Vitamin D3", J Chem. Soc. Perkin I, 1978, 590-595.
Lythgoe, "Synthetic Approaches to Vitamin D and its Relatives", Chem. Soc. Rev., 1983, 9: 449-475.
Perlman et al., "Novel Synthesis of 19-Nor-Vitamin D Compounds", Tetrahedron Letters, 1991, 32: 7663-7666.
Sardina et al., "Studies on the Synthesis of Side-Chain Hydroxylated Metabolites of Vitamin D. 2. Stereocontrolled Synthesis of 25-Hydroxyvitamin D2", Journal of Organic Chemistry, 1986, 51: 1264-1269.
Sicinski et al., "New 1alpha,25-Dihydroxy-19-norvitannin D3 Compounds of High Biological Activity: Synthesis and Biological Evaluation of 2-Hydroxymethyl, 2-Methyl, and 2-Methylene Analogs", J. Med. Chem., 1998, 41: 4662-4674.

(Continued)

*Primary Examiner* — Sabiha N Qazi
(74) *Attorney, Agent, or Firm* — Andrus, Sceales, Starke & Sawall, LLP

(57) ABSTRACT

A method of purifying 1α-hydroxy-2-methylene-18,19-dinor-homopregnacalciferol to obtain 1α-hydroxy-2-methylene-18,19-dinor-homopregnacalciferol in crystalline form using precipitation with hexane from ethyl acetate. A method of preparing 1α-hydroxy-2-methylene-18,19-dinor-homopregnacalciferol crystals acceptable for X-ray experiment using precipitation with hexane from benzene by diffusive exchange of the solvents is also described.

12 Claims, 4 Drawing Sheets

OTHER PUBLICATIONS

Toh et al., "Studies on a Convergent Route to Side-Chain Analogues of Vitamin D:25-Hydroxy-23-oxavitamin D3", Journal of Organic Chemistry, 1983, 48: 1414-1417.

Andrews et al., "A Direct, Regio- and Stereoselective 1Alpha-Hydroxylation of (5E)-Calciferol Derivatives", Journal of Organic Chemistry, 1986, 51: 1635-1637.

Calverley et al., "A Biologically Active Vitamin D Metabolite Analogue", Tetrahedron, 1987, 43(20): 4609-4619.

Choudhry et al., "Synthesis of a Biologically Active Vitamin-D2 Metabolite", Journal of Organic Chemistry, 1993, 58:1496-1500.

Nerinckx et al., "An Improved Synthesis of 1Alpha-Hydroxy Vitamin D3", Tetrahedron, 1991, 47(45): 9419-9430.

Paaren et al., "Direct C(1) Hydroxylation of Vitamin D3 and Related Compounds", Journal of Organic Chemistry, 1980, 45: 3253-3258.

Paaren et al., "Direct C(1) Hydroxylation of Vitamin D Compounds: Convenient Preparation of 1Alpha-Hydroxyvitamin D3, aAlpha,25-Dihydroxyvitamin D3, and 1Alpha-Hydroxyvitamin D2", Proc. Natl. Acad. Sci. USA, 1978, 75(5): 2080-2081.

Vanmaele et al., "An Efficient Synthesis of 1Alpha-25-Dihydroxy Vitamin D3", Tetrahedron, 1985, 41(1): 141-144.

Vanmaele et al., "1Alpha-Hydroxy Previtamin D3 and its Selective Formation From 1-Keto Previtamin D3", Tetrahedron, 1984, 40(7): 1179-1182.

Vanmaele et al., "A Stereocontrolled Partial Synthesis of 1Alpha-Hydroxy Vitamin D3", Tetrahedron Letters, 1982, 23 (9): 995-998.

\* cited by examiner

CRYSTALLIZATION OF 1α-HYDROXY-2-METHYLENE-18,19-DINOR-HOMOPREGNACALCIFEROL

STATEMENT REGARDING FEDERALLY SPONSORED RESEARCH OR DEVELOPMENT

This invention was made with government support under DK047814 awarded by the National Institutes of Health. The government has certain rights in the invention.

BACKGROUND OF THE INVENTION

The present invention relates to purification of organic compounds, and more particularly to the purification of 1α-hydroxy-2-methylene-18,19-dinor-homopregnacalciferol (referred to herein as "051810") by preparing it in crystalline form.

Purification of organic compounds, especially those designated for pharmaceutical use, is of considerable importance for chemists synthesizing such compounds. Preparation of the compound usually requires many synthetic steps and, therefore, the final product can be contaminated not only with side-products derived from the last synthetic step of the procedure but also with compounds that were formed in previous steps. Even chromatographic purification, which is a very efficient but relatively time-consuming process, does not usually provide compounds which are sufficiently pure to be used as drugs.

Depending on the method used to synthesize 1α-hydroxyvitamin D compounds, different minor undesirable compounds can accompany the final product. Thus, for example, if direct C-1 hydroxylation of 5,6-trans geometric isomer of vitamin D is performed, followed by $SeO_2$/NMO oxidation and photochemical irradiation [see Andrews et al., *J. Org. Chem.* 51, 1635 (1986); Calverley et al., *Tetrahedron* 43, 4609 (1987); Choudry et al, *J. Org. Chem.* 58, 1496 (1993)], the final 1α-hydroxyvitamin D product can be contaminated with 1β-hydroxy- as well as 5,6-trans isomers. If the method consists of C-1 allylic oxidation of the 4-phenyl-1,2,4-triazoline-3,5-dione adduct of the previtamin D compound, followed by cycloreversion of the modified adduct under basic conditions [Nevinćkx et al., *Tetrahedron* 47, 9419 (1991); Vanmaele et al, *Tetrahedron* 41, 141 (1985) and 40, 1179 (1994); Vanmaele et al., *Tetrahedron Lett.* 23. 995 (1982)], one can expect that the desired 1α-hydroxyvitamin can be contaminated with the previtamin 5(10), 6,8-triene and 1β-hydroxy isomer. One of the most useful C-1 hydroxylation methods, of very broad scope and numerous applications, is the experimentally simple procedure elaborated by Paaren et al. [see *J. Org. Chem.* 45, 3253 (1980) and *Proc. Natl. Acad. Sci. U.S.A.* 75, 2080 (1978)]. This method consists of allylic oxidation of 3,5-cyclovitamin D derivatives, readily obtained from the buffered solvolysis of vitamin D tosylates, with $SeO_2$/t-BuOOH and subsequent acid-catalyzed cycloreversion to the desired 1α-hydroxy compounds. Taking into account this synthetic path it is reasonable to assume that the final product can be contaminated with 1α-hydroxy epimer, 5,6-trans isomer and the previtamin D form. 1α-hydroxyvitamin $D_4$ is another undesirable contaminant found in 1α-hydroxyvitamin D compounds synthesized from vitamin $D_2$ or from ergosterol. 1α-hydroxyvitamin $D_4$ results from C-1 oxidation of vitamin $D_4$, which in turn is derived from contamination of the commercial ergosterol material. Typically, the final product may contain up to about 1.5% by weight 1α-hydroxyvitamin $D_4$. Thus, a purification technique that would eliminate or substantially reduce the amount of 1α-hydroxyvitamin $D_4$ in the final product to less than about 0.1-0.2% would be highly desirable.

The vitamin D conjugated triene system is not only heat- and light-sensitive but it is also prone to oxidation, leading to the complex mixture of very polar compounds. Oxidation usually happens when a vitamin D compound has been stored for a prolonged time. Other types of processes that can lead to a partial decomposition of vitamin D compounds consist of some water-elimination reactions; their driving force is allylic (1α-) and homoallylic (3β-) position of the hydroxy groups. The presence of such above-mentioned oxidation and elimination products can be easily detected by thin-layer chromatography.

Usually, all 1α-hydroxylation procedures require at least one chromatographic purification. However, even chromatographically purified 1α-hydroxyvitamin D compounds, although showing consistent spectroscopic data, suggesting homogeneity, do not meet the purity criteria required for therapeutic agents that can be orally, parenterally or transdermally administered. Therefore, it was evident that a suitable method of purification of the 1α-hydroxylated vitamin D compound 051810 is required.

SUMMARY OF THE INVENTION

The present invention relates to a method of purifying 051810 by means of crystallization to obtain 051810 in crystalline form. The solvent plays a crucial role in the crystallization process, and is typically an individual liquid substance or a suitable mixture of different liquids. For crystallizing 051810, the most appropriate solvent and/or solvent system is characterized by the following factors:

(1) low toxicity;
(2) low boiling point;
(3) significant dependence of solubility properties with regard to temperature (condition necessary for providing satisfactory crystallization yield); and
(4) relatively low cost.

Interestingly, hexane, so frequently used for crystallization purposes, was found less suitable as the sole solvent for crystallization of 051810. However, it was found that a mixture of ethyl acetate and hexane, was most useful for the crystallization of 051810. In particular, it was determined that a mixture of about 1% ethyl acetate with about 99% hexane (by volume) performed well. The ethyl acetate/hexane solvent mixture was also easy to remove by evaporation or other well known methods. In all cases the crystallization process occurred easily and efficiently; and the precipitated crystals were sufficiently large to assure their recovery by filtration or other means.

Accordingly, there is obtained 1α-hydroxy-2-methylene-18,19-dinor-homopregnacalciferol in crystalline form. The crystalline form and three dimensional structure of 1α-hydroxy-2-methylene-18,19-dinor-homopregnacalciferol has a molecular packing arrangement defined by space group P2 and unit cell dimensions a=4.8 Å, b=22.9 Å, c=36.1 Å, α=90°, β=90° and γ=90°.

In one embodiment, there is described a method of purifying 1α-hydroxy-2-methylene-18,19-dinor-homopregnacalciferol, comprising the steps of:

(a) dissolving a product containing 1α-hydroxy-2-methylene-18,19-dinor-homopregnacalciferol to be purified in a solvent comprising ethyl acetate;

(b) adding hexane to said solvent and dissolved product to form a mixture;

(c) cooling said mixture containing said dissolved product below ambient temperature for a sufficient amount of time to form a precipitate of 1α-hydroxy-2-methylene-18,19-dinor-homopregnacalciferol crystals; and (d) separating the 1α-hydroxy-2-methylene-18,19-dinor-homopregnacalciferol crystals from the mixture.

In another embodiment, there is described a method of preparing 1α-hydroxy-2-methylene-18,19-dinor-homopregnacalciferol crystals by diffusive exchange of solvents, comprising the steps of:

(a) dissolving a product containing 1α-hydroxy-2-methylene-18,19-dinor-homopregnacalciferol in a first solvent comprising benzene;

(b) providing a second solvent comprising hexane;

(c) allowing said first solvent with dissolved product and said second solvent to diffuse together for a sufficient amount of time to form a precipitate of 1α-hydroxy-2-methylene-18,19-dinor-homopregnacalciferol crystals; and (d) recovering the 1α-hydroxy-2-methylene-18,19-dinor-homopregnacalciferol crystals.

DETAILED DESCRIPTION OF THE INVENTION

Figure 1:
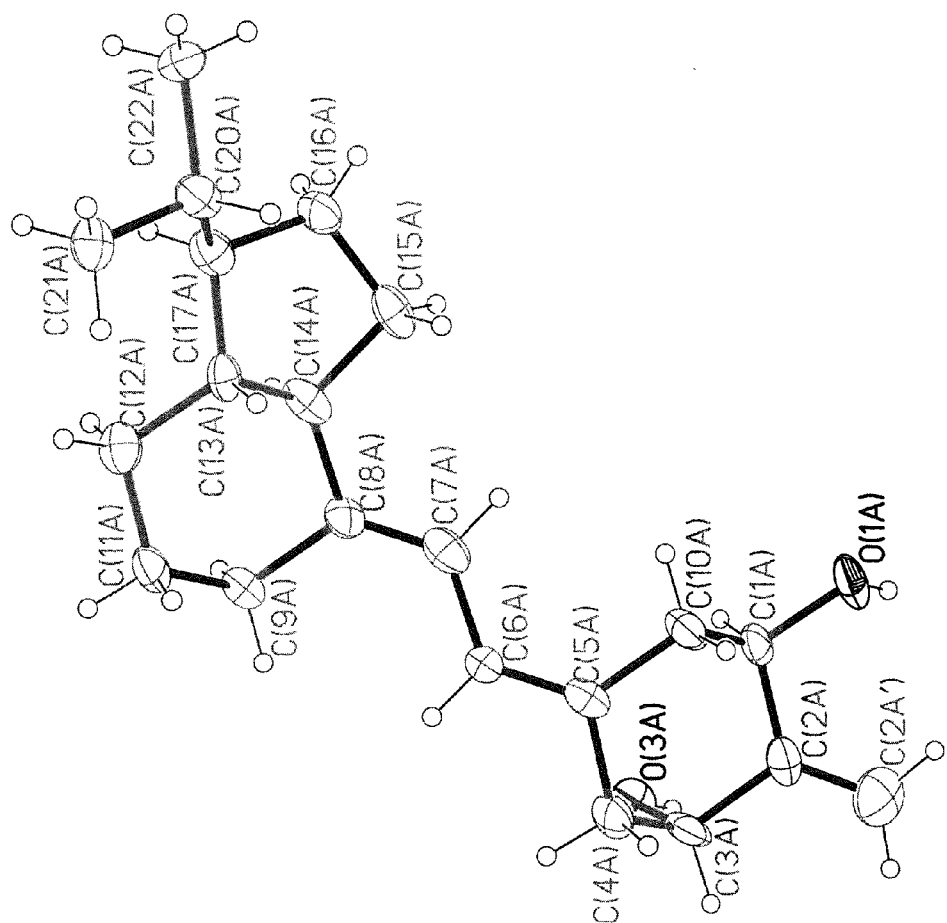
FIG. 1 is an illustration of the three dimensional structure of the first crystallographic asymmetric molecule for 051810 as defined by the atomic positional parameters discovered and set forth herein.

The present invention provides 1α-hydroxy-2-methylene-18,19-dinor-homopregnacalciferol (051810) in crystalline form, a pharmacologically important compound, characterized by the formula I shown below:

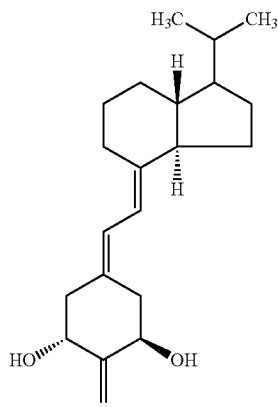

The present invention also provides a valuable method of purification of 051810. The purification technique involves obtaining the 051810 product in crystalline form by utilizing a crystallization procedure wherein the 051810 material to be purified is dissolved using ethyl acetate as the solvent and further precipitation with hexane. Preferably a ratio of ethyl acetate and hexane is about 1:99 (by volume). Thereafter, the solvent can be removed by evaporation, with or without vacuum, or other means as is well known, or the resultant crystals may be filtered from the mother liquor. The technique can be used to purify a wide range of final products containing 051810 obtained from any known synthesis thereof, and in varying concentrations, i.e. from microgram amounts to kilogram amounts. As is well known to those skilled in this art, the amount of solvent utilized should be minimized and/or adjusted according to the amount of 051810 to be purified.

The usefulness and advantages of the present crystallization procedure is shown in the following specific Example 1. After crystallization, the precipitated material was observed under a microscope to confirm its crystalline form. Yields of crystals were relatively high and the obtained crystals showed a relatively sharp melting point of 140-145° C.

The described crystallization process of the synthetic 051810 product represents a valuable purification method, which can remove most side products derived from the synthetic path. Such impurity is the result of the contamination of starting raw materials. The crystallization process occurred easily and efficiently; and the precipitated crystals were sufficiently large to assure their recovery by filtration, or other means.

Crystallization of 1α-hydroxy-2-methylene-18,19-dinor-homopregnacalciferol (051810)

EXAMPLE 1

Crystallization from Ethyl Acetate/Hexane 1.25 g of prepurified (see U.S. Pat. No. 7,238,681) crude 1α-hydroxy-2-methylene-18,19-dinor-homopregnacalciferol was dissolved in ethyl acetate (3 ml) at room temperature and hexane (300 ml) was poured into the vigorously shaken solution. The mixture was kept in a refrigerator (at 4° C.) overnight and the resulted crystals were filtered off, washed with one portion (30 ml) of cooled (4° C.) hexane and dried under reduced pressure for 3 h giving 1.10 g of a pure product.

In order to obtain crystals acceptable for the X-ray experiment, 1α-Hydroxy-2-methylene-18,19-dinor-homopregnacalciferol (12 mg) was placed in an inner tube of a vessel and dissolved in 300 µl of benzene. To an outer tube of the vessel hexane (2 ml) was poured so that a benzene to hexane ratio of about 13:87, by volume, is obtained, and the whole system was carefully purged with argon, and then maintained as a closed system. The vessel was kept tightly closed for 4 days at room temperature. Crystals were grown employing diffusive exchange of the two solvents.

A colorless rod-shaped crystal of dimensions 0.73×0.08× 0.02 mm was selected for structural analysis. Intensity data were collected using a Bruker AXS Platinum 135 CCD detector controlled with the PROTEUM software suite (Bruker AXS Inc., Madison, Wis.). The x-ray source was CuKa radiation (1.54178 Å) from a Rigaku RU200 x-ray generator equipped with Montel optics, operated at 50 kV and 90 mA. The x-ray data were processed with SAINT version 7.06A (Bruker AXS Inc.) and internally scaled with SADABS version 2005/1 (Bruker AXS Inc.). The sample was mounted on a glass fiber using vacuum grease and cooled to 100 K. The intensity data were measured as a series of phi and omega oscillation frames each of 1° for 60-120 sec/frame. The detector was operated in 1024×1024 mode and was positioned 5.0 cm from the sample. Cell parameters were determined from a non-linear least squares fit of 9999 peaks in the range of 3.0<theta<50.8°. The data were merged to form a set of 4693 independent data with R(int)=0.0884.

Figure 2A:
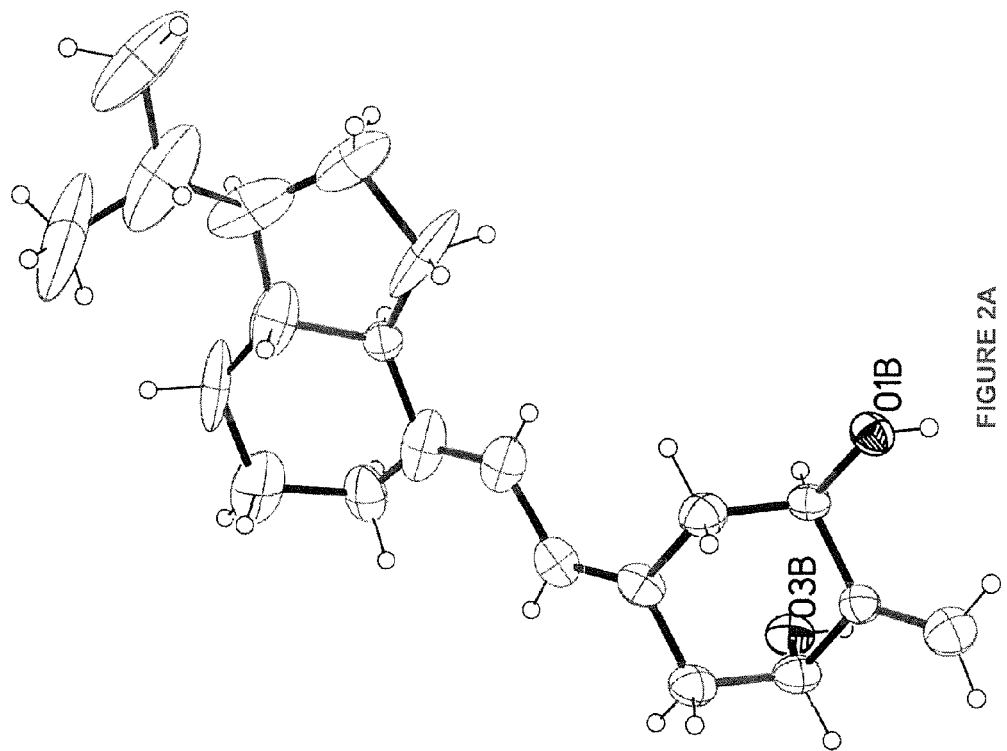
FIG. 2a is an illustration of the three dimensional structure of the second crystallographic asymmetric molecule for 051810 in the absence of the benzene molecule and as defined by the atomic positional parameters discovered and set forth herein.
Figure 2B:
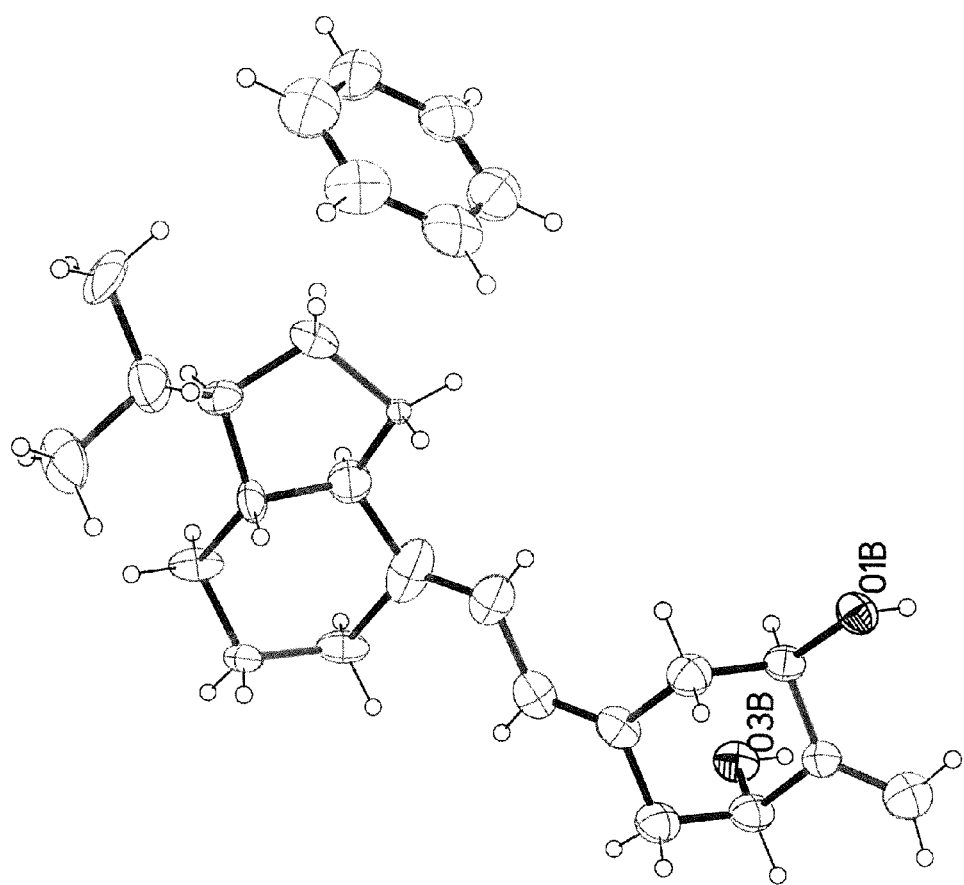
FIG. 2b is an illustration of the three dimensional structure of the second asymmetric molecule for 051810 in the presence of the benzene molecule and as defined by the atomic positional parameters discovered and set forth herein.
Figure 3:
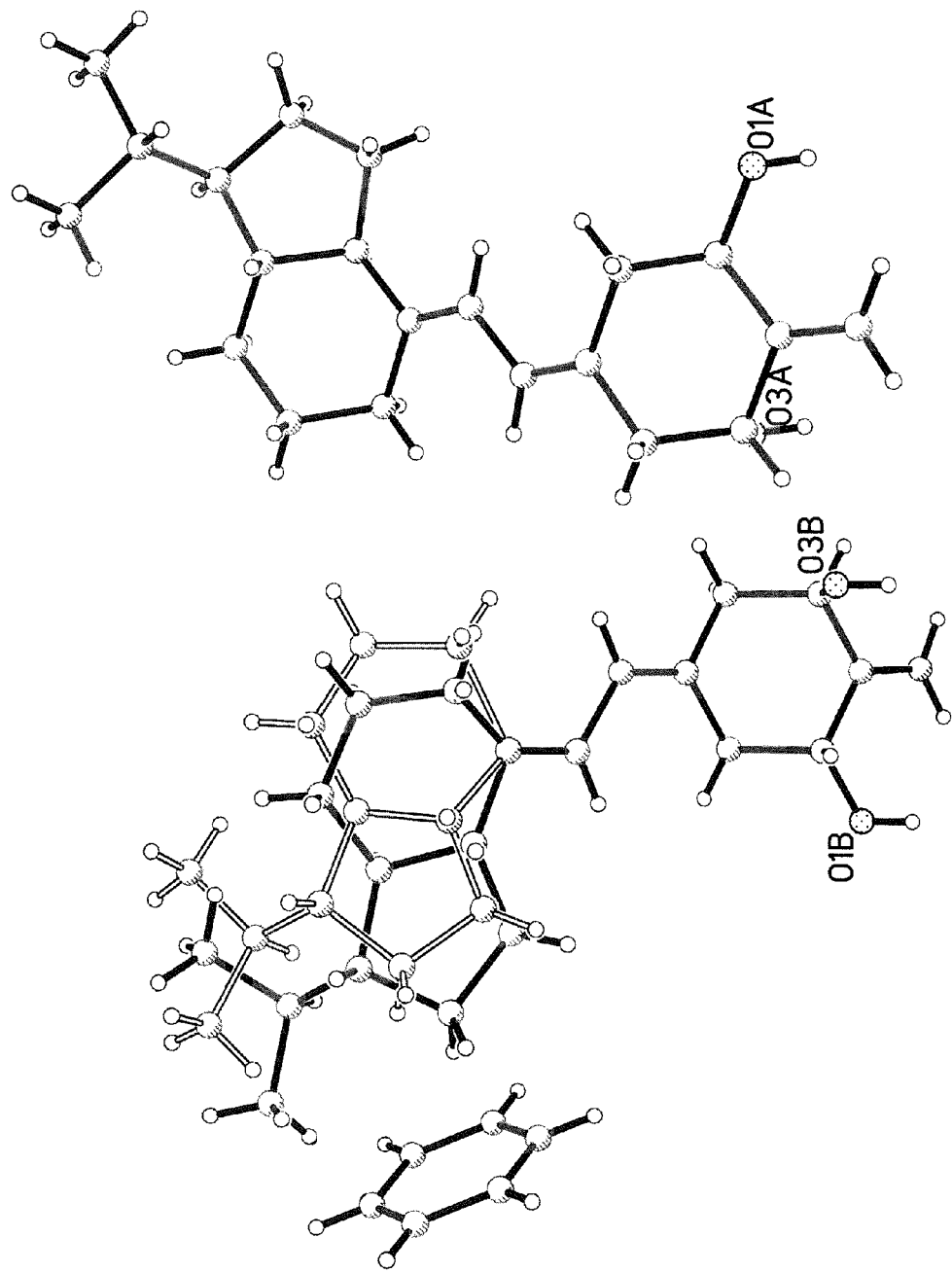
FIG. 3 is an illustration of a ball-and-stick representation of the entire asymmetric unit for 051810.

The orthorhombic space group P2(1)2(1)2(1) was determined by systematic absences and statistical tests and verified by subsequent refinement. The structure was solved by direct methods and refined by full-matrix least-squares methods on $F^2$, (a) G. M. Sheldrick (1994), SHELXTL Version 5 Reference Manual, Bruker AXS Inc.; (b) *International Tables for Crystallography, Vol. C*, Kluwer: Boston (1995). The asymmetric unit is comprised of two molecules of 051810 and a benzene molecule. Molecule "A" is shown in FIG. 1, with thermal ellipsoids drawn at the 40% probability level. Based on lattice packing, the benzene molecule could not be present at full occupancy, and refinement of its occupancy led to a value of approximately 0.5. The presence of the benzene molecule lead to a disorder in a portion of molecule "B". Refinement of the occupancies of the two disordered configurations independently of the occupancy of the benzene converged also at a value of about 0.5 for each. FIG. 2a shows molecule B in its configuration in the absence of the benzene molecule, and FIG. 2b shows its configuration in the presence of the benzene molecule; both figures are drawn with thermal ellipsoids at the 40% probability level. FIG. 3 shows a ball-and-stick representation of the entire asymmetric unit, with the hollow bonds showing the conformation in the presence of the benzene molecule. Hydrogen atom positions were refined by a riding model with idealized geometry. Non-hydrogen atoms were refined with anisotropic displacement parameters. The benzene molecule was refined with idealized geometry. A total of 559 parameters were refined against 26 restraints and 4693 data to give wR2=0.2524 and S=0.951 for weights of w=1/[s$^2$(F$^2$)+(0.1719P)$^2$], where P=[F$_o^2$+2F$_c^2$]/3. The final R(F) was 0.0910 for the 6781 observed data. The largest shift/s.u. was 0.001 in the final refinement cycle and the final difference map had maxima and minima of 0.366 and −0.305 e/Å$^3$, respectively. The absolute structure was determined by refinement of the Flack parameter, H. D. Flack, *Acta Cryst. A*, vol. 39, 876-881 (1983).

The three dimensional structure of 051810 as defined by the following physical data and atomic positional parameters described and calculated herein is illustrated in FIGS. 1, 2a, 2b and 3.

TABLE 1

Crystal data and structure refinement for 051810.

| | |
|---|---|
| Identification Code | 051810 |
| Empirical formula | C45 H67 O4 |
| Formula weight | 671.99 |
| Temperature | 100(1) K |
| Wavelength | 1.54178 Å |
| Crystal system | Orthorhombic |
| Space group | P2(1)2(1)2(1) |
| Unit cell dimensions | a = 4.8020(10) Å   α = 90° |
| | b = 22.940(5) Å    β = 90° |
| | c = 36.124(7) Å    γ = 90° |
| Volume | 3979.3(14) Å$^3$ |
| Z | 4 |
| Density (calculated) | 1.122 Mg/m$^3$ |
| Absorption coefficient | 0.533 mm$^{-1}$ |
| F(000) | 1476 |
| Crystal | 0.73 × 0.08 × 0.02 mm |
| Theta range for data collection | 2.28 to 54.17° |
| Limiting indices | −4 < h < 4, −24 < k < 23, −37 < l < 37 |
| Reflections collected | 12592 |
| Independent reflections | 4693 [R(int) = 0.0884] |
| Completeness to Theta = 54.17° | 98.2% |
| Refinement method | Full-matrix least-squares on F$^2$ |
| Data/restraints/parameters | 4693/26/559 |
| Goodness-of-fit on F$^2$ | 0.951 |

TABLE 1-continued

Crystal data and structure refinement for 051810.

| | |
|---|---|
| Final R indices [I > 2σ(I)] | R1 = 0.0910, wR2 = 0.2214 |
| R indices (all data) | R1 = 0.1268, wR2 = 0.2524 |
| Extinction coefficient | 0.0124(12) |
| Largest diff. peak and hole | 0.366 and −0.305 e/Å$^3$ |
| Melting Point | 140-145° C. |

TABLE 2

Atomic coordinates (× 10$^4$) and equivalent isotropic displacement parameters (Å$^2$ × 10$^3$) for 051810. U(eq) is defined as one third of the trace of the orthogonalized U$_{ij}$ tensor.

| | x | y | z | U(eq) |
|---|---|---|---|---|
| O(1A) | −322(12) | 7615(2) | 6913(2) | 59(2) |
| O(3A) | −2739(11) | 9404(2) | 7179(1) | 51(1) |
| C(10A) | −165(18) | 8424(3) | 6486(2) | 47(2) |
| C(1A) | −994(17) | 8232(3) | 6868(2) | 46(2) |
| C(3A) | 148(16) | 9249(3) | 7108(2) | 49(2) |
| C(14A) | −7331(19) | 8940(3) | 5377(2) | 48(2) |
| C(4A) | 864(18) | 9437(3) | 6719(2) | 49(2) |
| C(13A) | −6378(17) | 9119(3) | 4990(2) | 42(2) |
| C(7A) | −4130(18) | 9025(3) | 5916(2) | 50(2) |
| C(17A) | −7691(17) | 8673(3) | 4726(2) | 47(2) |
| C(2A) | 472(16) | 8595(3) | 7156(2) | 47(2) |
| C(15A) | −7129(18) | 8276(3) | 5360(2) | 49(2) |
| C(8A) | −5795(16) | 9274(3) | 5667(2) | 43(2) |
| C(9A) | −6387(19) | 9924(3) | 5624(2) | 52(2) |
| C(12A) | −7120(18) | 9770(3) | 4931(2) | 46(2) |
| C(5A) | −649(16) | 9072(3) | 6439(2) | 43(2) |
| C(16A) | −8423(18) | 8158(3) | 4986(2) | 50(2) |
| C(21A) | −4792(18) | 9008(3) | 4177(2) | 48(2) |
| C(20A) | −5793(17) | 8486(3) | 4408(2) | 45(2) |
| C(11A) | −5708(19) | 10137(3) | 5234(2) | 51(2) |
| C(6A) | −2416(17) | 9326(3) | 6193(2) | 47(2) |
| C(22A) | −7262(18) | 8050(3) | 4144(2) | 55(2) |
| C(2A') | 1940(20) | 8381(3) | 7432(2) | 76(3) |
| O(3B) | −3150(11) | 10326(2) | 7677(1) | 48(1) |
| O(1B) | −4693(10) | 12069(2) | 8071(1) | 40(1) |
| C(1B) | −4362(16) | 11592(3) | 7816(2) | 39(2) |
| C(2B) | −6068(16) | 11074(3) | 7930(2) | 40(2) |
| C(10B) | −5147(19) | 11778(3) | 7423(2) | 49(2) |
| C(3B) | −5950(17) | 10575(3) | 7667(2) | 46(2) |
| C(4B) | −6576(18) | 10759(3) | 7270(2) | 48(2) |
| C(6B) | −3204(17) | 11254(3) | 6861(2) | 51(2) |
| C(5B) | −4833(17) | 11275(3) | 7155(2) | 44(2) |
| C(7B) | −1376(17) | 11745(4) | 6734(2) | 58(2) |
| C(2B') | −7707(19) | 11071(3) | 8221(2) | 56(2) |
| C(8B) | 259(18) | 11713(5) | 6435(3) | 75(3) |
| C(12B) | 2040(50) | 12137(10) | 5703(5) | 105(13) |
| C(9B) | 720(60) | 11337(11) | 6171(5) | 65(7) |
| C(14B) | 1730(40) | 12297(7) | 6369(5) | 66(5) |
| C(13B) | 1580(50) | 12609(9) | 5997(5) | 86(8) |
| C(11B) | 420(50) | 11584(11) | 5782(5) | 96(11) |
| C(15B) | 1870(60) | 12851(8) | 6602(7) | 111(14) |
| C(17B) | 3160(40) | 13190(9) | 5995(8) | 109(12) |
| C(16B) | 3350(40) | 13356(9) | 6404(7) | 101(9) |
| C(20B) | 2050(30) | 13662(10) | 5735(7) | 151(15) |
| C(22B) | 3890(50) | 14206(10) | 5741(8) | 185(18) |
| C(21B) | 1610(120) | 13442(14) | 5339(8) | 230(30) |
| C(12') | 1350(40) | 11726(7) | 5609(6) | 45(6) |
| C(9') | 160(70) | 11067(10) | 6145(6) | 46(8) |
| C(14') | 2290(40) | 12120(8) | 6246(4) | 45(8) |
| C(13') | 1240(50) | 12265(7) | 5860(4) | 36(6) |
| C(11') | −560(50) | 11251(8) | 5752(5) | 39(6) |
| C(15') | 2350(40) | 12687(8) | 6459(5) | 33(5) |
| C(17') | 2980(40) | 12809(6) | 5789(4) | 38(5) |
| C(16') | 3750(40) | 13067(7) | 6167(4) | 35(6) |
| C(20') | 1650(50) | 13270(7) | 5543(5) | 72(8) |
| C(22') | 3670(70) | 13750(10) | 5428(8) | 78(9) |
| C(21') | 80(60) | 13041(10) | 5206(6) | 76(9) |
| C(1) | 1350(40) | 14678(5) | 6378(3) | 67(5) |
| C(2) | 1060(20) | 14340(5) | 6695(4) | 64(5) |
| C(3) | 3410(30) | 14137(4) | 6879(2) | 69(5) |
| C(4) | 6050(20) | 14270(4) | 6746(3) | 58(5) |

TABLE 2-continued

Atomic coordinates (× $10^4$) and equivalent isotropic displacement parameters ($Å^2 × 10^3$) for 051810. U(eq) is defined as one third of the trace of the orthogonalized $U_{ij}$ tensor.

|       | x        | y        | z       | U(eq) |
|-------|----------|----------|---------|-------|
| C(5)  | 6340(20) | 14608(4) | 6429(3) | 62(5) |
| C(6)  | 3990(30) | 14811(4) | 6245(3) | 74(6) |

TABLE 3

Bondlengths [Å] for 051810.

| | |
|---|---|
| O(1A)—C(1A) | 1.460(8) |
| O(1A)—H(1AA) | 0.8200 |
| O(3A)—C(3A) | 1.454(9) |
| O(3A)—H(3AA) | 0.8200 |
| C(10A)—C(1A) | 1.502(9) |
| C(10A)—C(5A) | 1.513(10) |
| C(10A)—H(10A) | 0.9700 |
| C(10A)—H(10B) | 0.9700 |
| C(1A)—C(2A) | 1.508(11) |
| C(1A)—H(1AB) | 0.9800 |
| C(3A)—C(4A) | 1.507(10) |
| C(3A)—C(2A) | 1.518(10) |
| C(3A)—H(3AB) | 0.9800 |
| C(14A)—C(8A) | 1.492(10) |
| C(14A)—C(13A) | 1.527(10) |
| C(14A)—C(15A) | 1.529(9) |
| C(14A)—H(14A) | 0.9800 |
| C(4A)—C(5A) | 1.501(10) |
| C(4A)—H(4AA) | 0.9700 |
| C(4A)—H(4AB) | 0.9700 |
| C(13A)—C(17A) | 1.534(10) |
| C(13A)—C(12A) | 1.550(9) |
| C(13A)—H(13A) | 0.9800 |
| C(7A)—C(8A) | 1.332(10) |
| C(7A)—C(6A) | 1.469(10) |
| C(7A)—H(7AA) | 0.9300 |
| C(17A)—C(20A) | 1.529(10) |
| C(17A)—C(16A) | 1.548(10) |
| C(17A)—H(17A) | 0.9800 |
| C(2A)—C(2A') | 1.314(11) |
| C(15A)—C(16A) | 1.511(10) |
| C(15A)—H(15A) | 0.9700 |
| C(15A)—H(15B) | 0.9700 |
| C(8A)—C(9A) | 1.526(10) |
| C(9A)—C(11A) | 1.528(9) |
| C(9A)—H(9AA) | 0.9700 |
| C(9A)—H(9AB) | 0.9700 |
| C(12A)—C(11A) | 1.538(10) |
| C(12A)—H(12A) | 0.9700 |
| C(12A)—H(12B) | 0.9700 |
| C(5A)—C(6A) | 1.359(10) |
| C(16A)—H(16A) | 0.9700 |
| C(16A)—H(16B) | 0.9700 |
| C(21A)—C(20A) | 1.536(10) |
| C(21A)—H(21A) | 0.9600 |
| C(21A)—H(21B) | 0.9600 |
| C(21A)—H(21C) | 0.9600 |
| C(20A)—C(22A) | 1.552(10) |
| C(20A)—H(20A) | 0.9800 |
| C(11A)—H(11A) | 0.9700 |
| C(11A)—H(11B) | 0.9700 |
| C(6A)—H(6AA) | 0.9300 |
| C(22A)—H(22A) | 0.9600 |
| C(22A)—H(22B) | 0.9600 |
| C(22A)—H(22C) | 0.9600 |
| C(2A')—H(1A') | 0.9300 |
| C(2A')—H(2A') | 0.9300 |
| O(3B)—C(3B) | 1.461(10) |
| O(3B)—H(3BA) | 0.8200 |
| O(1B)—C(1B) | 1.439(8) |
| O(1B)—H(1BA) | 0.8200 |
| C(1B)—C(2B) | 1.501(10) |
| C(1B)—C(10B) | 1.532(9) |
| C(1B)—H(1BB) | 0.9800 |
| C(2B)—C(2B') | 1.313(10) |
| C(2B)—C(3B) | 1.488(10) |
| C(10B)—C(5B) | 1.514(9) |
| C(10B)—H(10C) | 0.9700 |
| C(10B)—H(10D) | 0.9700 |
| C(3B)—C(4B) | 1.526(7) |
| C(3B)—H(3BB) | 0.9800 |
| C(4B)—C(5B) | 1.506(10) |
| C(4B)—H(4BA) | 0.9700 |
| C(4)—H(4BB) | 0.9700 |
| C(6B)—C(5B) | 1.321(10) |
| C(6B)—C(7B) | 1.499(8) |
| C(6B)—H(6BA) | 0.9300 |
| C(7B)—C(8B) | 1.338(12) |
| C(7B)—H(7BA) | 0.9300 |
| C(2B')—H(1B') | 0.9300 |
| C(2B')—H(2B') | 0.9300 |
| C(8B)—C(9B) | 1.50(2) |
| C(8B)—C(14') | 1.514(10) |
| C(8B)—C(14B) | 1.534(10) |
| C(8B)—C(9') | 1.52(2) |
| C(12B)—C(11B) | 1.516(10) |
| C(12B)—C(13B) | 1.534(10) |
| C(12B)—H(12C) | 0.9700 |
| C(12B)—H(12D) | 0.9700 |
| C(9B)—C(11B) | 1.522(10) |
| C(9B)—H(9BA) | 0.9700 |
| C(9B)—H(9BB) | 0.9700 |
| C(14B)—C(15B) | 1.527(10) |
| C(14B)—C(13B) | 1.524(10) |
| C(14B)—H(14B) | 0.9800 |
| C(13B)—C(17B) | 1.532(10) |
| C(13B)—H(13B) | 0.9800 |
| C(11B)—H(11C) | 0.9700 |
| C(11B)—H(11D) | 0.9700 |
| C(15B)—H(15C) | 1.535(10) |
| C(15B)—H(15C) | 0.9700 |
| C(15B)—H(15D) | 0.9700 |
| C(17B)—C(16B) | 1.528(10) |
| C(17B)—C(20B) | 1.528(10) |
| C(17B)—H(17B) | 0.9800 |
| C(16B)—H(16C) | 0.9700 |
| C(16B)—H(16D) | 0.9700 |
| C(20B)—C(21B) | 1.528(10) |
| C(20B)—C(21B) | 1.532(11) |
| C(20B)—H(20B) | 0.9800 |
| C(22B)—H(22D) | 0.9600 |
| C(22B)—H(22E) | 0.9600 |
| C(22B)—H(22F) | 0.9600 |
| C(21B)—H(21D) | 0.9600 |
| C(21B)—H(21E) | 0.9600 |
| C(21B)—H(21F) | 0.9600 |
| C(12')—C(11') | 1.513(10) |
| C(12')—C(13') | 1.534(10) |
| C(12')—H(12E) | 0.9700 |
| C(12')—H(12F) | 0.9700 |
| C(9')—C(11') | 1.519(10) |
| C(9')—H(9BC) | 0.9700 |
| C(9')—H(9BD) | 0.9700 |
| C(14')—C(15') | 1.512(10) |
| C(14')—C(13') | 1.517(10) |
| C(14')—H(14') | 0.9800 |
| C(13')—C(17') | 1.523(10) |
| C(13')—H(13') | 0.9800 |
| C(11')—H(11E) | 0.9700 |
| C(11')—H(11F) | 0.9700 |
| C(15')—C(16') | 1.524(10) |
| C(15')—H(15E) | 0.9700 |
| C(15')—H(15F) | 0.9700 |
| C(17')—C(20') | 1.523(10) |
| C(17')—C(16') | 1.533(10) |
| C(17')—H(17') | 0.9800 |
| C(16')—H(16E) | 0.9700 |
| C(16')—H(16F) | 0.9700 |
| C(20')—C(21') | 1.525(10) |
| C(20')—C(22') | 1.528(10) |
| C(20')—H(20C) | 0.9800 |
| C(22')—H(22G) | 0.9600 |

TABLE 3-continued

Bondlengths [Å] for 051810.

| | |
|---|---|
| C(22')—H(22H) | 0.9600 |
| C(22')—H(22I) | 0.9600 |
| C(21')—H(21G) | 0.9600 |
| C(21')—H(21H) | 0.9600 |
| C(21')—H(21I) | 0.9600 |
| C(1)—C(2) | 1.3900 |
| C(1)—C(6) | 1.3900 |
| C(1)—H(1A) | 0.9300 |
| C(2)—C(3) | 1.3900 |
| C(2)—H(2A) | 0.9300 |
| C(3)—C(4) | 1.3900 |
| C(3)—H(3A) | 0.9300 |
| C(4)—C(5) | 1.3900 |
| C(4)—H(4A) | 0.9300 |
| C(5)—C(6) | 1.3900 |
| C(5)—H(5A) | 0.9300 |
| C(6)—H(6A) | 0.9300 |

TABLE 4

Bond angles [°] for 051810.

| | |
|---|---|
| C(1A)—O(1A)—H(1AA) | 109.5 |
| C(3A)—O(3A)—H(3AA) | 109.5 |
| C(1A)—C(10A)—C(5A) | 110.6(6) |
| C(1A)—C(10A)—H(10A) | 109.7 |
| C(5A)—C(10A)—H(10A) | 109.6 |
| C(1A)—C(10A)—H(10B) | 109.4 |
| C(5A)—C(10A)—H(10B) | 109.4 |
| H(10A)—C(10A)—H(10B) | 108.1 |
| O(1A)—C(1A)—C(10A) | 109.1(6) |
| O(1A)—C(1A)—C(2A) | 110.9(6) |
| C(10A)—C(1A)—C(2A) | 110.4(6) |
| O(1A)—C(1A)—H(1AB) | 108.8 |
| C(10A)—C(1A)—H(1AB) | 108.8 |
| C(2A)—C(1A)—H(1AB) | 108.8 |
| O(3A)—C(3A)—C(4A) | 108.2(6) |
| O(3A)—C(3A)—C(2A) | 108.6(6) |
| C(4A)—C(3A)—C(2A) | 111.5(6) |
| O(3A)—C(3A)—H(3AB) | 109.5 |
| C(4A)—C(3A)—H(3AB) | 109.5 |
| C(2A)—C(3A)—H(3AB) | 109.5 |
| C(8A)—C(14A)—C(13A) | 110.9(7) |
| C(8A)—C(14A)—C(15A) | 120.6(7) |
| C(13A)—C(14A)—C(15A) | 102.2(6) |
| C(8A)—C(14A)—H(14A) | 107.5 |
| C(13A)—C(14A)—H(14A) | 107.5 |
| C(15A)—C(14A)—H(14A) | 107.6 |
| C(5A)—C(4A)—C(3A) | 111.0(6) |
| C(5A)—C(4A)—H(4AA) | 109.4 |
| C(3A)—C(4A)—H(4AA) | 109.4 |
| C(5A)—C(4A)—H(4AB) | 109.4 |
| C(3A)—C(4A)—H(4AB) | 109.5 |
| H(4AA)—C(4A)—H(4AB) | 108.0 |
| C(14A)—C(13A)—C(17A) | 105.5(6) |
| C(14A)—C(13A)—C(12A) | 108.4(6) |
| C(17A)—C(13A)—C(12A) | 117.6(6) |
| C(14A)—C(13A)—H(13A) | 108.4 |
| C(17A)—C(13A)—H(13A) | 108.3 |
| C(12A)—C(13A)—H(13A) | 108.4 |
| C(8A)—C(7A)—C(6A) | 126.6(7) |
| C(8A)—C(7A)—H(7AA) | 116.8 |
| C(6A)—C(7A)—H(7AA) | 116.6 |
| C(20A)—C(17A)—C(13A) | 114.2(7) |
| C(20A)—C(17A)—C(16A) | 112.1(6) |
| C(13A)—C(17A)—C(16A) | 103.1(5) |
| C(20A)—C(17A)—H(17A) | 109.1 |
| C(13A)—C(17A)—H(17A) | 109.1 |
| C(16A)—C(17A)—H(17A) | 109.1 |
| C(2A')—C(2A)—C(1A) | 124.4(7) |
| C(2A')—C(2A)—C(3A) | 120.9(8) |
| C(1A)—C(2A)—C(3A) | 114.7(6) |
| C(16A)—C(15A)—C(14A) | 100.9(6) |
| C(16A)—C(15A)—H(15A) | 111.6 |
| C(14A)—C(15A)—H(15A) | 111.6 |

TABLE 4-continued

Bond angles [°] for 051810.

| | |
|---|---|
| C(16A)—C(15A)—H(15B) | 111.6 |
| C(14A)—C(15A)—H(15B) | 111.5 |
| H(15A)—C(15A)—H(15B) | 109.4 |
| C(7A)—C(8A)—C(14A) | 123.4(6) |
| C(7A)—C(8A)—C(9A) | 126.8(7) |
| C(14A)—C(8A)—C(9A) | 109.8(6) |
| C(11A)—C(9A)—C(8A) | 111.5(6) |
| C(11A)—C(9A)—H(9AA) | 109.3 |
| C(8A)—C(9A)—H(9AA) | 109.4 |
| C(11A)—C(9A)—H(9AB) | 109.3 |
| C(8A)—C(9A)—H(9AB) | 109.4 |
| H(9AA)—C(9A)—H(9AB) | 108.0 |
| C(11A)—C(12A)—C(13A) | 109.2(6) |
| C(11A)—C(12A)—H(12A) | 109.8 |
| C(13A)—C(12A)—H(12A) | 109.8 |
| C(11A)—C(12A)—H(12B) | 109.9 |
| C(13A)—C(12A)—H(12B) | 109.8 |
| H(12A)—C(12A)—H(12B) | 108.3 |
| C(6A)—C(5A)—C(4A) | 120.2(6) |
| C(6A)—C(5A)—C(10A) | 126.2(7) |
| C(4A)—C(5A)—C(10A) | 113.4(6) |
| C(15A)—C(16A)—C(17A) | 108.1(6) |
| C(15A)—C(16A)—H(16A) | 110.1 |
| C(17A)—C(16A)—H(16A) | 110.1 |
| C(15A)—C(16A)—H(16B) | 110.0 |
| C(17A)—C(16A)—H(16B) | 110.1 |
| H(16A)—C(16A)—H(16B) | 108.4 |
| C(20A)—C(21A)—H(21A) | 109.6 |
| C(20A)—C(21A)—H(21B) | 109.4 |
| H(21A)—C(21A)—H(21B) | 109.5 |
| C(20A)—C(21A)—H(21C) | 109.4 |
| H(21A)—C(21A)—H(21C) | 109.5 |
| H(21B)—C(21A)—H(21C) | 109.5 |
| C(17A)—C(20A)—C(21A) | 112.2(6) |
| C(17A)—C(20A)—C(22A) | 111.9(7) |
| C(21A)—C(20A)—C(22A) | 108.1(6) |
| C(17A)—C(20A)—H(20A) | 108.2 |
| C(21A)—C(20A)—H(20A) | 108.2 |
| C(22A)—C(20A)—H(20A) | 108.2 |
| C(9A)—C(11A)—C(12A) | 112.8(7) |
| C(9A)—C(11A)—H(11A) | 109.0 |
| C(12A)—C(11A)—H(11A) | 109.0 |
| C(9A)—C(11A)—H(11B) | 109.1 |
| C(12A)—C(11A)—H(11B) | 109.0 |
| H(11A)—C(11A)—H(11B) | 107.8 |
| C(5A)—C(6A)—C(7A) | 126.5(7) |
| C(5A)—C(6A)—H(6AA) | 116.8 |
| C(7A)—C(6A)—H(6AA) | 116.7 |
| C(20A)—C(22A)—H(22A) | 109.4 |
| C(20A)—C(22A)—H(22B) | 109.5 |
| H(22A)—C(22A)—H(22B) | 109.5 |
| C(20A)—C(22A)—H(22C) | 109.5 |
| H(22A)—C(22A)—H(22C) | 109.5 |
| H(22B)—C(22A)—H(22C) | 109.5 |
| C(2A)—C(2A')—H(1A') | 120.0 |
| C(2A)—C(2A')—H(2A') | 120.0 |
| H(1A')—C(2A')—H(2A') | 120.0 |
| C(3B)—O(3B)—H(3BA) | 109.4 |
| C(1B)—O(1B)—H(1BA) | 109.4 |
| O(1B)—C(1B)—C(2B) | 111.5(5) |
| O(1B)—C(1B)—C(10B) | 110.7(5) |
| C(2B)—C(1E)—C(10B) | 110.0(6) |
| O(1B)—C(1B)—H(1BB) | 108.2 |
| C(2B)—C(1B)—H(1BB) | 108.2 |
| C(10B)—C(1B)—H(1BB) | 108.2 |
| C(2B')—C(2B)—C(3B) | 122.1(7) |
| C(2B')—C(2B)—C(1B) | 123.4(7) |
| C(3B)—C(2B)—C(1B) | 114.4(6) |
| C(5B)—C(10B)—C(1B) | 110.8(6) |
| C(5B)—C(10B)—H(10C) | 109.6 |
| C(1B)—C(10B)—H(10C) | 109.5 |
| C(5B)—C(10B)—H(10D) | 109.4 |
| C(1B)—C(10B)—H(10D) | 109.5 |
| H(10C)—C(10B)—H(10D) | 108.1 |
| O(3B)—C(3B)—C(2B) | 108.7(6) |
| O(3B)—C(3B)—C(4B) | 108.2(6) |
| C(2B)—C(3B)—C(4B) | 112.4(6) |
| O(3B)—C(3B)—H(3BB) | 109.1 |

TABLE 4-continued

Bond angles [°] for 051810.

| | |
|---|---|
| C(2B)—C(3B)—H(3BB) | 109.2 |
| C(4B)—C(3B)—H(3BB) | 109.2 |
| C(5B)—C(4B)—C(3B) | 111.5(6) |
| C(5B)—C(4B)—H(4BA) | 109.3 |
| C(3B)—C(4B)—H(4BA) | 109.2 |
| C(5B)—C(4B)—H(4BB) | 109.4 |
| C(3B)—C(4B)—H(4BB) | 109.4 |
| H(4BA)—C(4B)—H(4BB) | 108.0 |
| C(5B)—C(68)—C(7B) | 124.5(7) |
| C(5B)—C(6B)—H(6BA) | 117.8 |
| C(7B)—C(6B)—H(6BA) | 117.7 |
| C(6B)—C(5B)—C(4B) | 121.5(6) |
| C(6B)—C(5B)—C(10B) | 126.9(7) |
| C(4B)—C(5B)—C(10B) | 111.6(6) |
| C(8B)—C(7B)—C(6B) | 123.3(8) |
| C(8B)—C(7B)—H(7BA) | 118.3 |
| C(6B)—C(7B)—H(7BA) | 118.4 |
| C(2B)—C(2B')—H(1B') | 120.1 |
| C(2B)—C(2B')—H(2B') | 119.9 |
| H(1B')—C(2B')—H(2B') | 120.0 |
| C(9B)—C(8B)—C(7B) | 136.7(13) |
| C(9B)—C(8B)—C(14') | 88.1(14) |
| C(7B)—C(8B)—C(14') | 135.1(12) |
| C(9B)—C(8B)—C(14B) | 112.6(15) |
| C(7B)—C(8B)—C(14B) | 110.4(11) |
| C(14')—C(8B)—C(14B) | 24.9(8) |
| C(9B)—C(8B)—C(9') | 16.9(16) |
| C(7B)—C(8B)—C(9') | 119.8(12) |
| C(14')—C(8B)—C(9') | 105.0(13) |
| C(14B)—C(8B)—C(9') | 129.4(13) |
| C(11B)—C(12B)—C(13B) | 112.7(18) |
| C(11B)—C(12B)—H(12C) | 108.9 |
| C(13B)—C(12B)—H(12C) | 108.6 |
| C(11B)—C(12B)—H(12D) | 109.3 |
| C(13B)—C(12B)—H(12D) | 109.5 |
| H(12C)—C(12B)—H(12D) | 107.8 |
| C(8B)—C(9B)—C(11B) | 114.4(19) |
| C(8B)—C(9B)—H(9BA) | 109.1 |
| C(11B)—C(9B)—H(9BA) | 108.4 |
| C(8B)—C(9B)—H(9BB) | 108.6 |
| C(11B)—C(9B)—H(9BB) | 108.6 |
| H(9BA)—C(9B)—H(9BB) | 107.6 |
| C(15B)—C(14B)—C(13B) | 95.5(15) |
| C(15B)—C(14B)—C(8B) | 131.5(13) |
| C(13B)—C(14B)—C(8B) | 121.8(14) |
| C(15B)—C(14B)—H(14B) | 100.6 |
| C(13B)—C(14B)—H(14B) | 101.3 |
| C(8B)—C(14B)—H(14B) | 101.0 |
| C(14B)—C(13B)—C(17B) | 113.0(14) |
| C(14B)—C(13B)—C(12B) | 105.8(15) |
| C(17B)—C(13B)—C(12B) | 122.6(18) |
| C(14B)—C(13B)—H(13B) | 104.3 |
| C(17B)—C(13B)—H(13B) | 104.4 |
| C(12B)—C(13B)—H(13B) | 105.0 |
| C(12B)—C(11B)—C(9B) | 115.9(19) |
| C(12B)—C(11B)—H(11C) | 108.0 |
| C(9B)—C(11B)—H(11C) | 108.5 |
| C(12B)—C(11B)—H(11D) | 108.5 |
| C(9B)—C(11B)—H(11D) | 108.3 |
| H(11C)—C(11B)—H(11D) | 107.4 |
| C(14B)—C(15B)—C(16B) | 113.1(17) |
| C(14B)—C(15B)—H(15C) | 109.4 |
| C(16B)—C(15B)—H(15C) | 109.8 |
| C(14B)—C(15B)—H(15D) | 107.9 |
| C(16B)—C(15B)—H(15D) | 108.7 |
| H(15C)—C(15B)—H(15D) | 107.6 |
| C(16B)—C(17B)—C(20B) | 115.9(19) |
| C(16B)—C(17B)—C(13B) | 104.0(16) |
| C(20B)—C(17B)—C(13B) | 116.6(16) |
| C(16B)—C(17B)—H(17B) | 106.2 |
| C(20B)—C(17B)—H(17B) | 106.6 |
| C(13B)—C(17B)—H(17B) | 106.7 |
| C(17B)—C(16B)—C(15B) | 103.5(18) |
| C(17B)—C(16B)—H(16C) | 111.1 |
| C(15B)—C(16B)—H(16C) | 110.8 |
| C(17B)—C(16B)—H(16D) | 111.7 |
| C(15B)—C(16B)—H(16D) | 110.5 |
| H(16C)—C(16B)—H(16D) | 109.2 |
| C(22B)—C(20B)—C(17B) | 111.7(17) |
| C(22B)—C(20B)—C(21B) | 111(2) |
| C(17B)—C(20B)—C(21B) | 113(2) |
| C(22B)—C(20B)—2(20B) | 107.2 |
| C(17B)—C(20B)—H(20B) | 107.2 |
| C(21B)—C(20B)—H(20B) | 106.3 |
| C(20B)—C(22B)—H(22D) | 109.5 |
| C(20B)—C(22B)—H(22E) | 109.5 |
| H(22D)—C(22B)—H(22E) | 109.5 |
| C(20B)—C(22B)—H(22F) | 109.3 |
| H(22D)—C(22B)—H(22F) | 109.5 |
| H(22E)—C(22B)—H(22F) | 109.5 |
| C(20B)—C(21B)—H(21D) | 110.2 |
| C(20B)—C(21B)—H(21E) | 109.4 |
| H(21D)—C(21B)—H(21E) | 109.5 |
| C(20B)—C(21B)—H(21F) | 108.8 |
| H(21D)—C(21B)—H(21F) | 109.5 |
| H(21E)—C(21B)—H(21F) | 109.5 |
| C(11')—C(12')—C(13') | 111.0(13) |
| C(11')—C(12')—H(12E) | 109.4 |
| C(13')—C(12')—H(12E) | 109.7 |
| C(11')—C(12')—H(12F) | 109.8 |
| C(13')—C(12')—H(12F) | 108.9 |
| H(12E)—C(12')—H(12F) | 108.0 |
| C(11')—C(9')—C(8B) | 108.5(15) |
| C(11')—C(9')—H(9BC) | 110.2 |
| C(8B)—C(9')—H(9BC) | 109.7 |
| C(11')—C(9')—H(9BD) | 109.9 |
| C(8B)—C(9')—H(9BD) | 110.3 |
| H(9BC)—C(9')—H(9BD) | 108.3 |
| C(8B)—C(14')—C(15') | 108.3(13) |
| C(8B)—C(14')—C(13') | 109.7(13) |
| C(15')—C(14')—C(13') | 106.5(15) |
| C(8B)—C(14')—H(14') | 111.1 |
| C(15')—C(14')—H(14') | 110.6 |
| C(13')—C(14')—H(14') | 110.5 |
| C(14')—C(13')—C(17') | 98.8(11) |
| C(14')—C(13')—C(12') | 110.8(17) |
| C(17')—C(13')—C(12') | 122.8(15) |
| C(14')—C(13')—H(13') | 107.9 |
| C(17')—C(13')—H(13') | 107.7 |
| C(12')—C(13')—H(13') | 107.8 |
| C(12')—C(11')—C(9') | 112.5(18) |
| C(12')—C(11')—H(11E) | 108.6 |
| C(9')—C(11')—H(11E) | 108.7 |
| C(12')—C(11')—H(11F) | 109.6 |
| C(9')—C(11')—H(11F) | 109.5 |
| H(11E)—C(11')—H(11F) | 107.9 |
| C(14')—C(15')—C(16') | 98.5(12) |
| C(14')—C(15')—H(15E) | 112.0 |
| C(16')—C(15')—H(15E) | 112.7 |
| C(14')—C(15')—H(15F) | 111.7 |
| C(16')—C(15')—H(15F) | 111.9 |
| H(15E)—C(15')—H(15F) | 109.7 |
| C(20')—C(17')—C(13') | 115.8(13) |
| C(20')—C(17')—C(16') | 110.6(13) |
| C(13')—C(17')—C(16') | 107.3(13) |
| C(20')—C(17')—H(17') | 107.9 |
| C(13')—C(17')—H(17') | 107.4 |
| C(16')—C(17')—H(17') | 107.5 |
| C(15')—C(16')—C(17') | 106.8(14) |
| C(15')—C(16')—H(16E) | 109.9 |
| C(17')—C(16')—H(16E) | 110.7 |
| C(15')—C(16')—H(16F) | 110.1 |
| C(17')—C(16')—H(16F) | 110.8 |
| H(16E)—C(16')—H(16F) | 108.6 |
| C(17')—C(20')—C(21') | 115.7(14) |
| C(17')—C(20')—C(22') | 112.9(18) |
| C(21')—C(20')—C(22') | 110(2) |
| C(17')—C(20')—H(20C) | 105.6 |
| C(21')—C(20')—H(20C) | 105.5 |
| C(22')—C(20')—H(20C) | 105.8 |
| C(20')—C(22')—H(22G) | 109.6 |
| C(20')—C(22')—H(22H) | 109.7 |
| H(22G)—C(22')—H(22H) | 109.5 |
| C(20')—C(22')—H(22I) | 109.1 |
| H(22G)—C(22')—H(22I) | 109.5 |
| H(22H)—C(22')—H(22I) | 109.5 |

TABLE 4-continued

Bond angles [°] for 051810.

| | |
|---|---|
| C(20')—C(21')—H(21G) | 109.3 |
| C(20')—C(21')—H(21H) | 109.7 |
| H(21G)—C(21')—H(21H) | 109.5 |
| C(20')—C(21')—H(21I) | 109.5 |
| H(21G)—C(21')—H(21I) | 109.5 |
| H(21H)—C(21')—H(21I) | 109.5 |
| C(2)—C(1)—C(6) | 120.0 |
| C(2)—C(1)—H(1A) | 120.0 |
| C(6)—C(1)—H(1A) | 120.0 |
| C(1)—C(2)—C(3) | 120.0 |
| C(1)—C(2)—H(2A) | 120.0 |
| C(3)—C(2)—H(2A) | 120.0 |
| C(2)—C(3)—C(4) | 120.0 |
| C(2)—C(3)—H(3A) | 120.0 |
| C(4)—C(3)—H(3A) | 120.0 |
| C(5)—C(4)—C(3) | 120.0 |
| C(5)—C(4)—H(4A) | 120.0 |
| C(3)—C(4)—H(4A) | 120.0 |
| C(4)—C(5)—C(6) | 120.00(5) |
| C(4)—C(5)—H(5A) | 120.0 |
| C(6)—C(5)—H(5A) | 120.0 |
| C(5)—C(6)—C(1) | 120.0 |
| C(5)—C(6)—H(6A) | 120.0 |
| C(1)—C(6)—H(6A) | 120.0 |

TABLE 5

Anisotropic displacement parameters [Å² × 10³] for 051810.

| | $U_{11}$ | $U_{22}$ | $U_{33}$ | $U_{23}$ | $U_{13}$ | $U_{12}$ |
|---|---|---|---|---|---|---|
| O (1A) | 50 (4) | 34 (3) | 93 (4) | 21 (3) | 2 (3) | 9 (3) |
| O (3A) | 41 (4) | 48 (3) | 64 (3) | −2 (3) | 7 (3) | 6 (3) |
| C (10A) | 53 (6) | 33 (4) | 54 (5) | −5 (3) | −2 (4) | −4 (4) |
| C (1A) | 35 (5) | 27 (4) | 76 (5) | 12 (4) | 3 (4) | 5 (3) |
| C (3A) | 37 (5) | 36 (4) | 75 (5) | −2 (4) | −6 (4) | 4 (4) |
| C (14A) | 53 (6) | 36 (4) | 56 (5) | 3 (4) | 0 (4) | 6 (4) |
| C (4A) | 50 (6) | 36 (4) | 61 (5) | 7 (4) | 0 (4) | −6 (4) |
| C (13A) | 42 (5) | 35 (4) | 50 (4) | 8 (3) | 4 (4) | 9 (4) |
| C (7A) | 60 (6) | 35 (4) | 55 (5) | −8 (4) | 13 (4) | −9 (4) |
| C (17A) | 42 (5) | 45 (4) | 52 (5) | 7 (4) | −3 (4) | 3 (4) |
| C (2A) | 41 (5) | 50 (5) | 50 (4) | 12 (4) | 8 (4) | 4 (4) |
| C (15A) | 52 (6) | 39 (4) | 58 (5) | 8 (4) | 6 (4) | 0 (4) |
| C (8A) | 44 (5) | 35 (4) | 50 (5) | 8 (4) | 4 (4) | 6 (4) |
| C (9A) | 53 (6) | 47 (4) | 56 (5) | 2 (4) | 10 (4) | 1 (4) |
| C (12A) | 54 (6) | 36 (4) | 46 (5) | 6 (3) | 2 (4) | 9 (4) |
| C (5A) | 36 (5) | 39 (4) | 55 (4) | 0 (4) | 4 (4) | 1 (4) |
| C (16A) | 43 (5) | 44 (5) | 62 (5) | 4 (4) | −3 (4) | 2 (4) |
| C (21A) | 48 (6) | 43 (4) | 53 (4) | 1 (4) | 2 (4) | 10 (4) |
| C (20A) | 39 (5) | 38 (4) | 57 (5) | 1 (4) | −1 (4) | 4 (4) |
| C (11A) | 59 (6) | 40 (4) | 53 (5) | 4 (4) | 3 (4) | 5 (4) |
| C (6A) | 50 (5) | 33 (4) | 60 (5) | 2 (4) | 8 (4) | −3 (4) |
| C (22A) | 59 (6) | 47 (5) | 59 (5) | 0 (4) | −12 (4) | −1 (4) |
| C (2A') | 77 (8) | 78 (6) | 74 (6) | −4 (5) | −5 (5) | 33 (6) |
| O (3B) | 49 (4) | 34 (3) | 60 (3) | −1 (2) | −3 (3) | 4 (2) |
| O (1B) | 48 (3) | 31 (3) | 41 (3) | −5 (2) | −3 (2) | 4 (2) |
| C (1B) | 44 (5) | 28 (4) | 45 (4) | −2 (3) | −1 (3) | −4 (3) |
| C (2B) | 37 (5) | 42 (4) | 41 (4) | −3 (3) | 0 (3) | −4 (3) |
| C (10B) | 54 (6) | 38 (4) | 56 (5) | −3 (4) | 3 (4) | −3 (4) |
| C (3B) | 49 (5) | 32 (4) | 57 (5) | −6 (4) | 0 (4) | −3 (4) |
| C (4B) | 49 (5) | 39 (4) | 55 (5) | −10 (4) | 3 (4) | −2 (4) |
| C (6B) | 49 (6) | 55 (5) | 48 (5) | −6 (4) | −4 (4) | 10 (4) |
| C (5B) | 45 (5) | 36 (4) | 51 (4) | −10 (3) | −3 (4) | 10 (4) |
| C (7B) | 38 (5) | 79 (6) | 57 (5) | 15 (4) | 1 (4) | 12 (5) |
| C (2B') | 59 (6) | 42 (5) | 66 (5) | −1 (4) | 1 (5) | 4 (4) |
| C (8B) | 33 (6) | 124 (9) | 68 (6) | 37 (7) | 6 (5) | 28 (6) |
| C (12B) | 83 (18) | 190 (30) | 43 (14) | 64 (16) | 31 (12) | 80 (20) |
| C (9B) | 43 (13) | 100 (20) | 48 (13) | 5 (13) | −7 (9) | 8 (16) |
| C (14B) | 16 (11) | 118 (13) | 63 (11) | 38 (10) | 26 (8) | 27 (10) |
| C (13B) | 74 (16) | 109 (16) | 74 (15) | 40 (15) | 38 (13) | 44 (15) |
| C (11B) | 32 (16) | 170 (40) | 89 (19) | 40 (20) | 22 (12) | 20 (17) |
| C (15B) | 44 (14) | 140 (30) | 150 (30) | 110 (20) | 30 (20) | 20 (20) |
| C (17B) | 9 (12) | 87 (19) | 230 (30) | 70 (20) | −3 (15) | 13 (11) |
| C (16B) | 50 (13) | 84 (15) | 170 (20) | 66 (17) | 0 (13) | −1 (11) |
| C (20B) | 110 (20) | 140 (30) | 200 (30) | 120 (30) | 70 (20) | 90 (20) |
| C (22B) | 120 (20) | 140 (20) | 300 (40) | 140 (30) | 130 (30) | 51 (19) |
| C (21B) | 410 (90) | 170 (50) | 120 (30) | 100 (40) | 100 (50) | 100 (50) |
| C (12') | 44 (15) | 10 (9) | 82 (17) | −11 (11) | 3 (11) | 0 (9) |
| C (9') | 38 (17) | 23 (13) | 77 (17) | −8 (11) | −5 (11) | −1 (10) |
| C (14') | 18 (16) | 64 (14) | 53 (16) | 17 (12) | 35 (15) | 35 (12) |
| C (13') | 50 (16) | 34 (14) | 26 (13) | −8 (9) | 2 (11) | 0 (12) |
| C (11') | 34 (14) | 42 (12) | 41 (11) | −8 (9) | 0 (9) | −22 (9) |
| C (15') | 15 (13) | 44 (9) | 39 (10) | 12 (7) | 5 (7) | −3 (8) |
| C (17') | 44 (13) | 13 (11) | 56 (12) | 2 (9) | −7 (10) | −4 (9) |
| C (16') | 37 (14) | 14 (10) | 56 (13) | −22 (10) | −7 (11) | 12 (9) |
| C (20') | 130 (20) | 48 (17) | 42 (14) | −7 (13) | −1 (15) | −9 (16) |
| C (22') | 160 (30) | 31 (13) | 46 (14) | 5 (11) | 35 (15) | −24 (14) |
| C (21') | 120 (20) | 49 (15) | 56 (14) | 18 (11) | −35 (14) | 9 (14) |
| C (1) | 55 (14) | 51 (11) | 95 (14) | −8 (10) | 2 (10) | 11 (9) |
| C (2) | 62 (14) | 50 (10) | 80 (13) | −31 (10) | 15 (10) | 9 (10) |
| C (3) | 83 (16) | 53 (10) | 71 (12) | −10 (9) | 12 (12) | −1 (11) |
| C (4) | 63 (13) | 36 (9) | 74 (12) | −12 (8) | 3 (9) | 4 (9) |
| C (5) | 91 (15) | 30 (9) | 67 (12) | 7 (8) | 7 (11) | 3 (9) |
| C (6) | 87 (17) | 49 (11) | 85 (13) | −1 (10) | 7 (13) | 11 (11) |

The anisotropic displacement factor exponent takes the form: $-2\pi^2$ [$h^2 a^{*2} U_{11}$ + ... + $2hka^*b^* U_{12}$]

TABLE 6

Hydrogen coordinates (×10⁴) and isotropic displacement parameters (Å² × 10³) for 051810.

| | x | y | z | U(eq) |
|---|---|---|---|---|
| H(1AA) | −772 | 7508 | 7121 | 88 |
| H(3AA) | −3165 | 9304 | 7389 | 76 |
| H(10A) | −1247 | 8212 | 6304 | 56 |
| H(10B) | 1787 | 8337 | 6445 | 56 |
| H(1AB) | −3008 | 8283 | 6896 | 55 |
| H(3AB) | 1358 | 9452 | 7284 | 59 |
| H(14A) | −9307 | 9042 | 5399 | 58 |
| H(4AA) | 363 | 9843 | 6686 | 59 |
| H(4AB) | 2855 | 9400 | 6681 | 59 |
| H(13A) | −4349 | 9078 | 4977 | 51 |
| H(7AA) | −4044 | 8620 | 5914 | 60 |
| H(17A) | −9414 | 8836 | 4624 | 56 |
| H(15A) | −5210 | 8145 | 5369 | 59 |
| H(15B) | −8177 | 8093 | 5557 | 59 |
| H(9AA) | −8336 | 9998 | 5677 | 62 |
| H(9AB) | −5281 | 10140 | 5802 | 62 |
| H(12A) | −6487 | 9896 | 4689 | 55 |
| H(12b) | −9123 | 9821 | 4943 | 55 |
| H(16A) | −10428 | 8123 | 5010 | 60 |
| H(16B) | −7704 | 7797 | 4884 | 60 |
| H(21A) | −3850 | 9281 | 4334 | 72 |
| H(21B) | −6364 | 9194 | 4063 | 72 |
| H(21C) | −3535 | 8874 | 3988 | 72 |
| H(20A) | −4155 | 8293 | 4514 | 53 |
| H(11A) | −3707 | 10126 | 5198 | 61 |
| H(11B) | −6304 | 10539 | 5209 | 61 |
| H(6AA) | −2553 | 9730 | 6201 | 57 |
| H(22A) | −5981 | 7928 | 3955 | 82 |
| H(22B) | −8841 | 8235 | 4031 | 82 |
| H(22C) | −7870 | 7716 | 4282 | 82 |
| H(1A') | 2123 | 7979 | 7458 | 114 |
| H(2A') | 2789 | 8630 | 7600 | 114 |
| H(3BA) | −2777 | 10226 | 7889 | 72 |
| H(1BA) | −4248 | 11964 | 8280 | 60 |
| H(1BB) | −2397 | 11477 | 7816 | 47 |
| H(10C) | −7059 | 11915 | 7420 | 59 |
| H(10D) | −3958 | 12098 | 7346 | 59 |
| H(3BB) | −7298 | 10278 | 7744 | 55 |
| H(4BA) | −6208 | 10435 | 7105 | 57 |
| H(4BB) | −8532 | 10859 | 7249 | 57 |
| H(6BA) | −3190 | 10912 | 6723 | 61 |

TABLE 6-continued

Hydrogen coordinates (×10$^4$) and isotropic displacement parameters (Å$^2$ × 10$^3$) for 051810.

| | x | y | z | U(eq) |
|---|---|---|---|---|
| H(7BA) | −1379 | 12089 | 6870 | 69 |
| H(1B') | −8841 | 10751 | 8268 | 84 |
| H(2B') | −7733 | 11389 | 8381 | 84 |
| H(12C) | 1489 | 12288 | 5463 | 126 |
| H(12D) | 4012 | 12045 | 5691 | 126 |
| H(9BA) | −563 | 11014 | 6199 | 78 |
| H(9BB) | 2594 | 11184 | 6199 | 78 |
| H(14B) | 3687 | 12175 | 6372 | 79 |
| H(13B) | −381 | 12719 | 5970 | 103 |
| H(11C) | 1004 | 11288 | 5606 | 115 |
| H(11D) | −1538 | 11661 | 5737 | 115 |
| H(15C) | 2846 | 12767 | 6831 | 134 |
| H(15D) | −5 | 12972 | 6664 | 134 |
| H(17B) | 5058 | 13103 | 5913 | 131 |
| H(16C) | 2418 | 13724 | 6451 | 121 |
| H(16D) | 5278 | 13387 | 6482 | 121 |
| H(20B) | 220 | 13778 | 5830 | 181 |
| H(22D) | 3864 | 14386 | 5502 | 277 |
| H(22E) | 5760 | 14097 | 5804 | 277 |
| H(22F) | 3189 | 14475 | 5922 | 277 |
| H(21D) | −117 | 13593 | 5245 | 349 |
| H(21E) | 1547 | 13024 | 5339 | 349 |
| H(21F) | 3116 | 13572 | 5186 | 349 |
| H(12E) | 785 | 11834 | 5360 | 54 |
| H(12F) | 3241 | 11581 | 5598 | 54 |
| H(9BC) | 1963 | 10874 | 6148 | 55 |
| H(9BD) | −1223 | 10796 | 6237 | 55 |
| H(14') | 4150 | 11946 | 6235 | 54 |
| H(13') | −708 | 12386 | 5882 | 44 |
| H(11E) | −427 | 10915 | 5590 | 47 |
| H(11F) | −2464 | 11390 | 5746 | 47 |
| H(15E) | 3449 | 12658 | 6683 | 39 |
| H(15F) | 490 | 12824 | 6519 | 39 |
| H(17') | 4716 | 12684 | 5669 | 45 |
| H(16E) | 5753 | 13064 | 6201 | 42 |
| H(16F) | 3094 | 13466 | 6185 | 42 |
| H(20C) | 240 | 13461 | 5697 | 87 |
| H(22G) | 2711 | 14036 | 5282 | 118 |
| H(22H) | 5163 | 13584 | 5286 | 118 |
| H(22I) | 4425 | 13933 | 5646 | 118 |
| H(21G) | −707 | 13362 | 5071 | 114 |
| H(21H) | −1382 | 12784 | 5285 | 114 |
| H(21I) | 1345 | 12832 | 5048 | 114 |
| H(1A) | −219 | 14814 | 6255 | 81 |
| H(2A) | −706 | 14251 | 6784 | 77 |
| H(3A) | 3213 | 13911 | 7091 | 83 |
| H(4A) | 7619 | 14134 | 6869 | 69 |
| H(5A) | 8105 | 14697 | 6340 | 75 |
| H(6A) | 4186 | 15037 | 6032 | 89 |

TABLE 7

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|
| 2 | 0 | 0 | 42 | 37 | 16 | 3 | 0 | 1 | 336 | 325 | 28 | 2 | 11 | 1 | 322 | 300 | 23 | 2 | 11 | 2 | 356 | 337 | 16 |
| 4 | 0 | 0 | 138 | 110 | 15 | 4 | 0 | 1 | 0 | 25 | 1 | 3 | 11 | 1 | 63 | 25 | 49 | 3 | 11 | 2 | 206 | 176 | 15 |
| -1 | 1 | 0 | 437 | 450 | 11 | -3 | 1 | 1 | 201 | 154 | 25 | -4 | 12 | 1 | 194 | 205 | 21 | -4 | 12 | 2 | 92 | 98 | 42 |
| 1 | 1 | 0 | 362 | 322 | 16 | -2 | 1 | 1 | 116 | 114 | 8 | -3 | 12 | 1 | 232 | 275 | 22 | -3 | 12 | 2 | 200 | 196 | 18 |
| 3 | 1 | 0 | 252 | 218 | 24 | -1 | 1 | 1 | 1143 | 962 | 30 | -2 | 12 | 1 | 284 | 258 | 14 | -2 | 12 | 2 | 178 | 157 | 9 |
| -2 | 2 | 0 | 271 | 282 | 8 | 0 | 1 | 1 | 134 | 157 | 3 | -1 | 12 | 1 | 680 | 694 | 18 | -1 | 12 | 2 | 294 | 255 | 15 |
| 0 | 2 | 0 | 426 | 437 | 14 | 1 | 1 | 1 | 1115 | 961 | 54 | 0 | 12 | 1 | 522 | 526 | 30 | 0 | 12 | 2 | 286 | 242 | 28 |
| 2 | 2 | 0 | 277 | 256 | 13 | 2 | 1 | 1 | 125 | 114 | 9 | 1 | 12 | 1 | 509 | 525 | 23 | 1 | 12 | 2 | 275 | 255 | 15 |
| 4 | 2 | 0 | 352 | 250 | 29 | 3 | 1 | 1 | 212 | 154 | 23 | 2 | 12 | 1 | 260 | 258 | 9 | 2 | 12 | 2 | 167 | 157 | 9 |
| -1 | 3 | 0 | 177 | 155 | 27 | 4 | 1 | 1 | 159 | 141 | 16 | 3 | 12 | 1 | 285 | 275 | 14 | 3 | 12 | 2 | 216 | 196 | 31 |
| 1 | 3 | 0 | 400 | 366 | 10 | -3 | 2 | 1 | 441 | 430 | 24 | -4 | 13 | 1 | 198 | 205 | 20 | -4 | 13 | 2 | 110 | 98 | 16 |
| 3 | 3 | 0 | 502 | 441 | 25 | -2 | 2 | 1 | 436 | 399 | 19 | -3 | 13 | 1 | 80 | 79 | 45 | -3 | 13 | 2 | 161 | 165 | 22 |
| -2 | 4 | 0 | 108 | 115 | 41 | -1 | 2 | 1 | 1871 | 1484 | 56 | -2 | 13 | 1 | 91 | 91 | 13 | -2 | 13 | 2 | 209 | 217 | 18 |
| 0 | 4 | 0 | 2471 | 1827 | 86 | 0 | 2 | 1 | 142 | 155 | 117 | -1 | 13 | 1 | 164 | 146 | 11 | -1 | 13 | 2 | 67 | 40 | 28 |
| 2 | 4 | 0 | 364 | 399 | 10 | 1 | 2 | 1 | 1819 | 1485 | 28 | 0 | 13 | 1 | 365 | 339 | 38 | 0 | 13 | 2 | 136 | 167 | 32 |
| 4 | 4 | 0 | 337 | 336 | 22 | 2 | 2 | 1 | 432 | 400 | 34 | 1 | 13 | 1 | 152 | 147 | 10 | 1 | 13 | 2 | 457 | 437 | 21 |
| -1 | 5 | 0 | 262 | 232 | 20 | 3 | 2 | 1 | 453 | 431 | 36 | 2 | 13 | 1 | 69 | 92 | 17 | 2 | 13 | 2 | 173 | 167 | 12 |
| 1 | 5 | 0 | 121 | 91 | 37 | 4 | 2 | 1 | 117 | 84 | 19 | 3 | 13 | 1 | 292 | 333 | 16 | 3 | 13 | 2 | 60 | 40 | 20 |
| 3 | 5 | 0 | 76 | 86 | 7 | -3 | 3 | 1 | 95 | 101 | 23 | -3 | 14 | 1 | 80 | 79 | 19 | -3 | 14 | 2 | 221 | 217 | 11 |
| -2 | 6 | 0 | 79 | 85 | 29 | -2 | 3 | 1 | 356 | 355 | 26 | -2 | 14 | 1 | 132 | 123 | 26 | -2 | 14 | 2 | 166 | 164 | 34 |
| 0 | 6 | 0 | 117 | 101 | 12 | -1 | 3 | 1 | 861 | 840 | 47 | -1 | 14 | 1 | 56 | 95 | 55 | -1 | 14 | 2 | 106 | 114 | 13 |
| 2 | 6 | 0 | 175 | 222 | 27 | 0 | 3 | 1 | 1901 | 1442 | 30 | 0 | 14 | 1 | 247 | 228 | 11 | 0 | 14 | 2 | 170 | 192 | 14 |
| 4 | 6 | 0 | 296 | 309 | 14 | 1 | 3 | 1 | 857 | 839 | 23 | 1 | 14 | 1 | 83 | 79 | 16 | 1 | 14 | 2 | 118 | 88 | 17 |
| -1 | 7 | 0 | 589 | 676 | 20 | 2 | 3 | 1 | 358 | 354 | 15 | 2 | 14 | 1 | 324 | 311 | 30 | 2 | 14 | 2 | 197 | 158 | 23 |
| 1 | 7 | 0 | 86 | 46 | 29 | 3 | 3 | 1 | 139 | 100 | 57 | 3 | 14 | 1 | 65 | 79 | 9 | 3 | 14 | 2 | 66 | 57 | 26 |
| 3 | 7 | 0 | 199 | 199 | 14 | 4 | 3 | 1 | 89 | 72 | 30 | -3 | 15 | 1 | 261 | 227 | 31 | -3 | 15 | 2 | 171 | 158 | 11 |
| -2 | 8 | 0 | 111 | 130 | 6 | -3 | 4 | 1 | 146 | 157 | 11 | -2 | 15 | 1 | 77 | 94 | 14 | -2 | 15 | 2 | 81 | 89 | 16 |
| 0 | 8 | 0 | 99 | 12 | 27 | -2 | 4 | 1 | 294 | 284 | 20 | -1 | 15 | 1 | 116 | 123 | 11 | -1 | 15 | 2 | 165 | 192 | 18 |
| 2 | 8 | 0 | 164 | 132 | 10 | -1 | 4 | 1 | 334 | 364 | 11 | 0 | 15 | 1 | 11 | 72 | 20 | 0 | 15 | 2 | 118 | 114 | 14 |
| 4 | 8 | 0 | 833 | 923 | 65 | 0 | 4 | 1 | 415 | 903 | 26 | 1 | 15 | 1 | 164 | 167 | 26 | 1 | 15 | 2 | 92 | 86 | 21 |
| -1 | 9 | 0 | 272 | 335 | 26 | 1 | 4 | 1 | 961 | 464 | 16 | 2 | 15 | 1 | 119 | 102 | 10 | 2 | 15 | 2 | 201 | 183 | 9 |
| 1 | 9 | 0 | 75 | 86 | 41 | 2 | 4 | 1 | 415 | 464 | 19 | -3 | 16 | 1 | 62 | 54 | 23 | -3 | 16 | 2 | 122 | 96 | 15 |
| 3 | 9 | 0 | 158 | 156 | 23 | 3 | 4 | 1 | 308 | 364 | 22 | -2 | 16 | 1 | 88 | 103 | 19 | -2 | 16 | 2 | 16 | 5 | 13 |
| -2 | 10 | 0 | 300 | 305 | 18 | 4 | 4 | 1 | 292 | 283 | 12 | -1 | 16 | 1 | 166 | 167 | 10 | -1 | 16 | 2 | 125 | 97 | 13 |
| 0 | 10 | 0 | 293 | 277 | 14 | -3 | 5 | 1 | 154 | 156 | 28 | 0 | 16 | 1 | 761 | 787 | 24 | 0 | 16 | 2 | 197 | 182 | 13 |
| 2 | 10 | 0 | 306 | 302 | 16 | -2 | 5 | 1 | 218 | 162 | 21 | 1 | 16 | 1 | 393 | 436 | 25 | 1 | 16 | 2 | 71 | 87 | 41 |
| -1 | 11 | 0 | 259 | 184 | 39 | -1 | 5 | 1 | 251 | 211 | 16 | 2 | 16 | 1 | 744 | 787 | 20 | 2 | 16 | 2 | 161 | 175 | 29 |
| 1 | 11 | 0 | 259 | 210 | 11 | 0 | 5 | 1 | 621 | 673 | 26 | -2 | 17 | 1 | 344 | 301 | 14 | -2 | 17 | 2 | 117 | 99 | 12 |
| -2 | 12 | 0 | 77 | 5 | 43 | 1 | 5 | 1 | 143 | 120 | 6 | -1 | 17 | 1 | 110 | 82 | 42 | -1 | 17 | 2 | 157 | 148 | 14 |
| 0 | 12 | 0 | 97 | 83 | 21 | 2 | 5 | 1 | 624 | 673 | 16 | 0 | 17 | 1 | 175 | 123 | 10 | 0 | 17 | 2 | 64 | 71 | 21 |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 2 | 12 | 0 | 344 | 321 | 15 | 1 | 6 | 1 | 170 | 202 | 6 | 2 | 17 | 1 | 280 | 248 | 10 | 1 | 17 | 2 | 87 | 86 | 26 |
| 3 | 12 | 0 | 88 | 37 | 25 | 2 | 6 | 1 | 172 | 175 | 18 | 3 | 17 | 1 | 85 | 71 | 18 | 2 | 17 | 2 | 53 | 37 | 35 |
| 4 | 12 | 0 | 169 | 156 | 21 | 3 | 6 | 1 | 284 | 246 | 15 | -3 | 18 | 1 | 96 | 80 | 16 | 3 | 17 | 2 | 80 | 87 | 20 |
| -1 | 13 | 0 | 38 | 9 | 37 | -2 | 7 | 1 | 122 | 113 | 11 | -1 | 18 | 1 | 103 | 83 | 13 | -2 | 18 | 2 | 46 | 47 | 45 |
| 2 | 13 | 0 | 97 | 124 | 22 | -1 | 7 | 1 | 399 | 369 | 17 | 0 | 18 | 1 | 147 | 118 | 15 | -1 | 18 | 2 | 128 | 146 | 12 |
| 3 | 13 | 0 | 168 | 188 | 18 | 0 | 7 | 1 | 317 | 373 | 10 | 1 | 18 | 1 | 236 | 218 | 10 | 0 | 18 | 2 | 161 | 73 | 48 |
| 4 | 13 | 0 | 88 | 4 | 40 | 1 | 7 | 1 | 185 | 170 | 7 | 2 | 18 | 1 | 119 | 118 | 24 | 1 | 18 | 2 | 153 | 126 | 16 |
| 0 | 14 | 0 | 105 | 104 | 19 | 2 | 7 | 1 | 313 | 372 | 9 | 3 | 18 | 1 | 66 | 83 | 22 | 2 | 18 | 2 | 74 | 73 | 35 |
| 1 | 14 | 0 | 164 | 161 | 11 | 3 | 7 | 1 | 368 | 369 | 28 | -4 | 19 | 1 | 46 | 80 | 46 | 3 | 18 | 2 | 156 | 145 | 13 |
| 2 | 14 | 0 | 123 | 93 | 11 | -3 | 8 | 1 | 128 | 112 | 17 | -3 | 19 | 1 | 75 | 77 | 21 | -3 | 19 | 2 | 51 | 46 | 50 |
| 3 | 14 | 0 | 89 | 139 | 27 | -2 | 8 | 1 | 146 | 100 | 24 | -2 | 19 | 1 | 115 | 124 | 11 | -2 | 19 | 2 | 20 | 9 | 20 |
| 4 | 14 | 0 | 0 | 50 | 1 | -1 | 8 | 1 | 116 | 91 | 19 | -1 | 19 | 1 | 103 | 120 | 19 | -1 | 19 | 2 | 157 | 149 | 18 |
| 1 | 15 | 0 | 83 | 60 | 30 | 0 | 8 | 1 | 104 | 93 | 13 | 0 | 19 | 1 | 175 | 179 | 11 | 0 | 19 | 2 | 143 | 167 | 14 |
| 2 | 15 | 0 | 248 | 227 | 10 | 1 | 8 | 1 | 196 | 223 | 11 | 1 | 19 | 1 | 75 | 120 | 28 | 1 | 19 | 2 | 109 | 68 | 20 |
| 3 | 15 | 0 | 283 | 273 | 15 | 2 | 8 | 1 | 115 | 77 | 14 | 2 | 19 | 1 | 118 | 124 | 11 | 2 | 19 | 2 | 119 | 167 | 16 |
| 0 | 16 | 0 | 77 | 26 | 25 | 3 | 8 | 1 | 194 | 222 | 13 | 3 | 19 | 1 | 49 | 77 | 48 | 3 | 19 | 2 | 160 | 149 | 17 |
| 1 | 16 | 0 | 40 | 24 | 40 | -2 | 9 | 1 | 107 | 92 | 12 | -2 | 20 | 1 | 215 | 209 | 11 | -2 | 20 | 2 | 55 | 9 | 41 |
| 2 | 16 | 0 | 63 | 39 | 23 | -1 | 9 | 1 | 135 | 91 | 12 | -1 | 20 | 1 | 64 | 54 | 32 | -1 | 20 | 2 | 98 | 96 | 13 |
| 3 | 16 | 0 | 62 | 93 | 61 | 0 | 9 | 1 | 101 | 62 | 36 | 0 | 20 | 1 | 69 | 84 | 27 | 0 | 20 | 2 | 0 | 92 | 1 |
| -1 | 17 | 0 | 50 | 8 | 50 | 1 | 9 | 1 | 114 | 91 | 17 | 1 | 20 | 1 | 0 | 54 | 1 | 1 | 20 | 2 | 71 | 19 | 42 |
| 1 | 17 | 0 | 58 | 46 | 57 | -3 | 10 | 1 | 122 | 115 | 16 | 2 | 20 | 1 | 207 | 209 | 14 | 2 | 20 | 2 | 45 | 93 | 45 |
| 2 | 17 | 0 | 114 | 143 | 14 | -2 | 10 | 1 | 522 | 569 | 22 | -2 | 21 | 1 | 0 | 24 | 1 | -1 | 21 | 2 | 104 | 96 | 28 |
| 3 | 17 | 0 | 100 | 100 | 25 | -1 | 10 | 1 | 556 | 610 | 16 | -1 | 21 | 1 | 77 | 97 | 21 | 0 | 21 | 2 | 112 | 116 | 19 |
| 0 | 18 | 0 | 122 | 122 | 27 | 0 | 10 | 1 | 513 | 570 | 22 | 0 | 21 | 1 | 155 | 180 | 11 | 1 | 21 | 2 | 0 | 31 | 1 |
| 1 | 18 | 0 | 46 | 44 | 29 | 1 | 10 | 1 | 126 | 116 | 11 | 1 | 21 | 1 | 83 | 97 | 19 | 2 | 21 | 2 | 64 | 29 | 31 |
| 2 | 18 | 0 | 65 | 21 | 37 | -4 | 11 | 1 | 79 | 92 | 30 | -4 | 22 | 1 | 42 | 25 | 42 | -1 | 22 | 2 | 0 | 31 | 1 |
| 3 | 18 | 0 | 67 | 82 | 34 | -3 | 11 | 1 | 132 | 78 | 27 | -3 | 22 | 1 | 72 | 95 | 22 | 0 | 22 | 2 | 127 | 116 | 17 |
| -1 | 19 | 0 | 67 | 77 | 15 | -2 | 11 | 1 | 195 | 194 | 19 | -2 | 22 | 1 | 130 | 155 | 15 | 1 | 22 | 2 | 93 | 47 | 38 |
| 2 | 19 | 0 | 86 | 9 | 43 | -1 | 11 | 1 | 262 | 248 | 10 | -1 | 22 | 1 | 137 | 102 | 14 | 2 | 22 | 2 | 50 | 67 | 43 |
| 3 | 19 | 0 | 44 | 199 | 19 | 0 | 11 | 1 | 375 | 400 | 14 | 0 | 22 | 1 | 54 | 55 | 54 | -1 | 23 | 2 | 171 | 153 | 11 |
| 0 | 20 | 0 | 188 | 0 | 1 | 1 | 11 | 1 | 690 | 690 | 21 | 1 | 22 | 1 | 0 | 55 | 1 | 0 | 23 | 2 | 40 | 67 | 40 |
| 1 | 20 | 0 | 0 | 42 | 1 | -3 | 12 | 1 | 375 | 401 | 14 | -3 | 23 | 1 | 120 | 133 | 12 | 1 | 23 | 2 | 73 | 67 | 20 |
| 2 | 20 | 0 | 154 | 143 | 15 | -2 | 12 | 1 | 264 | 247 | 10 | -2 | 23 | 1 | 100 | 89 | 17 | 2 | 23 | 2 | 56 | 89 | 56 |
| 3 | 20 | 0 | 54 | 48 | 41 | -1 | 12 | 1 | 197 | 193 | 10 | -1 | 23 | 1 | 93 | 133 | 21 | 0 | 0 | 3 | 77 | 68 | 23 |
| 1 | 21 | 0 | 138 | 110 | 30 | 0 | 12 | 1 | 35 | 51 | 16 | 0 | 23 | 1 | 73 | 28 | 65 | 1 | 0 | 3 | 1331 | 1063 | 37 |
| 2 | 21 | 0 | 127 | 96 | 19 | 1 | 12 | 1 | 50 | 25 | 8 | 1 | 23 | 1 | 730 | 648 | 22 | -1 | 1 | 3 | 191 | 167 | 10 |
| -1 | 22 | 0 | 46 | 3 | 46 | 2 | 12 | 1 | 328 | 299 | 14 | 0 | 0 | 2 | 696 | 652 | 18 | 0 | 1 | 3 | 0 | 15 | 1 |
| 0 | 22 | 0 | 0 | 4 | 1 | 3 | 12 | 1 | 242 | 239 | 12 | 1 | 0 | 2 | 545 | 482 | 23 | 1 | 1 | 3 | 61 | 39 | 38 |
| 1 | 22 | 0 | 56 | 47 | 55 | -3 | 13 | 1 | 128 | 104 | 13 | -1 | 1 | 2 | 143 | 121 | 18 | -1 | 2 | 3 | 113 | 112 | 17 |
| 2 | 22 | 0 | 273 | 277 | 9 | -2 | 13 | 1 | 247 | 240 | 10 | 0 | 1 | 2 | 158 | 104 | 14 | 0 | 2 | 3 | 63 | 76 | 63 |
| -1 | 23 | 0 | 277 | 257 | 12 | -1 | 13 | 1 | 156 | 130 | 16 | 1 | 1 | 2 | 120 | 115 | 17 | 1 | 2 | 3 | 55 | 99 | 54 |
| 0 | 23 | 0 | 883 | 766 | 31 | 0 | 13 | 1 | 131 | 124 | 8 | -1 | 2 | 2 | 609 | 605 | 21 | 2 | 2 | 3 | 79 | 106 | 78 |
| 1 | 23 | 0 | 237 | 298 | 5 | 1 | 13 | 1 | 353 | 357 | 14 | 0 | 2 | 2 | 1364 | 1149 | 59 | -2 | 3 | 3 | 0 | 34 | 1 |
| -2 | 0 | 1 | 46 | 6 | 46 | 2 | 13 | 1 | 308 | 330 | 12 | 1 | 2 | 2 | 258 | 251 | 18 | -1 | 3 | 3 | 60 | 3 | 38 |
| 0 | 0 | 1 | 2688 | 1939 | 125 | 3 | 13 | 1 | 368 | 355 | 13 | 2 | 2 | 2 | 124 | 63 | 36 | 0 | 3 | 3 | 113 | 112 | 17 |
| 1 | 0 | 1 | 881 | 767 | 54 | -3 | 14 | 1 | 130 | 124 | 18 | -2 | 3 | 2 | 85 | 25 | 72 | 1 | 3 | 3 | 63 | 76 | 63 |
| 2 | 0 | 1 | 55 | 76 | 55 | -2 | 14 | 1 | 172 | 130 | 19 | -1 | 3 | 2 | 155 | 142 | 14 | 2 | 3 | 3 | 54 | 28 | 54 |
| -1 | 1 | 1 | 86 | 112 | 73 | -1 | 14 | 1 | 123 | 118 | 15 | 0 | 3 | 2 | 183 | 177 | 26 | 3 | 3 | 3 | 52 | 34 | 50 |
| 0 | 1 | 1 | 193 | 185 | 13 | 0 | 14 | 1 | 108 | 23 | 28 | 1 | 3 | 2 | 330 | 312 | 10 | -3 | 2 | 3 | 0 | 63 | 1 |
| -3 | 2 | 1 | 158 | 182 | 30 | | | | | | | 2 | 3 | 2 | 1251 | 1117 | 36 | -2 | 2 | 3 | 92 | 29 | 31 |
| -2 | 2 | 1 | 709 | 661 | 24 | | | | | | | | | | | | | 1 | 5 | 3 | 1538 | 1300 | 53 |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| -1 | 2 | 3 | 718 | 720 | 18 | 0 | 1 | 4 | 148 | 164 | 5 | -2 | 11 | 4 | 129 | 128 | 9 | 2 | 0 | 5 | 212 | 190 | 16 |
| 0 | 2 | 3 | 861 | 785 | 21 | 1 | 1 | 4 | 1211 | 1116 | 37 | -1 | 11 | 4 | 639 | 621 | 22 | 3 | 0 | 5 | 110 | 101 | 16 |
| 1 | 2 | 3 | 688 | 719 | 21 | 2 | 1 | 4 | 309 | 311 | 23 | 0 | 11 | 4 | 366 | 378 | 14 | 4 | 0 | 5 | 50 | 70 | 50 |
| 2 | 2 | 3 | 682 | 660 | 45 | 3 | 1 | 4 | 186 | 177 | 7 | 1 | 11 | 4 | 633 | 621 | 28 | -4 | 1 | 5 | 94 | 60 | 51 |
| 3 | 2 | 3 | 189 | 182 | 23 | 4 | 1 | 4 | 147 | 142 | 30 | 2 | 11 | 4 | 127 | 129 | 10 | -3 | 1 | 5 | 166 | 162 | 22 |
| 4 | 2 | 3 | 163 | 185 | 30 | -4 | 2 | 4 | 91 | 65 | 21 | 3 | 11 | 4 | 169 | 167 | 14 | -2 | 1 | 5 | 184 | 163 | 9 |
| -4 | 3 | 3 | 30 | 73 | 30 | -3 | 2 | 4 | 24 | 55 | 24 | -3 | 12 | 4 | 76 | 84 | 26 | -1 | 1 | 5 | 353 | 405 | 11 |
| -3 | 3 | 3 | 270 | 222 | 17 | -2 | 2 | 4 | 502 | 497 | 17 | -2 | 12 | 4 | 126 | 129 | 25 | 0 | 1 | 5 | 353 | 405 | 9 |
| -2 | 3 | 3 | 431 | 447 | 21 | -1 | 2 | 4 | 1553 | 1343 | 44 | -1 | 12 | 4 | 157 | 174 | 13 | 1 | 1 | 5 | 160 | 164 | 18 |
| -1 | 3 | 3 | 824 | 853 | 29 | 0 | 2 | 4 | 912 | 866 | 24 | 0 | 12 | 4 | 174 | 162 | 9 | 2 | 1 | 5 | 177 | 162 | 7 |
| 0 | 3 | 3 | 12 | 22 | 12 | 1 | 2 | 4 | 1484 | 1343 | 47 | 1 | 12 | 4 | 247 | 267 | 11 | 3 | 1 | 5 | 57 | 60 | 56 |
| 1 | 3 | 3 | 845 | 854 | 22 | 2 | 2 | 4 | 440 | 497 | 34 | 2 | 12 | 4 | 0 | 15 | 1 | 4 | 1 | 5 | 239 | 234 | 21 |
| 2 | 3 | 3 | 369 | 448 | 30 | 3 | 2 | 4 | 33 | 55 | 33 | 3 | 12 | 4 | 259 | 267 | 20 | -4 | 2 | 5 | 226 | 219 | 25 |
| 3 | 3 | 3 | 261 | 223 | 16 | 4 | 2 | 4 | 0 | 65 | 1 | -3 | 13 | 4 | 177 | 162 | 9 | -3 | 2 | 5 | 545 | 510 | 18 |
| 4 | 3 | 3 | 0 | 72 | 1 | -4 | 3 | 4 | 175 | 159 | 14 | -2 | 13 | 4 | 150 | 175 | 17 | -2 | 2 | 5 | 827 | 843 | 50 |
| -4 | 4 | 3 | 167 | 219 | 28 | -3 | 3 | 4 | 197 | 181 | 27 | -1 | 13 | 4 | 137 | 129 | 15 | -1 | 2 | 5 | 539 | 558 | 14 |
| -3 | 4 | 3 | 427 | 405 | 17 | -2 | 3 | 4 | 147 | 125 | 7 | 0 | 13 | 4 | 126 | 148 | 29 | 0 | 2 | 5 | 821 | 843 | 25 |
| -2 | 4 | 3 | 285 | 265 | 11 | -1 | 3 | 4 | 580 | 609 | 24 | 1 | 13 | 4 | 66 | 64 | 32 | 1 | 2 | 5 | 501 | 510 | 36 |
| -1 | 4 | 3 | 655 | 695 | 22 | 0 | 3 | 4 | 1479 | 1230 | 40 | 2 | 13 | 4 | 231 | 228 | 9 | 2 | 2 | 5 | 217 | 219 | 10 |
| 0 | 4 | 3 | 745 | 728 | 20 | 1 | 3 | 4 | 569 | 608 | 15 | 3 | 13 | 4 | 204 | 186 | 11 | 3 | 2 | 5 | 199 | 234 | 29 |
| 1 | 4 | 3 | 643 | 694 | 17 | 2 | 3 | 4 | 117 | 125 | 20 | -3 | 14 | 4 | 183 | 142 | 13 | 4 | 2 | 5 | 194 | 196 | 15 |
| 2 | 4 | 3 | 255 | 266 | 21 | 3 | 3 | 4 | 201 | 181 | 10 | -2 | 14 | 4 | 202 | 185 | 8 | -4 | 3 | 5 | 0 | 25 | 1 |
| 3 | 4 | 3 | 430 | 406 | 16 | 4 | 3 | 4 | 140 | 160 | 34 | -1 | 14 | 4 | 257 | 228 | 7 | -3 | 3 | 5 | 377 | 386 | 22 |
| -4 | 5 | 3 | 197 | 219 | 24 | -4 | 4 | 4 | 25 | 49 | 25 | 0 | 14 | 4 | 64 | 65 | 43 | -2 | 3 | 5 | 297 | 351 | 14 |
| -3 | 5 | 3 | 93 | 140 | 53 | -3 | 4 | 4 | 247 | 224 | 14 | 1 | 14 | 4 | 171 | 148 | 14 | -1 | 3 | 5 | 232 | 241 | 7 |
| -2 | 5 | 3 | 296 | 252 | 19 | -2 | 4 | 4 | 282 | 307 | 13 | 2 | 14 | 4 | 80 | 97 | 54 | 0 | 3 | 5 | 300 | 352 | 13 |
| -1 | 5 | 3 | 65 | 54 | 16 | -1 | 4 | 4 | 566 | 591 | 19 | -3 | 15 | 4 | 100 | 85 | 17 | 1 | 3 | 5 | 342 | 384 | 25 |
| 0 | 5 | 3 | 623 | 686 | 16 | 0 | 4 | 4 | 249 | 269 | 7 | -2 | 15 | 4 | 190 | 201 | 10 | 2 | 3 | 5 | 42 | 25 | 41 |
| 1 | 5 | 3 | 360 | 383 | 11 | 1 | 4 | 4 | 551 | 591 | 15 | -1 | 15 | 4 | 277 | 261 | 10 | 3 | 3 | 5 | 209 | 195 | 25 |
| 2 | 5 | 3 | 350 | 407 | 16 | 2 | 4 | 4 | 264 | 307 | 21 | 0 | 15 | 4 | 0 | 25 | 1 | 4 | 3 | 5 | 88 | 99 | 27 |
| 3 | 5 | 3 | 308 | 362 | 8 | 3 | 4 | 4 | 261 | 224 | 11 | 1 | 15 | 4 | 286 | 262 | 17 | -4 | 4 | 5 | 231 | 244 | 30 |
| -4 | 6 | 3 | 620 | 635 | 16 | 4 | 4 | 4 | 59 | 48 | 59 | 2 | 15 | 4 | 187 | 200 | 9 | -3 | 4 | 5 | 246 | 225 | 12 |
| -3 | 6 | 3 | 0 | 55 | 1 | -4 | 5 | 4 | 131 | 93 | 13 | -2 | 16 | 4 | 69 | 84 | 34 | -2 | 4 | 5 | 204 | 241 | 7 |
| -2 | 6 | 3 | 288 | 252 | 13 | -3 | 5 | 4 | 192 | 167 | 12 | -1 | 16 | 4 | 76 | 97 | 22 | -1 | 4 | 5 | 518 | 540 | 16 |
| -1 | 6 | 3 | 88 | 140 | 64 | -2 | 5 | 4 | 285 | 263 | 13 | 0 | 16 | 4 | 66 | 55 | 44 | 0 | 4 | 5 | 207 | 242 | 6 |
| 0 | 6 | 3 | 105 | 78 | 32 | -1 | 5 | 4 | 129 | 136 | 8 | 1 | 16 | 4 | 365 | 355 | 12 | 1 | 4 | 5 | 242 | 225 | 18 |
| 1 | 6 | 3 | 328 | 334 | 12 | 0 | 5 | 4 | 165 | 169 | 7 | 2 | 16 | 4 | 170 | 143 | 19 | 2 | 4 | 5 | 269 | 244 | 11 |
| 2 | 6 | 3 | 443 | 439 | 20 | 1 | 5 | 4 | 140 | 137 | 5 | -2 | 17 | 4 | 163 | 141 | 8 | 3 | 4 | 5 | 75 | 100 | 75 |
| 3 | 6 | 3 | 306 | 362 | 15 | 2 | 5 | 4 | 255 | 262 | 22 | -1 | 17 | 4 | 145 | 142 | 12 | 4 | 4 | 5 | 150 | 147 | 14 |
| -3 | 7 | 3 | 350 | 407 | 15 | 3 | 5 | 4 | 200 | 168 | 11 | 0 | 17 | 4 | 374 | 356 | 13 | -4 | 5 | 5 | 68 | 52 | 19 |
| -2 | 7 | 3 | 449 | 440 | 28 | 4 | 5 | 4 | 77 | 48 | 77 | 1 | 17 | 4 | 36 | 55 | 36 | -3 | 5 | 5 | 141 | 109 | 10 |
| -1 | 7 | 3 | 331 | 334 | 13 | -4 | 6 | 4 | 128 | 89 | 33 | -2 | 18 | 4 | 104 | 97 | 17 | -2 | 5 | 5 | 58 | 69 | 11 |
| 0 | 7 | 3 | 0 | 78 | 1 | -3 | 6 | 4 | 211 | 179 | 11 | -1 | 18 | 4 | 222 | 202 | 9 | -1 | 5 | 5 | 356 | 366 | 11 |
| 1 | 7 | 3 | 144 | 112 | 24 | -2 | 6 | 4 | 568 | 553 | 37 | 0 | 18 | 4 | 192 | 188 | 15 | 0 | 5 | 5 | 63 | 68 | 8 |
| 2 | 7 | 3 | 143 | 125 | 15 | -1 | 6 | 4 | 195 | 211 | 19 | 1 | 18 | 4 | 134 | 150 | 9 | 1 | 5 | 5 | 120 | 109 | 23 |
| -3 | 8 | 3 | 283 | 250 | 17 | 0 | 6 | 4 | 616 | 607 | 18 | -2 | 19 | 4 | 186 | 188 | 14 | -3 | 6 | 5 | 70 | 52 | 38 |
| -2 | 8 | 3 | 322 | 398 | 11 | 1 | 6 | 4 | 196 | 210 | 6 | -1 | 19 | 4 | 231 | 203 | 10 | -2 | 6 | 5 | 130 | 148 | 35 |
| -1 | 8 | 3 | 0 | 13 | 1 | 2 | 6 | 4 | 578 | 553 | 35 | 0 | 19 | 4 | 56 | 97 | 48 | -1 | 6 | 5 | 159 | 142 | 15 |
| 0 | 8 | 3 | 315 | 397 | 9 | 3 | 6 | 4 | 177 | 179 | 12 | 1 | 19 | 4 | 44 | 71 | 44 | 2 | 6 | 5 | 294 | 243 | 11 |
| 1 | 8 | 3 | 269 | 251 | 21 | | | | | | | | | | | | | | | | | | |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 3 | 7 | 3 | 136 | 125 | 12 | -1 | 18 | 3 | 196 | 135 | 19 | 4 | 6 | 4 | 69 | 89 | 68 | -2 | 6 | 5 | 127 | 109 | 11 | -2 | 6 | 7 | 340 | 329 | 18 |
| -4 | 8 | 3 | 111 | 95 | 32 | 0 | 18 | 3 | 0 | 17 | 1 | -4 | 7 | 4 | 81 | 88 | 28 | -1 | 7 | 5 | 233 | 230 | 15 | -1 | 6 | 7 | 562 | 622 | 22 |
| -3 | 8 | 3 | 219 | 191 | 11 | 1 | 18 | 3 | 145 | 135 | 21 | -3 | 7 | 4 | 184 | 153 | 9 | 0 | 7 | 5 | 231 | 204 | 14 | 0 | 6 | 7 | 941 | 879 | 28 |
| -2 | 8 | 3 | 284 | 259 | 14 | 2 | 18 | 3 | 54 | 73 | 54 | -2 | 7 | 4 | 205 | 180 | 11 | 1 | 7 | 5 | 243 | 230 | 12 | 1 | 6 | 7 | 569 | 622 | 15 |
| -1 | 8 | 3 | 169 | 174 | 16 | -1 | 19 | 3 | 178 | 170 | 11 | -1 | 7 | 4 | 311 | 377 | 19 | 2 | 7 | 5 | 114 | 109 | 51 | 2 | 6 | 7 | 351 | 329 | 23 |
| 0 | 8 | 3 | 56 | 67 | 9 | 0 | 19 | 3 | 27 | 63 | 26 | 0 | 7 | 4 | 179 | 176 | 7 | -3 | 8 | 5 | 51 | 72 | 36 | -3 | 7 | 7 | 263 | 243 | 13 |
| 1 | 8 | 3 | 156 | 174 | 6 | 1 | 19 | 3 | 91 | 52 | 25 | 1 | 7 | 4 | 318 | 376 | 8 | -2 | 8 | 5 | 126 | 120 | 16 | -2 | 7 | 7 | 127 | 142 | 38 |
| 2 | 8 | 3 | 293 | 259 | 21 | 2 | 19 | 3 | 180 | 152 | 20 | 2 | 7 | 4 | 177 | 181 | 22 | -1 | 8 | 5 | 88 | 68 | 8 | -1 | 7 | 7 | 122 | 137 | 16 |
| 3 | 8 | 3 | 207 | 191 | 10 | 3 | 19 | 3 | 86 | 24 | 20 | 3 | 7 | 4 | 173 | 152 | 44 | 0 | 8 | 5 | 350 | 341 | 17 | 0 | 7 | 7 | 297 | 305 | 13 |
| -4 | 9 | 3 | 138 | 95 | 25 | -1 | 19 | 3 | 154 | 153 | 14 | -4 | 8 | 4 | 71 | 32 | 71 | 1 | 8 | 5 | 337 | 341 | 19 | 1 | 7 | 7 | 71 | 64 | 20 |
| -3 | 9 | 3 | 157 | 129 | 24 | 2 | 19 | 3 | 80 | 52 | 27 | -3 | 8 | 4 | 116 | 106 | 17 | 2 | 8 | 5 | 38 | 68 | 18 | 2 | 7 | 7 | 376 | 436 | 24 |
| -2 | 9 | 3 | 83 | 76 | 32 | -2 | 19 | 3 | 78 | 63 | 18 | -2 | 8 | 4 | 83 | 58 | 37 | -3 | 9 | 5 | 120 | 68 | 37 | -3 | 8 | 7 | 389 | 456 | 14 |
| -1 | 9 | 3 | 117 | 95 | 13 | -1 | 20 | 3 | 74 | 55 | 17 | -1 | 8 | 4 | 258 | 239 | 18 | -2 | 9 | 5 | 64 | 37 | 14 | -2 | 8 | 7 | 394 | 436 | 11 |
| 0 | 9 | 3 | 442 | 456 | 15 | 0 | 20 | 3 | 102 | 102 | 21 | 0 | 8 | 4 | 145 | 138 | 10 | -1 | 9 | 5 | 85 | 89 | 16 | -1 | 8 | 7 | 64 | 65 | 64 |
| 1 | 9 | 3 | 61 | 69 | 16 | 1 | 20 | 3 | 108 | 69 | 31 | 1 | 8 | 4 | 259 | 238 | 11 | 0 | 9 | 5 | 151 | 158 | 13 | 0 | 8 | 7 | 312 | 305 | 13 |
| 2 | 9 | 3 | 440 | 457 | 17 | 2 | 20 | 3 | 83 | 102 | 19 | 2 | 8 | 4 | 64 | 58 | 63 | 1 | 9 | 5 | 342 | 328 | 16 | 1 | 8 | 7 | 132 | 137 | 34 |
| -1 | 9 | 3 | 110 | 94 | 31 | -2 | 20 | 3 | 74 | 54 | 74 | 3 | 8 | 4 | 82 | 105 | 23 | 2 | 9 | 5 | 146 | 158 | 13 | 2 | 8 | 7 | 71 | 47 | 27 |
| 0 | 9 | 3 | 109 | 77 | 18 | -1 | 20 | 3 | 77 | 50 | 27 | -4 | 9 | 4 | 0 | 32 | 1 | -3 | 10 | 5 | 112 | 88 | 16 | -3 | 9 | 7 | 111 | 96 | 17 |
| -4 | 10 | 3 | 161 | 129 | 23 | 0 | 20 | 3 | 101 | 115 | 21 | -3 | 9 | 4 | 61 | 70 | 60 | -2 | 10 | 5 | 68 | 36 | 18 | -2 | 9 | 7 | 167 | 148 | 14 |
| -3 | 10 | 3 | 77 | 59 | 64 | -1 | 21 | 3 | 334 | 357 | 17 | -2 | 9 | 4 | 118 | 111 | 17 | -1 | 10 | 5 | 130 | 122 | 10 | -1 | 9 | 7 | 335 | 365 | 21 |
| -2 | 10 | 3 | 195 | 187 | 14 | 0 | 21 | 3 | 86 | 116 | 12 | -1 | 9 | 4 | 141 | 100 | 12 | 0 | 10 | 5 | 110 | 103 | 16 | 0 | 9 | 7 | 532 | 614 | 16 |
| -1 | 10 | 3 | 244 | 211 | 8 | 1 | 21 | 3 | 94 | 51 | 19 | 0 | 9 | 4 | 259 | 237 | 16 | 1 | 10 | 5 | 185 | 173 | 10 | 1 | 9 | 7 | 346 | 365 | 22 |
| 0 | 10 | 3 | 201 | 177 | 10 | -1 | 21 | 3 | 91 | 97 | 21 | 1 | 9 | 4 | 692 | 686 | 21 | 2 | 10 | 5 | 84 | 103 | 19 | 2 | 9 | 7 | 120 | 148 | 30 |
| 1 | 10 | 3 | 74 | 69 | 14 | 0 | 21 | 3 | 154 | 148 | 12 | 2 | 9 | 4 | 253 | 238 | 20 | -3 | 11 | 5 | 105 | 121 | 20 | -3 | 10 | 7 | 95 | 96 | 19 |
| 2 | 10 | 3 | 197 | 178 | 10 | 2 | 21 | 3 | 72 | 97 | 25 | 3 | 9 | 4 | 136 | 100 | 12 | -2 | 11 | 5 | 98 | 100 | 11 | -2 | 10 | 7 | 44 | 48 | 44 |
| -1 | 10 | 3 | 245 | 211 | 9 | -1 | 22 | 3 | 133 | 39 | 26 | -4 | 10 | 4 | 127 | 110 | 25 | -1 | 11 | 5 | 222 | 213 | 15 | -1 | 10 | 7 | 80 | 68 | 69 |
| 0 | 10 | 3 | 183 | 188 | 56 | 0 | 22 | 3 | 107 | 109 | 19 | -3 | 10 | 4 | 103 | 69 | 36 | 0 | 11 | 5 | 157 | 165 | 11 | 0 | 10 | 7 | 90 | 87 | 23 |
| -4 | 11 | 3 | 95 | 59 | 14 | 1 | 22 | 3 | 85 | 21 | 50 | -2 | 10 | 4 | 83 | 68 | 50 | 1 | 11 | 5 | 212 | 213 | 29 | 1 | 10 | 7 | 200 | 164 | 9 |
| -3 | 11 | 3 | 123 | 119 | 23 | 0 | 22 | 3 | 111 | 109 | 1 | -1 | 10 | 4 | 84 | 75 | 25 | -1 | 12 | 5 | 72 | 78 | 39 | 2 | 10 | 7 | 101 | 96 | 12 |
| -2 | 11 | 3 | 428 | 468 | 10 | 0 | 22 | 3 | 53 | 77 | 52 | 0 | 10 | 4 | 61 | 34 | 21 | 0 | 12 | 5 | 65 | 69 | 19 | -1 | 11 | 7 | 153 | 138 | 12 |
| -1 | 11 | 3 | 67 | 98 | 13 | 1 | 22 | 3 | 185 | 163 | 23 | 1 | 10 | 4 | 168 | 155 | 40 | 1 | 12 | 5 | 606 | 588 | 23 | 0 | 11 | 7 | 606 | 588 | 24 |
| 0 | 11 | 3 | 170 | 165 | 19 | 2 | 22 | 3 | 64 | 67 | 17 | 2 | 10 | 4 | 93 | 83 | 18 | 2 | 12 | 5 | 39 | 20 | 38 | 1 | 11 | 7 | 193 | 157 | 20 |
| 1 | 11 | 3 | 214 | 214 | 20 | -1 | 22 | 3 | 117 | 88 | 22 | -4 | 11 | 4 | 148 | 142 | 23 | -1 | 12 | 5 | 64 | 69 | 28 | -1 | 12 | 7 | 203 | 187 | 12 |
| 2 | 11 | 3 | 84 | 116 | 50 | 0 | 22 | 3 | 86 | 21 | 26 | -3 | 11 | 4 | 334 | 327 | 10 | 0 | 12 | 5 | 77 | 78 | 26 | 0 | 12 | 7 | 81 | 59 | 18 |
| -1 | 11 | 3 | 103 | 106 | 9 | 1 | 22 | 3 | 96 | 89 | 22 | -2 | 11 | 4 | 429 | 454 | 50 | 1 | 12 | 5 | 38 | 48 | 37 | 1 | 12 | 7 | 206 | 236 | 18 |
| 0 | 11 | 3 | 95 | 79 | 6 | 2 | 22 | 3 | 50 | 67 | 49 | -1 | 11 | 4 | 210 | 205 | 19 | 2 | 12 | 5 | 165 | 177 | 20 | 2 | 12 | 7 | 77 | 68 | 35 |
| -4 | 11 | 3 | 87 | 107 | 16 | -1 | 22 | 3 | 50 | 2 | 50 | 0 | 11 | 4 | 442 | 455 | 27 | -1 | 13 | 5 | 157 | 28 | 13 | -1 | 12 | 7 | 170 | 164 | 7 |
| -3 | 11 | 3 | 136 | 116 | 23 | 0 | 0 | 4 | 0 | 26 | 11 | 1 | 11 | 4 | 348 | 326 | 13 | 0 | 13 | 5 | 36 | 47 | 36 | 0 | 13 | 7 | 554 | 575 | 20 |
| -2 | 11 | 3 | 213 | 215 | 10 | -1 | 0 | 4 | 12 | 2 | 36 | 2 | 11 | 4 | 167 | 143 | 15 | 1 | 13 | 5 | 149 | 175 | 11 | 1 | 13 | 7 | 192 | 205 | 8 |
| -1 | 11 | 3 | 143 | 156 | 9 | 1 | 0 | 4 | 122 | 106 | 10 | -4 | 12 | 4 | 98 | 83 | 38 | -1 | 13 | 5 | 0 | 5 | 1 | 2 | 13 | 7 | 582 | 575 | 24 |
| 0 | 11 | 3 | 214 | 216 | 10 | 0 | 0 | 4 | 0 | 23 | 10 | -3 | 12 | 4 | 89 | 78 | 15 | 0 | 13 | 5 | 172 | 175 | 12 | -1 | 13 | 7 | 171 | 158 | 12 |
| 1 | 11 | 3 | 103 | 106 | 23 | 1 | 0 | 4 | 121 | 105 | 14 | -2 | 12 | 4 | 34 | 37 | 34 | 1 | 13 | 5 | 73 | 67 | 37 | 0 | 13 | 7 | 106 | 96 | 18 |
| 2 | 11 | 3 | 95 | 79 | 6 | 0 | 0 | 4 | 129 | 145 | 8 | -1 | 12 | 4 | 139 | 145 | 8 | -1 | 14 | 5 | 92 | 91 | 24 | 1 | 13 | 7 | 248 | 236 | 12 |
| -4 | 11 | 3 | 123 | 119 | 6 | -1 | 0 | 4 | 172 | 176 | 16 | 0 | 12 | 4 | 260 | 235 | 15 | 0 | 14 | 5 | 65 | 67 | 29 | 2 | 13 | 7 | 113 | 124 | 24 |
| -3 | 11 | 3 | 264 | 252 | 9 | 0 | 0 | 4 | 0 | 14 | 11 | 1 | 12 | 4 | 210 | 205 | 20 | 1 | 14 | 5 | 452 | 500 | 15 | -1 | 14 | 7 | 149 | 142 | 12 |
| -2 | 11 | 3 | 162 | 141 | 12 | 1 | 0 | 4 | 99 | 89 | 29 | 2 | 12 | 4 | 44 | 38 | 43 | 2 | 14 | 5 | 124 | 86 | 17 | 0 | 14 | 7 | 145 | 147 | 14 |
| 0 | 11 | 3 | 0 | 7 | 9 | 2 | 0 | 4 | 30 | 38 | 78 | -1 | 13 | 4 | 85 | 78 | 20 | -1 | 14 | 5 | 0 | 17 | 1 | 1 | 14 | 7 | 382 | 391 | 16 |
| 1 | 11 | 5 | 156 | 141 | 13 | -3 | 0 | 4 | 79 | 50 | 28 | 0 | 13 | 4 | 251 | 245 | 28 | 0 | 14 | 5 | 0 | 55 | 1 | -1 | 1 | 7 | 440 | 419 | 16 |
|   |   |   |     |     |    |   |   |   |     |     |    |   |   |   |     |     |    |   |   |   |     |    |   | 0 | 14 | 7 | 396 | 390 | 17 |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|
| 2 | 11 | 5 | 272 | 253 | 13 | -4 | 11 | 6 | 103 | 83 | 23 | 2 | 10 | 7 | 141 | 147 | 14 |
| 3 | 11 | 5 | 0 | 26 | 1 | -3 | 11 | 6 | 78 | 87 | 59 | 3 | 10 | 7 | 175 | 141 | 14 |
| 4 | 11 | 5 | 0 | 47 | 1 | -2 | 11 | 6 | 238 | 221 | 8 | 4 | 10 | 7 | 151 | 124 | 12 |
| -4 | 12 | 5 | 0 | 40 | 1 | -1 | 11 | 6 | 214 | 203 | 10 | -4 | 11 | 7 | 107 | 92 | 21 |
| -3 | 12 | 5 | 121 | 118 | 38 | 0 | 11 | 6 | 153 | 142 | 11 | -3 | 11 | 7 | 43 | 72 | 43 |
| -2 | 12 | 5 | 235 | 223 | 8 | 1 | 11 | 6 | 200 | 203 | 13 | -2 | 11 | 7 | 238 | 235 | 7 |
| -1 | 12 | 5 | 301 | 282 | 12 | 2 | 11 | 6 | 223 | 221 | 10 | -1 | 11 | 7 | 313 | 312 | 12 |
| 0 | 12 | 5 | 113 | 115 | 17 | 3 | 11 | 6 | 81 | 87 | 31 | 0 | 11 | 7 | 101 | 102 | 14 |
| 1 | 12 | 5 | 291 | 282 | 15 | -4 | 12 | 6 | 71 | 83 | 25 | 1 | 11 | 7 | 304 | 312 | 16 |
| 2 | 12 | 5 | 238 | 222 | 8 | -3 | 12 | 6 | 74 | 8 | 50 | 2 | 11 | 7 | 230 | 234 | 10 |
| 3 | 12 | 5 | 129 | 118 | 23 | -2 | 12 | 6 | 34 | 16 | 33 | 3 | 11 | 7 | 14 | 72 | 13 |
| -4 | 13 | 5 | 0 | 40 | 1 | -1 | 12 | 6 | 106 | 108 | 10 | -4 | 12 | 7 | 99 | 92 | 17 |
| -3 | 13 | 5 | 125 | 126 | 26 | 0 | 12 | 6 | 295 | 291 | 11 | -3 | 12 | 7 | 162 | 173 | 18 |
| -2 | 13 | 5 | 170 | 200 | 12 | 1 | 12 | 6 | 58 | 46 | 46 | -2 | 12 | 7 | 130 | 151 | 14 |
| -1 | 13 | 5 | 161 | 154 | 8 | 2 | 12 | 6 | 302 | 291 | 12 | -1 | 12 | 7 | 264 | 228 | 8 |
| 0 | 13 | 5 | 389 | 384 | 14 | 3 | 12 | 6 | 100 | 109 | 19 | 0 | 12 | 7 | 328 | 309 | 12 |
| 1 | 13 | 5 | 110 | 91 | 19 | -4 | 13 | 6 | 23 | 17 | 22 | 1 | 12 | 7 | 70 | 116 | 40 |
| 2 | 13 | 5 | 377 | 384 | 11 | -3 | 13 | 6 | 0 | 8 | 1 | 2 | 12 | 7 | 310 | 309 | 11 |
| 3 | 13 | 5 | 204 | 200 | 18 | -2 | 13 | 6 | 37 | 62 | 36 | 3 | 12 | 7 | 246 | 227 | 11 |
| 4 | 13 | 5 | 92 | 126 | 23 | -1 | 13 | 6 | 122 | 91 | 44 | -3 | 13 | 7 | 148 | 151 | 19 |
| -4 | 14 | 5 | 88 | 65 | 42 | 0 | 13 | 6 | 79 | 64 | 19 | -2 | 13 | 7 | 203 | 172 | 16 |
| -3 | 14 | 5 | 142 | 145 | 37 | 1 | 13 | 6 | 272 | 248 | 10 | -1 | 13 | 7 | 49 | 64 | 49 |
| -2 | 14 | 5 | 206 | 207 | 10 | 2 | 13 | 6 | 106 | 103 | 13 | 0 | 13 | 7 | 150 | 175 | 18 |
| -1 | 14 | 5 | 95 | 104 | 15 | 3 | 13 | 6 | 271 | 247 | 9 | 1 | 13 | 7 | 13 | 67 | 12 |
| 0 | 14 | 5 | 190 | 197 | 8 | -3 | 14 | 6 | 23 | 17 | 28 | 2 | 13 | 7 | 117 | 120 | 12 |
| 1 | 14 | 5 | 105 | 104 | 13 | -2 | 14 | 6 | 0 | 8 | 1 | 3 | 13 | 7 | 74 | 67 | 20 |
| 2 | 14 | 5 | 212 | 208 | 9 | -1 | 14 | 6 | 62 | 62 | 24 | -3 | 14 | 7 | 125 | 120 | 9 |
| 3 | 14 | 5 | 143 | 145 | 15 | 0 | 14 | 6 | 89 | 90 | 25 | -2 | 14 | 7 | 43 | 67 | 42 |
| -3 | 15 | 5 | 73 | 65 | 28 | 1 | 14 | 6 | 74 | 62 | 28 | -1 | 14 | 7 | 173 | 175 | 13 |
| -2 | 15 | 5 | 18 | 60 | 17 | 2 | 14 | 6 | 234 | 298 | 26 | 0 | 14 | 7 | 88 | 65 | 22 |
| -1 | 15 | 5 | 288 | 249 | 11 | 3 | 14 | 6 | 183 | 161 | 13 | 1 | 14 | 7 | 74 | 42 | 25 |
| 0 | 15 | 5 | 170 | 151 | 12 | -3 | 15 | 6 | 0 | 40 | 1 | 2 | 14 | 7 | 48 | 68 | 47 |
| 1 | 15 | 5 | 143 | 134 | 9 | -2 | 15 | 6 | 184 | 178 | 8 | -3 | 15 | 7 | 287 | 284 | 10 |
| 2 | 15 | 5 | 175 | 151 | 10 | -1 | 15 | 6 | 64 | 39 | 23 | -2 | 15 | 7 | 102 | 96 | 11 |
| 3 | 15 | 5 | 32 | 249 | 14 | 0 | 15 | 6 | 165 | 161 | 11 | -1 | 15 | 7 | 293 | 285 | 10 |
| -2 | 16 | 5 | 300 | 249 | 38 | 1 | 15 | 6 | 255 | 298 | 14 | 0 | 15 | 7 | 0 | 68 | 1 |
| -1 | 16 | 5 | 54 | 60 | 22 | 2 | 15 | 6 | 103 | 110 | 18 | 1 | 15 | 7 | 53 | 42 | 53 |
| 0 | 16 | 5 | 111 | 66 | 34 | 3 | 15 | 6 | 168 | 159 | 9 | -3 | 16 | 7 | 216 | 234 | 59 |
| 1 | 16 | 5 | 394 | 383 | 13 | -3 | 16 | 6 | 156 | 148 | 12 | -2 | 16 | 7 | 265 | 246 | 9 |
| 2 | 16 | 5 | 85 | 65 | 13 | -2 | 16 | 6 | 137 | 133 | 9 | -1 | 16 | 7 | 100 | 102 | 17 |
| -2 | 16 | 5 | 154 | 169 | 22 | -1 | 16 | 6 | 151 | 149 | 15 | 0 | 16 | 7 | 35 | 43 | 35 |
| -1 | 17 | 5 | 207 | 189 | 35 | 0 | 16 | 6 | 180 | 159 | 14 | 1 | 16 | 7 | 96 | 101 | 15 |
| 0 | 17 | 5 | 151 | 161 | 9 | 1 | 16 | 6 | 113 | 110 | 14 | -2 | 17 | 7 | 259 | 234 | 21 |
| 1 | 17 | 5 | 212 | 195 | 16 | 2 | 16 | 6 | 68 | 55 | 30 | -1 | 17 | 7 | 221 | 246 | 10 |
| -2 | 17 | 5 | 212 | 195 | 12 | -2 | 17 | 6 | 233 | 208 | 10 | 0 | 17 | 7 | 120 | 102 | 15 |
| 0 | 17 | 5 | 149 | 161 | 15 | -1 | 17 | 6 | 174 | 158 | 17 | -2 | 17 | 7 | 181 | 90 | 9 |
| | | | | | | 0 | 17 | 6 | 48 | 4 | 43 | -1 | 17 | 7 | 141 | 157 | 16 |
| | | | | | | 1 | 17 | 6 | 182 | 157 | 13 | 0 | 17 | 7 | 308 | 304 | 9 |
| | | | | | | -3 | 17 | 6 | 254 | 207 | 20 | -2 | 17 | 7 | 129 | 122 | 16 |
| | | | | | | -1 | 17 | 6 | 62 | 55 | 38 | | | | | | |
| | | | | | | 0 | 17 | 6 | 108 | 88 | 25 | | | | | | |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 2 | 17 | 5 | 195 | 189 | 10 | -2 | 17 | 6 | 56 | 51 | 44 | -2 | 17 | 7 | 21 | 16 | 20 | 2 | 16 | 7 | 172 | 156 | 21 |
| 3 | 17 | 5 | 169 | 169 | 12 | -1 | 17 | 6 | 152 | 141 | 29 | -1 | 17 | 7 | 241 | 232 | 18 | 3 | 16 | 7 | 72 | 91 | 25 |
| -3 | 18 | 5 | 135 | 110 | 39 | 0 | 17 | 6 | 0 | 40 | 14 | 0 | 17 | 7 | 435 | 454 | 15 | -3 | 17 | 7 | 62 | 69 | 62 |
| -2 | 18 | 5 | 79 | 74 | 19 | 1 | 17 | 6 | 116 | 114 | 16 | 1 | 17 | 7 | 228 | 232 | 24 | -2 | 17 | 7 | 0 | 86 | 1 |
| -1 | 18 | 5 | 172 | 140 | 20 | 2 | 17 | 6 | 349 | 334 | 16 | 2 | 17 | 7 | 56 | 15 | 55 | -1 | 17 | 7 | 113 | 86 | 18 |
| 0 | 18 | 5 | 45 | 19 | 45 | 3 | 17 | 6 | 503 | 537 | 21 | 3 | 17 | 7 | 52 | 88 | 51 | 0 | 17 | 7 | 179 | 169 | 10 |
| 1 | 18 | 5 | 126 | 140 | 16 | -3 | 18 | 6 | 144 | 139 | 7 | -3 | 18 | 7 | 150 | 150 | 52 | 1 | 17 | 7 | 83 | 86 | 26 |
| 2 | 18 | 5 | 49 | 73 | 49 | -2 | 18 | 6 | 501 | 537 | 20 | -2 | 18 | 7 | 124 | 107 | 12 | 2 | 17 | 7 | 77 | 69 | 34 |
| 3 | 18 | 5 | 105 | 109 | 13 | -1 | 18 | 6 | 346 | 333 | 24 | -1 | 18 | 7 | 92 | 59 | 24 | 3 | 17 | 7 | 62 | 69 | 62 |
| -3 | 19 | 5 | 71 | 50 | 35 | 0 | 18 | 6 | 127 | 114 | 14 | 0 | 18 | 7 | 55 | 52 | 51 | -3 | 18 | 7 | 198 | 200 | 27 |
| -2 | 19 | 5 | 87 | 99 | 41 | 1 | 18 | 6 | 152 | 154 | 19 | 1 | 18 | 7 | 54 | 60 | 54 | -2 | 18 | 7 | 91 | 56 | 25 |
| -1 | 19 | 5 | 79 | 48 | 22 | 2 | 18 | 6 | 0 | 33 | 1 | 2 | 18 | 7 | 94 | 107 | 22 | -1 | 18 | 7 | 66 | 49 | 37 |
| 0 | 19 | 5 | 81 | 100 | 21 | -3 | 19 | 6 | 455 | 416 | 20 | -3 | 19 | 7 | 159 | 149 | 15 | 0 | 18 | 7 | 98 | 111 | 18 |
| 1 | 19 | 5 | 59 | 50 | 59 | -2 | 19 | 6 | 544 | 525 | 23 | -2 | 19 | 7 | 319 | 338 | 11 | 1 | 18 | 7 | 48 | 49 | 47 |
| 2 | 19 | 5 | 55 | 64 | 55 | -1 | 19 | 6 | 0 | 35 | 1 | -1 | 19 | 7 | 86 | 69 | 18 | 2 | 18 | 7 | 182 | 201 | 14 |
| 3 | 19 | 5 | 172 | 163 | 12 | 0 | 19 | 6 | 542 | 524 | 25 | 0 | 19 | 7 | 94 | 107 | 13 | -3 | 19 | 7 | 68 | 57 | 27 |
| -3 | 20 | 5 | 44 | 77 | 43 | 1 | 19 | 6 | 451 | 416 | 30 | 1 | 19 | 7 | 351 | 348 | 25 | -2 | 19 | 7 | 93 | 70 | 16 |
| -2 | 20 | 5 | 115 | 116 | 14 | 2 | 19 | 6 | 189 | 196 | 24 | 2 | 19 | 7 | 72 | 69 | 23 | -1 | 19 | 7 | 107 | 124 | 14 |
| -1 | 20 | 5 | 85 | 56 | 32 | -3 | 20 | 6 | 110 | 97 | 12 | -3 | 20 | 7 | 317 | 338 | 13 | 0 | 19 | 7 | 35 | 3 | 35 |
| 0 | 20 | 5 | 93 | 124 | 20 | -2 | 20 | 6 | 417 | 439 | 15 | -2 | 20 | 7 | 117 | 142 | 7 | 1 | 19 | 7 | 211 | 260 | 16 |
| 1 | 20 | 5 | 52 | 70 | 51 | -1 | 20 | 6 | 391 | 381 | 50 | -1 | 20 | 7 | 49 | 35 | 10 | 2 | 19 | 7 | 39 | 47 | 38 |
| 2 | 20 | 5 | 68 | 82 | 20 | 0 | 20 | 6 | 438 | 440 | 17 | 0 | 20 | 7 | 252 | 257 | 9 | -3 | 20 | 7 | 101 | 91 | 14 |
| -3 | 21 | 5 | 49 | 66 | 49 | 1 | 20 | 6 | 104 | 98 | 16 | 1 | 20 | 7 | 123 | 137 | 12 | -2 | 20 | 7 | 88 | 117 | 17 |
| -2 | 21 | 5 | 96 | 94 | 17 | 2 | 20 | 6 | 210 | 196 | 24 | 2 | 20 | 7 | 323 | 306 | 15 | -1 | 20 | 7 | 24 | 24 | 30 |
| -1 | 21 | 5 | 61 | 66 | 39 | -3 | 21 | 6 | 54 | 65 | 12 | -3 | 21 | 7 | 113 | 137 | 14 | 0 | 20 | 7 | 79 | 117 | 21 |
| 0 | 21 | 5 | 50 | 82 | 50 | -2 | 21 | 6 | 36 | 57 | 42 | -2 | 21 | 7 | 256 | 256 | 38 | 1 | 20 | 7 | 65 | 92 | 36 |
| 1 | 21 | 5 | 0 | 22 | 16 | -1 | 21 | 6 | 96 | 119 | 35 | -1 | 21 | 7 | 127 | 108 | 20 | 2 | 20 | 7 | 92 | 85 | 14 |
| 2 | 21 | 5 | 88 | 97 | 26 | 0 | 21 | 6 | 174 | 165 | 19 | 0 | 21 | 7 | 147 | 123 | 14 | -3 | 21 | 7 | 221 | 209 | 21 |
| -3 | 22 | 5 | 375 | 331 | 17 | 1 | 21 | 6 | 292 | 269 | 7 | 1 | 21 | 7 | 59 | 76 | 32 | -2 | 21 | 7 | 154 | 167 | 12 |
| -2 | 22 | 5 | 95 | 96 | 26 | 2 | 21 | 6 | 95 | 83 | 12 | 2 | 21 | 7 | 101 | 123 | 46 | -1 | 21 | 7 | 213 | 210 | 13 |
| -1 | 22 | 5 | 59 | 89 | 17 | -3 | 22 | 6 | 292 | 269 | 12 | -3 | 22 | 7 | 94 | 108 | 17 | 0 | 21 | 7 | 62 | 86 | 41 |
| 0 | 22 | 5 | 53 | 31 | 42 | -2 | 22 | 6 | 167 | 165 | 12 | -2 | 22 | 7 | 69 | 75 | 21 | 1 | 21 | 7 | 28 | 43 | 28 |
| 1 | 22 | 5 | 0 | 89 | 1 | -1 | 22 | 6 | 127 | 119 | 16 | -1 | 22 | 7 | 197 | 226 | 18 | 2 | 21 | 7 | 25 | 20 | 24 |
| 2 | 22 | 5 | 78 | 38 | 23 | 0 | 22 | 6 | 77 | 57 | 1 | 0 | 22 | 7 | 89 | 45 | 21 | -3 | 22 | 7 | 113 | 127 | 29 |
| -3 | 23 | 5 | 26 | 0 | 26 | 1 | 22 | 6 | 82 | 58 | 29 | 1 | 22 | 7 | 204 | 226 | 17 | -2 | 22 | 7 | 46 | 19 | 45 |
| -2 | 23 | 5 | 0 | 2 | 40 | 2 | 22 | 6 | 209 | 230 | 20 | 2 | 22 | 7 | 97 | 76 | 27 | -1 | 22 | 7 | 80 | 43 | 36 |
| -1 | 23 | 5 | 40 | 38 | 29 | -3 | 23 | 6 | 377 | 364 | 14 | -3 | 23 | 7 | 73 | 71 | 23 | 0 | 22 | 7 | 99 | 96 | 15 |
| 0 | 23 | 5 | 682 | 694 | 6 | -2 | 23 | 6 | 126 | 150 | 29 | -2 | 23 | 7 | 69 | 75 | 10 | 1 | 22 | 7 | 0 | 5 | 1 |
| 1 | 23 | 5 | 126 | 138 | 13 | -1 | 23 | 6 | 391 | 364 | 24 | -1 | 23 | 7 | 184 | 183 | 17 | 2 | 22 | 7 | 113 | 96 | 15 |
| -3 | 0 | 6 | 457 | 482 | 26 | 0 | 23 | 6 | 245 | 230 | 19 | 0 | 23 | 7 | 30 | 10 | 30 | -3 | 23 | 7 | 69 | 43 | 26 |
| -2 | 0 | 6 | 159 | 153 | 7 | 1 | 23 | 6 | 80 | 59 | 32 | 1 | 23 | 7 | 135 | 165 | 17 | -2 | 23 | 7 | 268 | 335 | 12 |
| -1 | 0 | 6 | 0 | 44 | 53 | 2 | 23 | 6 | 112 | 77 | 14 | 2 | 23 | 7 | 39 | 86 | 19 | -1 | 23 | 7 | 362 | 410 | 13 |
| 0 | 0 | 6 | 53 | 90 | 16 | -3 | 0 | 8 | 109 | 110 | 22 | -3 | 0 | 9 | 0 | 59 | 32 | 0 | 23 | 7 | 241 | 247 | 12 |
| -3 | 1 | 6 | 0 | 25 | 7 | -2 | 0 | 8 | 70 | 87 | 69 | -2 | 0 | 9 | 338 | 335 | 14 | 1 | 23 | 7 | 84 | 89 | 16 |
| -2 | 1 | 6 | 362 | 346 | 6 | -1 | 0 | 8 | 205 | 202 | 8 | -1 | 0 | 9 | 251 | 304 | 22 | 2 | 23 | 7 | 0 | 2 | 1 |
| -1 | 1 | 6 | 98 | 106 | 7 | 0 | 0 | 8 | 0 | 23 | 1 | 0 | 0 | 9 | 461 | 508 | 69 | -3 | 0 | 10 | 273 | 264 | 43 |
| 0 | 1 | 6 | 184 | 165 | 8 | -3 | 1 | 8 | | | | -3 | 1 | 9 | 258 | 304 | 8 | -2 | 0 | 10 | 81 | 73 | 36 |
| 1 | 1 | 6 | 91 | 106 | 7 | | | | | | | | | | | | | -1 | 0 | 10 | 102 | 99 | 11 |
| 2 | 1 | 6 | 368 | 346 | 8 | | | | | | | | | | | | | 0 | 0 | 10 | 203 | 213 | 11 |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 3 | 1 | 8 | 58 | 24 | 57 | 0 | 11 | 8 | 592 | 594 | 21 | 2 | 1 | 9 | 344 | 335 | 22 | -1 | 1 | 10 | 246 | 265 | 8 |
| 4 | 1 | 8 | 64 | 89 | 64 | 1 | 11 | 8 | 48 | 22 | 47 | 3 | 1 | 9 | 118 | 117 | 11 | 0 | 1 | 10 | 195 | 214 | 11 |
| -4 | 2 | 8 | 86 | 53 | 80 | 2 | 11 | 8 | 209 | 201 | 10 | 4 | 1 | 9 | 76 | 86 | 75 | 1 | 1 | 10 | 114 | 99 | 22 |
| -3 | 2 | 8 | 165 | 151 | 8 | -4 | 12 | 8 | 131 | 86 | 42 | -4 | 2 | 9 | 136 | 76 | 19 | 2 | 1 | 10 | 82 | 73 | 18 |
| -2 | 2 | 8 | 142 | 123 | 10 | -3 | 12 | 8 | 135 | 110 | 30 | -3 | 2 | 9 | 175 | 157 | 16 | -4 | 2 | 10 | 242 | 263 | 26 |
| 2 | 2 | 8 | 249 | 274 | 7 | -2 | 12 | 8 | 124 | 110 | 19 | -2 | 2 | 9 | 239 | 238 | 12 | -3 | 2 | 10 | 163 | 116 | 19 |
| 3 | 2 | 8 | 640 | 649 | 19 | -1 | 12 | 8 | 128 | 173 | 14 | -1 | 2 | 9 | 713 | 816 | 31 | -2 | 2 | 10 | 112 | 89 | 9 |
| 4 | 2 | 8 | 239 | 275 | 8 | 0 | 12 | 8 | 30 | 10 | 29 | 0 | 2 | 9 | 741 | 783 | 26 | -1 | 2 | 10 | 233 | 253 | 9 |
| -3 | 3 | 8 | 103 | 122 | 27 | 1 | 12 | 8 | 36 | 58 | 35 | 1 | 2 | 9 | 731 | 816 | 29 | 0 | 2 | 10 | 437 | 476 | 11 |
| 0 | 3 | 8 | 166 | 152 | 10 | 2 | 12 | 8 | 0 | 42 | 1 | 2 | 2 | 9 | 232 | 237 | 19 | 1 | 2 | 10 | 139 | 133 | 29 |
| 1 | 3 | 8 | 0 | 0 | 53 | -3 | 12 | 8 | 64 | 59 | 47 | -4 | 3 | 9 | 156 | 157 | 11 | 2 | 2 | 10 | 426 | 477 | 7 |
| 2 | 3 | 8 | 92 | 119 | 30 | -4 | 12 | 8 | 49 | 9 | 48 | 3 | 3 | 9 | 87 | 76 | 67 | -4 | 3 | 10 | 214 | 254 | 13 |
| -4 | 3 | 8 | 216 | 228 | 7 | -3 | 13 | 8 | 185 | 173 | 13 | 4 | 3 | 9 | 78 | 76 | 39 | -3 | 3 | 10 | 67 | 89 | 20 |
| -3 | 3 | 8 | 288 | 261 | 13 | -2 | 13 | 8 | 110 | 110 | 19 | -3 | 3 | 9 | 205 | 188 | 7 | -2 | 3 | 10 | 58 | 116 | 24 |
| -2 | 3 | 8 | 710 | 725 | 27 | -1 | 13 | 8 | 89 | 10 | 88 | -2 | 3 | 9 | 181 | 181 | 10 | -1 | 3 | 10 | 259 | 235 | 58 |
| -1 | 3 | 8 | 0 | 2 | 1 | 0 | 13 | 8 | 88 | 106 | 19 | -1 | 3 | 9 | 147 | 154 | 7 | 0 | 3 | 10 | 154 | 148 | 29 |
| 0 | 3 | 8 | 650 | 725 | 20 | 1 | 13 | 8 | 185 | 188 | 10 | 0 | 3 | 9 | 519 | 573 | 18 | 1 | 3 | 10 | 262 | 254 | 7 |
| 1 | 3 | 8 | 272 | 260 | 21 | 2 | 13 | 8 | 131 | 116 | 14 | 1 | 3 | 9 | 139 | 154 | 6 | 2 | 3 | 10 | 271 | 277 | 13 |
| 2 | 3 | 8 | 242 | 228 | 20 | 3 | 13 | 8 | 300 | 282 | 10 | 2 | 3 | 9 | 142 | 181 | 24 | -3 | 3 | 10 | 356 | 421 | 12 |
| -4 | 3 | 8 | 136 | 119 | 31 | -4 | 13 | 8 | 136 | 116 | 9 | -4 | 4 | 9 | 199 | 188 | 17 | -2 | 3 | 10 | 278 | 277 | 11 |
| -3 | 4 | 8 | 208 | 135 | 15 | -3 | 14 | 8 | 194 | 188 | 10 | -3 | 4 | 9 | 96 | 77 | 48 | -1 | 3 | 10 | 280 | 254 | 12 |
| -2 | 4 | 8 | 104 | 93 | 15 | -2 | 14 | 8 | 108 | 106 | 14 | -2 | 4 | 9 | 98 | 87 | 28 | 1 | 4 | 10 | 165 | 147 | 19 |
| -1 | 4 | 8 | 321 | 348 | 16 | -1 | 14 | 8 | 0 | 10 | 1 | -1 | 4 | 9 | 127 | 128 | 12 | 2 | 4 | 10 | 156 | 234 | 15 |
| 0 | 4 | 8 | 117 | 132 | 7 | 0 | 14 | 8 | 51 | 64 | 51 | 0 | 4 | 9 | 243 | 254 | 12 | -3 | 4 | 10 | 259 | 233 | 33 |
| 1 | 4 | 8 | 536 | 592 | 16 | 1 | 14 | 8 | 185 | 178 | 11 | 1 | 4 | 9 | 626 | 693 | 46 | -2 | 4 | 10 | 41 | 37 | 17 |
| 2 | 4 | 8 | 131 | 131 | 5 | 2 | 14 | 8 | 148 | 136 | 15 | -4 | 4 | 9 | 822 | 828 | 29 | -1 | 4 | 10 | 221 | 211 | 41 |
| 3 | 4 | 8 | 364 | 347 | 21 | 3 | 14 | 8 | 259 | 236 | 8 | -3 | 4 | 9 | 626 | 694 | 19 | 0 | 4 | 10 | 586 | 665 | 16 |
| 4 | 4 | 8 | 82 | 93 | 20 | -4 | 14 | 8 | 159 | 137 | 10 | -2 | 4 | 9 | 253 | 254 | 19 | 1 | 4 | 10 | 144 | 158 | 32 |
| -4 | 5 | 8 | 122 | 185 | 42 | -3 | 15 | 8 | 204 | 178 | 11 | 3 | 5 | 9 | 138 | 128 | 12 | 2 | 4 | 10 | 616 | 663 | 7 |
| -3 | 5 | 8 | 207 | 215 | 15 | -2 | 15 | 8 | 61 | 64 | 37 | -4 | 5 | 9 | 54 | 87 | 53 | -3 | 5 | 10 | 201 | 212 | 20 |
| -2 | 5 | 8 | 138 | 139 | 15 | -1 | 15 | 8 | 67 | 64 | 30 | -3 | 5 | 9 | 203 | 177 | 29 | -2 | 5 | 10 | 9 | 37 | 21 |
| -1 | 5 | 8 | 261 | 278 | 13 | 0 | 15 | 8 | 75 | 69 | 18 | -2 | 5 | 9 | 211 | 223 | 9 | -1 | 5 | 10 | 95 | 80 | 8 |
| 0 | 5 | 8 | 220 | 239 | 13 | 1 | 15 | 8 | 118 | 118 | 14 | -1 | 5 | 9 | 288 | 283 | 14 | 0 | 5 | 10 | 246 | 254 | 30 |
| 1 | 5 | 8 | 773 | 792 | 27 | 2 | 15 | 8 | 464 | 472 | 12 | 0 | 5 | 9 | 89 | 100 | 10 | 1 | 5 | 10 | 39 | 23 | 19 |
| 2 | 5 | 8 | 225 | 240 | 7 | 3 | 15 | 8 | 133 | 117 | 11 | 1 | 5 | 9 | 273 | 345 | 9 | 2 | 5 | 10 | 171 | 162 | 38 |
| 3 | 5 | 8 | 291 | 277 | 19 | -4 | 16 | 8 | 44 | 70 | 43 | 2 | 5 | 9 | 102 | 99 | 9 | -3 | 6 | 10 | 846 | 854 | 17 |
| -4 | 6 | 8 | 150 | 139 | 15 | -3 | 16 | 8 | 69 | 64 | 25 | -4 | 6 | 9 | 301 | 284 | 21 | -2 | 6 | 10 | 164 | 162 | 25 |
| -3 | 6 | 8 | 144 | 215 | 6 | -2 | 16 | 8 | 76 | 52 | 49 | -3 | 6 | 9 | 224 | 223 | 11 | -1 | 6 | 10 | 0 | 24 | 7 |
| -2 | 6 | 8 | 199 | 158 | 13 | -1 | 16 | 8 | 81 | 87 | 17 | -2 | 6 | 9 | 138 | 176 | 30 | 0 | 6 | 10 | 251 | 254 | 1 |
| -1 | 6 | 8 | 261 | 246 | 13 | 0 | 16 | 8 | 230 | 204 | 23 | -1 | 6 | 9 | 91 | 37 | 31 | 1 | 6 | 10 | 91 | 80 | 17 |
| 0 | 6 | 8 | 200 | 303 | 14 | 1 | 16 | 8 | 207 | 204 | 12 | 0 | 6 | 9 | 219 | 218 | 12 | 2 | 6 | 10 | 79 | 75 | 43 |
| 1 | 6 | 8 | 301 | 217 | 9 | 2 | 16 | 8 | 222 | 87 | 12 | 1 | 6 | 9 | 78 | 59 | 12 | -3 | 6 | 10 | 294 | 283 | 41 |
| 2 | 6 | 8 | 184 | 276 | 14 | -3 | 16 | 8 | 107 | 87 | 43 | 2 | 6 | 9 | 42 | 45 | 56 | -2 | 6 | 10 | 269 | 256 | 8 |
| 3 | 6 | 8 | 516 | 526 | 25 | -4 | 17 | 8 | 24 | 51 | 25 | 3 | 6 | 9 | 413 | 441 | 12 | -1 | 6 | 10 | 433 | 491 | 13 |
| -4 | 6 | 8 | 144 | 139 | 31 | -3 | 17 | 8 | 146 | 137 | 23 | -4 | 7 | 9 | 66 | 47 | 12 | 0 | 6 | 10 | 951 | 909 | 26 |
| -3 | 7 | 8 | 199 | 158 | 23 | -2 | 17 | 8 | 161 | 162 | 23 | -3 | 7 | 9 | 57 | 59 | 56 | 1 | 6 | 10 | 445 | 491 | 29 |
| -2 | 7 | 8 | 261 | 246 | 11 | -1 | 17 | 8 | 260 | 251 | 11 | -2 | 7 | 9 | 228 | 219 | 12 | 2 | 6 | 10 | 255 | 257 | 26 |
| -1 | 7 | 8 | 200 | 215 | 22 | 0 | 17 | 8 | 0 | 35 | 14 | -1 | 7 | 9 | 0 | 37 | 1 | -4 | 6 | 10 | 293 | 282 | 22 |
| 0 | 7 | 8 | 76 | 65 | 45 | 1 | 17 | 8 | 248 | 251 | 9 | 0 | 7 | 9 | 102 | 108 | 27 | -3 | 6 | 10 | 83 | 75 | 22 |
| -3 | 7 | 8 | 213 | 181 | 9 | | | | | | | | | | | | | | | | | | | |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| -2 | 7 | 8 | 329 | 326 | 15 | -3 | 7 | 8 | 166 | 161 | 13 | -3 | 7 | 9 | 248 | 252 | 12 | -4 | 7 | 10 | 113 | 128 | 42 |
| -1 | 7 | 8 | 70 | 51 | 23 | -2 | 7 | 8 | 145 | 138 | 14 | -2 | 7 | 9 | 305 | 333 | 16 | -3 | 7 | 10 | 23 | 49 | 23 |
| 0 | 7 | 8 | 117 | 117 | 12 | -1 | 7 | 8 | 68 | 34 | 48 | -1 | 7 | 9 | 216 | 230 | 9 | -2 | 7 | 10 | 455 | 473 | 12 |
| 1 | 7 | 8 | 42 | 51 | 42 | 0 | 7 | 8 | 156 | 142 | 10 | 0 | 7 | 9 | 468 | 496 | 14 | -1 | 7 | 10 | 73 | 97 | 26 |
| 2 | 7 | 8 | 335 | 327 | 23 | 1 | 7 | 8 | 237 | 251 | 9 | 1 | 7 | 9 | 195 | 230 | 9 | 0 | 7 | 10 | 827 | 837 | 29 |
| 3 | 7 | 8 | 193 | 182 | 15 | 2 | 7 | 8 | 218 | 187 | 10 | 2 | 7 | 9 | 359 | 333 | 21 | 1 | 7 | 10 | 72 | 96 | 21 |
| 4 | 7 | 8 | 54 | 65 | 54 | 3 | 7 | 8 | 205 | 251 | 14 | 3 | 7 | 9 | 262 | 252 | 16 | 2 | 7 | 10 | 479 | 473 | 31 |
| 3 | 7 | 10 | 81 | 51 | 24 | 4 | 7 | 8 | 159 | 189 | 20 | 4 | 7 | 9 | 136 | 136 | 14 | 3 | 7 | 10 | 162 | 171 | 11 |
| 4 | 7 | 10 | 103 | 127 | 17 | -4 | 8 | 8 | 57 | 70 | 56 | -4 | 8 | 9 | 67 | 67 | 28 | -3 | 8 | 10 | 339 | 356 | 9 |
| -4 | 8 | 10 | 0 | 30 | 1 | -3 | 8 | 8 | 88 | 96 | 21 | -3 | 8 | 9 | 109 | 70 | 24 | -2 | 8 | 10 | 457 | 456 | 16 |
| -3 | 8 | 10 | 124 | 100 | 19 | -2 | 8 | 8 | 168 | 164 | 10 | -2 | 8 | 9 | 133 | 122 | 21 | -1 | 8 | 10 | 456 | 465 | 16 |
| -2 | 8 | 10 | 300 | 301 | 9 | -1 | 8 | 8 | 115 | 141 | 34 | -1 | 8 | 9 | 216 | 171 | 33 | 0 | 8 | 10 | 453 | 455 | 20 |
| -1 | 8 | 10 | 196 | 192 | 10 | 0 | 8 | 8 | 120 | 114 | 16 | 0 | 8 | 9 | 141 | 125 | 11 | 1 | 8 | 10 | 352 | 356 | 11 |
| 0 | 8 | 10 | 170 | 198 | 8 | 1 | 8 | 8 | 107 | 141 | 23 | 1 | 8 | 9 | 102 | 84 | 13 | 2 | 8 | 10 | 182 | 171 | 10 |
| 1 | 8 | 10 | 176 | 195 | 13 | 2 | 8 | 8 | 139 | 164 | 16 | 2 | 8 | 9 | 127 | 126 | 14 | 3 | 8 | 10 | 96 | 122 | 23 |
| 2 | 8 | 10 | 329 | 301 | 12 | 3 | 8 | 8 | 81 | 51 | 23 | 3 | 8 | 9 | 184 | 199 | 21 | 4 | 8 | 10 | 120 | 123 | 19 |
| 3 | 8 | 10 | 94 | 100 | 21 | 4 | 8 | 8 | 23 | 30 | 22 | 4 | 8 | 9 | 128 | 171 | 22 | -4 | 9 | 10 | 0 | 16 | 1 |
| 4 | 8 | 10 | 33 | 30 | 32 | -4 | 9 | 8 | 41 | 26 | 41 | -4 | 9 | 9 | 87 | 122 | 20 | -3 | 9 | 10 | 84 | 65 | 13 |
| -4 | 9 | 10 | 70 | 36 | 48 | -3 | 9 | 8 | 0 | 30 | 31 | -3 | 9 | 9 | 96 | 70 | 16 | -2 | 9 | 10 | 472 | 445 | 17 |
| -3 | 9 | 10 | 103 | 76 | 22 | -2 | 9 | 8 | 84 | 51 | 1 | -2 | 9 | 9 | 219 | 212 | 20 | -1 | 9 | 10 | 146 | 143 | 11 |
| -2 | 9 | 10 | 214 | 217 | 14 | -1 | 9 | 8 | 0 | 19 | 17 | -1 | 9 | 9 | 43 | 36 | 43 | 0 | 9 | 10 | 472 | 444 | 21 |
| -1 | 9 | 10 | 203 | 194 | 10 | 0 | 9 | 8 | 82 | 110 | 40 | 0 | 9 | 9 | 123 | 124 | 13 | 1 | 9 | 10 | 73 | 64 | 20 |
| 0 | 9 | 10 | 193 | 190 | 10 | 1 | 9 | 8 | 70 | 60 | 18 | 1 | 9 | 9 | 403 | 400 | 15 | 2 | 9 | 10 | 0 | 17 | 1 |
| 1 | 9 | 10 | 171 | 193 | 14 | 2 | 9 | 8 | 98 | 110 | 55 | 2 | 9 | 9 | 118 | 123 | 21 | 3 | 9 | 10 | 112 | 122 | 12 |
| 2 | 9 | 10 | 212 | 217 | 9 | 3 | 9 | 8 | 55 | 19 | 1 | 3 | 9 | 9 | 89 | 36 | 15 | 4 | 9 | 10 | 87 | 92 | 29 |
| 3 | 9 | 10 | 96 | 77 | 21 | 4 | 9 | 8 | 0 | 60 | 60 | 4 | 9 | 9 | 231 | 212 | 10 | -3 | 10 | 10 | 43 | 14 | 42 |
| 4 | 9 | 10 | 65 | 36 | 36 | -4 | 10 | 8 | 27 | 4 | 27 | -4 | 10 | 9 | 82 | 59 | 21 | -2 | 10 | 10 | 96 | 110 | 12 |
| -4 | 10 | 10 | 113 | 104 | 21 | -3 | 10 | 8 | 20 | 60 | 19 | -3 | 10 | 9 | 143 | 113 | 25 | -1 | 10 | 10 | 127 | 122 | 22 |
| -3 | 10 | 10 | 104 | 167 | 31 | -2 | 10 | 8 | 77 | 52 | 26 | -2 | 10 | 9 | 159 | 155 | 27 | 0 | 10 | 10 | 290 | 303 | 12 |
| -2 | 10 | 10 | 153 | 167 | 17 | -1 | 10 | 8 | 445 | 488 | 22 | -1 | 10 | 9 | 107 | 91 | 10 | 1 | 10 | 10 | 104 | 121 | 13 |
| -1 | 10 | 10 | 92 | 78 | 12 | 0 | 10 | 8 | 27 | 40 | 26 | 0 | 10 | 9 | 123 | 94 | 14 | 2 | 10 | 10 | 121 | 110 | 12 |
| 0 | 10 | 10 | 265 | 269 | 20 | 1 | 10 | 8 | 142 | 133 | 23 | 1 | 10 | 9 | 478 | 576 | 22 | 3 | 10 | 10 | 0 | 13 | 1 |
| 1 | 10 | 10 | 595 | 595 | 15 | 2 | 10 | 8 | 71 | 22 | 71 | 2 | 10 | 9 | 90 | 88 | 44 | 4 | 10 | 10 | 102 | 91 | 12 |
| 2 | 10 | 10 | 269 | 269 | 20 | 3 | 10 | 8 | 101 | 77 | 24 | 3 | 10 | 9 | 80 | 81 | 25 | -2 | 11 | 10 | 42 | 75 | 41 |
| 3 | 10 | 10 | 246 | 84 | 13 | -3 | 11 | 8 | 280 | 275 | 11 | -3 | 11 | 9 | 263 | 280 | 15 | -1 | 11 | 10 | 221 | 231 | 12 |
| -3 | 11 | 10 | 84 | 78 | 18 | -2 | 11 | 8 | 401 | 431 | 20 | -2 | 11 | 9 | 80 | 88 | 13 | 0 | 11 | 10 | 142 | 139 | 9 |
| -2 | 11 | 10 | 186 | 167 | 17 | -1 | 11 | 8 | 352 | 391 | 14 | -1 | 11 | 9 | 92 | 88 | 68 | 1 | 11 | 10 | 166 | 164 | 10 |
| -1 | 11 | 10 | 122 | 120 | 15 | 0 | 11 | 8 | 387 | 431 | 20 | 0 | 11 | 9 | 478 | 494 | 15 | 2 | 11 | 10 | 194 | 138 | 30 |
| 0 | 11 | 10 | 119 | 100 | 20 | 1 | 11 | 8 | 285 | 274 | 26 | 1 | 11 | 9 | 90 | 88 | 21 | 3 | 11 | 10 | 147 | 164 | 23 |
| 1 | 11 | 10 | 106 | 113 | 16 | 2 | 11 | 8 | 66 | 22 | 23 | 2 | 11 | 9 | 80 | 81 | 19 | -3 | 11 | 10 | 228 | 231 | 11 |
| 2 | 11 | 10 | 141 | 136 | 9 | 3 | 11 | 8 | 97 | 77 | 13 | 3 | 11 | 9 | 277 | 281 | 12 | -2 | 12 | 10 | 78 | 75 | 20 |
| 3 | 11 | 10 | 316 | 295 | 8 | -2 | 12 | 8 | 137 | 92 | 18 | -2 | 12 | 9 | 46 | 78 | 46 | -1 | 12 | 10 | 61 | 71 | 61 |
| -2 | 12 | 10 | 142 | 136 | 13 | -1 | 12 | 8 | 203 | 199 | 12 | -1 | 12 | 9 | 79 | 68 | 23 | 0 | 12 | 10 | 210 | 224 | 12 |
| -1 | 12 | 10 | 121 | 120 | 13 | 0 | 12 | 8 | 235 | 233 | 13 | 0 | 12 | 9 | 86 | 78 | 34 | 1 | 12 | 10 | 149 | 148 | 12 |
| 0 | 12 | 10 | 120 | 113 | 26 | 1 | 12 | 8 | 466 | 493 | 18 | 1 | 12 | 9 | 159 | 140 | 11 | 2 | 12 | 10 | 98 | 79 | 27 |
| 1 | 12 | 10 | 101 | 99 | 51 | 2 | 12 | 8 | 28 | 42 | 28 | 2 | 12 | 9 | 0 | 15 | 1 | 3 | 12 | 10 | 200 | 169 | 13 |
| 2 | 12 | 10 | 51 | 98 | 17 | 3 | 12 | 8 | 435 | 492 | 14 |   |   |   |      |      |     | -2 | 12 | 10 | 91 | 79 | 8 |
| 3 | 12 | 10 | 89 | 121 | 15 | -1 | 12 | 8 | 245 | 232 | 19 |   |   |   |      |      |     | -1 | 12 | 10 | 153 | 148 | 11 |
| -2 | 12 | 10 | 214 | 221 | 9 |   |   |   |      |      |     |   |   |   |      |      |     |   |   |   |      |      |     |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|
| 0 | 12 | 10 | 286 | 256 | 12 | 3 | 2 | 11 | 202 | 199 | 11 | 1 | 3 | 12 | 162 | 140 | 8 | 3 | 3 | 12 | 223 | 224 | 11 |
| -1 | 12 | 10 | 216 | 221 | 8 | 4 | 2 | 11 | 0 | 92 | 1 | 2 | 3 | 12 | 94 | 78 | 17 | 4 | 3 | 12 | 47 | 72 | 47 |
| 2 | 12 | 10 | 61 | 84 | 39 | -4 | 3 | 11 | 199 | 181 | 31 | 3 | 3 | 12 | 99 | 69 | 16 | -3 | 3 | 12 | 0 | 56 | 1 |
| 3 | 12 | 10 | 122 | 121 | 13 | -3 | 3 | 11 | 110 | 114 | 10 | -3 | 3 | 12 | 101 | 96 | 32 | -2 | 13 | 12 | 97 | 117 | 17 |
| -3 | 12 | 10 | 103 | 98 | 16 | 4 | 3 | 11 | 61 | 94 | 36 | 4 | 3 | 12 | 214 | 231 | 27 | -1 | 13 | 12 | 180 | 175 | 9 |
| -4 | 13 | 10 | 80 | 110 | 35 | -2 | 3 | 11 | 497 | 546 | 17 | -2 | 3 | 12 | 59 | 67 | 30 | 2 | 13 | 12 | 160 | 147 | 8 |
| 1 | 13 | 10 | 129 | 147 | 13 | -1 | 3 | 11 | 517 | 560 | 18 | -1 | 3 | 12 | 12 | 43 | 11 | 0 | 13 | 12 | 180 | 175 | 8 |
| 2 | 13 | 10 | 149 | 151 | 11 | 0 | 3 | 11 | 497 | 547 | 15 | 0 | 3 | 12 | 349 | 322 | 21 | 1 | 13 | 12 | 138 | 116 | 13 |
| -1 | 13 | 10 | 167 | 141 | 9 | 2 | 3 | 11 | 109 | 94 | 26 | 2 | 3 | 12 | 64 | 43 | 52 | -3 | 13 | 12 | 61 | 57 | 29 |
| 0 | 13 | 10 | 233 | 218 | 8 | 3 | 3 | 11 | 117 | 114 | 15 | -3 | 3 | 12 | 53 | 68 | 15 | -2 | 13 | 12 | 131 | 125 | 13 |
| -2 | 13 | 10 | 153 | 141 | 9 | -3 | 3 | 11 | 129 | 180 | 31 | -2 | 4 | 12 | 178 | 231 | 15 | 0 | 13 | 12 | 88 | 89 | 51 |
| 2 | 13 | 10 | 161 | 152 | 12 | -2 | 4 | 11 | 189 | 185 | 20 | -1 | 4 | 12 | 118 | 120 | 38 | 2 | 13 | 12 | 253 | 225 | 9 |
| -3 | 14 | 10 | 133 | 147 | 8 | 0 | 4 | 11 | 134 | 128 | 9 | 2 | 4 | 12 | 161 | 92 | 10 | -3 | 14 | 12 | 168 | 158 | 9 |
| 1 | 14 | 10 | 68 | 84 | 30 | 1 | 4 | 11 | 301 | 313 | 21 | 3 | 4 | 12 | 144 | 126 | 1 | -2 | 14 | 12 | 248 | 224 | 10 |
| 2 | 14 | 10 | 243 | 228 | 10 | 2 | 4 | 11 | 511 | 542 | 21 | -3 | 4 | 12 | 0 | 15 | 11 | -1 | 14 | 12 | 84 | 88 | 23 |
| 3 | 14 | 10 | 448 | 422 | 12 | -3 | 4 | 11 | 333 | 399 | 12 | -2 | 4 | 12 | 122 | 125 | 27 | 2 | 14 | 12 | 125 | 125 | 17 |
| -3 | 14 | 10 | 66 | 18 | 20 | 4 | 4 | 11 | 495 | 543 | 18 | -1 | 4 | 12 | 118 | 93 | 13 | 0 | 14 | 12 | 62 | 29 | 34 |
| 0 | 14 | 10 | 442 | 423 | 13 | -2 | 4 | 11 | 323 | 314 | 21 | 0 | 4 | 12 | 113 | 119 | 17 | 1 | 14 | 12 | 106 | 109 | 20 |
| 2 | 14 | 10 | 251 | 227 | 12 | -1 | 4 | 11 | 119 | 128 | 14 | 2 | 5 | 12 | 102 | 103 | 10 | -3 | 14 | 12 | 238 | 201 | 10 |
| -3 | 14 | 10 | 105 | 84 | 14 | 3 | 5 | 11 | 115 | 186 | 36 | 3 | 5 | 12 | 267 | 275 | 10 | -2 | 14 | 12 | 437 | 446 | 15 |
| 3 | 15 | 10 | 0 | 23 | 1 | -2 | 5 | 11 | 103 | 98 | 48 | -3 | 5 | 12 | 188 | 179 | 13 | -1 | 15 | 12 | 224 | 201 | 12 |
| -3 | 15 | 10 | 31 | 9 | 30 | -1 | 5 | 11 | 113 | 106 | 17 | -2 | 5 | 12 | 135 | 115 | 23 | 0 | 15 | 12 | 112 | 109 | 17 |
| 0 | 15 | 10 | 230 | 216 | 9 | 0 | 5 | 11 | 113 | 130 | 14 | -1 | 5 | 12 | 178 | 178 | 18 | 1 | 15 | 12 | 24 | 29 | 24 |
| 2 | 15 | 10 | 315 | 285 | 10 | 2 | 5 | 11 | 776 | 806 | 29 | 2 | 5 | 12 | 276 | 275 | 14 | 2 | 15 | 12 | 87 | 79 | 29 |
| -1 | 15 | 10 | 235 | 217 | 8 | 3 | 6 | 11 | 147 | 136 | 7 | 3 | 6 | 12 | 82 | 102 | 12 | -2 | 15 | 12 | 150 | 114 | 21 |
| 2 | 15 | 10 | 21 | 9 | 28 | -2 | 6 | 11 | 755 | 807 | 33 | -3 | 6 | 12 | 97 | 108 | 20 | -1 | 16 | 12 | 89 | 117 | 23 |
| -3 | 16 | 10 | 51 | 23 | 21 | -1 | 6 | 11 | 61 | 130 | 61 | -2 | 6 | 12 | 72 | 65 | 35 | 0 | 16 | 12 | 69 | 52 | 25 |
| -1 | 16 | 10 | 140 | 154 | 51 | 0 | 6 | 11 | 110 | 105 | 24 | -1 | 6 | 12 | 211 | 195 | 18 | 3 | 16 | 12 | 100 | 116 | 26 |
| 0 | 16 | 10 | 76 | 95 | 37 | 2 | 6 | 11 | 85 | 98 | 49 | 0 | 6 | 12 | 305 | 264 | 9 | 1 | 16 | 12 | 95 | 114 | 27 |
| 2 | 16 | 10 | 239 | 210 | 18 | -3 | 7 | 11 | 106 | 75 | 24 | 2 | 6 | 12 | 217 | 194 | 22 | -3 | 16 | 12 | 49 | 79 | 48 |
| -2 | 16 | 10 | 159 | 175 | 13 | -2 | 7 | 11 | 157 | 149 | 21 | -2 | 7 | 12 | 49 | 66 | 33 | -2 | 17 | 12 | 71 | 26 | 41 |
| 3 | 16 | 10 | 216 | 210 | 26 | -1 | 7 | 11 | 126 | 120 | 12 | -1 | 7 | 12 | 117 | 109 | 14 | 0 | 17 | 12 | 154 | 175 | 12 |
| -2 | 16 | 10 | 93 | 94 | 21 | 0 | 7 | 11 | 745 | 725 | 25 | 0 | 7 | 12 | 80 | 52 | 33 | 1 | 17 | 12 | 134 | 131 | 12 |
| 0 | 17 | 10 | 159 | 155 | 9 | 2 | 7 | 11 | 250 | 283 | 9 | 2 | 7 | 12 | 52 | 60 | 31 | -1 | 17 | 12 | 139 | 134 | 31 |
| 2 | 17 | 10 | 76 | 53 | 75 | -3 | 8 | 11 | 722 | 724 | 32 | -3 | 8 | 12 | 314 | 290 | 12 | 3 | 17 | 12 | 131 | 130 | 40 |
| -1 | 17 | 10 | 216 | 216 | 17 | -2 | 8 | 11 | 125 | 121 | 26 | -2 | 8 | 12 | 170 | 94 | 26 | 2 | 17 | 12 | 178 | 177 | 34 |
| 3 | 17 | 10 | 217 | 333 | 12 | -1 | 8 | 11 | 150 | 148 | 16 | -1 | 8 | 12 | 307 | 290 | 16 | -3 | 18 | 12 | 34 | 26 | 18 |
| -3 | 18 | 10 | 339 | 333 | 25 | 0 | 8 | 11 | 69 | 75 | 20 | 0 | 8 | 12 | 60 | 60 | 60 | -2 | 18 | 12 | 136 | 156 | 13 |
| 0 | 18 | 10 | 133 | 100 | 18 | 2 | 8 | 11 | 66 | 67 | 60 | 2 | 8 | 12 | 49 | 53 | 49 | 1 | 18 | 12 | 118 | 107 | 17 |
| 2 | 18 | 10 | 304 | 333 | 10 | -2 | 9 | 11 | 122 | 136 | 23 | -2 | 9 | 12 | 0 | 23 | 1 | -1 | 18 | 12 | 72 | 54 | 30 |
| -1 | 18 | 10 | 187 | 215 | 31 | -1 | 9 | 11 | 92 | 121 | 13 | -1 | 9 | 12 | 62 | 62 | 23 | 3 | 18 | 12 | 88 | 108 | 24 |
| 1 | 19 | 10 | 57 | 53 | 10 | 0 | 9 | 11 | 317 | 313 | 31 | 0 | 9 | 12 | 118 | 124 | 13 | -3 | 19 | 12 | 144 | 156 | 48 |
| -2 | 19 | 10 | 83 | 96 | 29 | 2 | 9 | 11 | 138 | 140 | 10 | 2 | 9 | 12 | 144 | 135 | 14 | 0 | 19 | 12 | 0 | 36 | 1 |
| 2 | 19 | 10 | 82 | 71 | 13 | -3 | 9 | 11 | 320 | 314 | 8 | -3 | 9 | 12 | 104 | 124 | 17 | 1 | 1 | 15 | 216 | 216 | 38 |
| -1 | 19 | 10 | 205 | 191 | 10 | -2 | 9 | 11 | 39 | 65 | 15 | -2 | 9 | 12 | 64 | 62 | 63 | 2 | 1 | 15 | 39 | 5 | 20 |
| 0 | 18 | 10 | 234 | 232 | 29 | -1 | 9 | 11 | 116 | 114 | 39 | -1 | 9 | 12 | 59 | 38 | 33 | -2 | 1 | 15 | 109 | 107 | 10 |
| 1 | 19 | 10 | 176 | 215 | 31 | 0 | 9 | 11 | 80 | 68 | 19 | 0 | 9 | 12 | 70 | 90 | 27 | -1 | 1 | 15 | 244 | 226 | 13 |
| -2 | 20 | 10 | 31 | 36 | 10 | 1 | 9 | 11 | 187 | 227 | 15 | 3 | 9 | 12 | 42 | 39 | 41 | 0 | 1 | 15 | 449 | 437 | 13 |
| -1 | 20 | 10 | 158 | 148 | 13 | -1 | 9 | 11 | 72 | 46 | 15 | -1 | 9 | 12 | 94 | 91 | 24 | 1 | 1 | 15 | 342 | 358 | 13 |
| 0 | 20 | 10 | 166 | 209 | 13 | 0 | 9 | 13 | 115 | 115 | 15 |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 0 | 20 | 12 | 66 | 10 | 32 | 0 | 22 | 13 | 231 | 238 | 8 | 0 | 0 | 14 | 80 | 16 | 21 | 0 | 1 | 15 | 167 | 179 | 7 |
| 1 | 20 | 12 | 209 | 209 | 11 | 0 | 0 | 13 | 459 | 462 | 17 | 0 | 0 | 14 | 522 | 680 | 32 | -1 | 1 | 15 | 347 | 358 | 13 |
| 2 | 20 | 12 | 135 | 148 | 22 | -1 | 0 | 13 | 112 | 101 | 13 | 1 | 0 | 14 | 50 | 60 | 25 | 2 | 1 | 15 | 457 | 437 | 20 |
| -1 | 21 | 12 | 18 | 25 | 17 | 0 | 0 | 13 | 469 | 462 | 30 | 2 | 0 | 14 | 411 | 385 | 18 | -2 | 1 | 15 | 241 | 227 | 19 |
| 0 | 21 | 12 | 64 | 72 | 36 | 1 | 0 | 13 | 241 | 238 | 9 | 3 | 0 | 14 | 42 | 63 | 41 | 3 | 1 | 15 | 107 | 107 | 14 |
| -1 | 21 | 12 | 0 | 25 | 5 | 2 | 0 | 13 | 135 | 115 | 12 | 4 | 0 | 14 | 26 | 29 | 25 | -3 | 1 | 15 | 75 | 39 | 32 |
| 0 | 22 | 12 | 120 | 127 | 14 | -3 | 1 | 13 | 48 | 46 | 47 | 0 | 1 | 14 | 95 | 98 | 24 | 4 | 1 | 15 | 195 | 199 | 15 |
| -1 | 22 | 12 | 48 | 50 | 47 | -2 | 1 | 13 | 81 | 75 | 33 | 1 | 1 | 14 | 178 | 161 | 11 | -4 | 1 | 15 | 233 | 227 | 8 |
| 0 | 22 | 12 | 32 | 72 | 32 | -1 | 1 | 13 | 17 | 26 | 17 | -1 | 1 | 14 | 274 | 285 | 13 | 0 | 2 | 15 | 218 | 230 | 9 |
| 1 | 22 | 12 | 143 | 137 | 14 | 0 | 1 | 13 | 82 | 100 | 24 | 2 | 1 | 14 | 86 | 95 | 12 | -1 | 2 | 15 | 43 | 65 | 26 |
| 2 | 0 | 13 | 205 | 214 | 14 | 1 | 1 | 13 | 106 | 96 | 25 | -2 | 1 | 14 | 215 | 260 | 7 | 1 | 2 | 15 | 198 | 229 | 10 |
| 3 | 0 | 13 | 125 | 86 | 25 | 2 | 1 | 13 | 124 | 124 | 13 | 3 | 1 | 14 | 88 | 94 | 11 | 2 | 2 | 15 | 265 | 227 | 14 |
| 4 | 0 | 13 | 186 | 158 | 25 | 3 | 1 | 13 | 111 | 96 | 11 | -3 | 1 | 14 | 265 | 285 | 13 | -2 | 2 | 15 | 197 | 198 | 11 |
| -3 | 1 | 13 | 73 | 30 | 19 | -3 | 2 | 13 | 107 | 100 | 13 | 4 | 1 | 14 | 186 | 161 | 11 | 3 | 2 | 15 | 65 | 40 | 64 |
| -2 | 1 | 13 | 187 | 185 | 11 | -2 | 2 | 13 | 0 | 26 | 1 | -4 | 1 | 14 | 121 | 98 | 17 | -3 | 2 | 15 | 137 | 157 | 18 |
| -1 | 1 | 13 | 176 | 202 | 9 | -1 | 2 | 13 | 79 | 75 | 16 | 0 | 2 | 14 | 91 | 84 | 26 | 4 | 2 | 15 | 78 | 79 | 23 |
| 0 | 1 | 13 | 240 | 260 | 8 | 0 | 2 | 13 | 85 | 12 | 31 | 1 | 2 | 14 | 133 | 104 | 20 | -4 | 2 | 15 | 79 | 81 | 13 |
| 1 | 1 | 13 | 165 | 203 | 9 | 1 | 2 | 13 | 182 | 180 | 9 | -1 | 2 | 14 | 446 | 399 | 19 | 0 | 3 | 15 | 521 | 505 | 18 |
| 2 | 1 | 13 | 187 | 186 | 11 | 2 | 2 | 13 | 156 | 161 | 11 | 2 | 2 | 14 | 161 | 161 | 10 | -1 | 3 | 15 | 260 | 302 | 9 |
| 3 | 1 | 13 | 46 | 30 | 46 | 3 | 2 | 13 | 322 | 306 | 8 | -2 | 2 | 14 | 350 | 385 | 11 | 1 | 3 | 15 | 511 | 504 | 18 |
| 4 | 1 | 13 | 164 | 158 | 46 | -3 | 3 | 13 | 85 | 97 | 20 | 3 | 2 | 14 | 152 | 160 | 9 | 2 | 3 | 15 | 79 | 81 | 10 |
| -4 | 2 | 13 | 151 | 135 | 17 | -2 | 3 | 13 | 302 | 305 | 12 | -3 | 2 | 14 | 434 | 399 | 20 | -2 | 3 | 15 | 81 | 79 | 39 |
| -3 | 2 | 13 | 159 | 141 | 16 | -1 | 3 | 13 | 156 | 161 | 11 | 4 | 2 | 14 | 77 | 83 | 24 | 3 | 3 | 15 | 161 | 156 | 32 |
| -2 | 2 | 13 | 428 | 406 | 19 | 0 | 3 | 13 | 180 | 181 | 11 | -4 | 2 | 14 | 73 | 100 | 31 | -3 | 3 | 15 | 48 | 21 | 48 |
| -1 | 2 | 13 | 174 | 199 | 7 | 1 | 3 | 13 | 41 | 12 | 41 | 0 | 3 | 14 | 103 | 208 | 25 | 4 | 3 | 15 | 132 | 139 | 13 |
| 0 | 2 | 13 | 153 | 186 | 9 | 2 | 3 | 13 | 106 | 95 | 46 | 1 | 3 | 14 | 221 | 208 | 9 | -4 | 3 | 15 | 109 | 121 | 19 |
| 1 | 2 | 13 | 180 | 199 | 11 | 3 | 3 | 13 | 178 | 181 | 16 | -1 | 3 | 14 | 145 | 131 | 11 | 0 | 4 | 15 | 446 | 445 | 16 |
| 2 | 2 | 13 | 427 | 406 | 28 | -3 | 4 | 13 | 36 | 32 | 9 | 2 | 3 | 14 | 159 | 180 | 10 | -1 | 4 | 15 | 12 | 30 | 11 |
| 3 | 2 | 13 | 148 | 140 | 12 | -2 | 4 | 13 | 229 | 217 | 8 | -2 | 3 | 14 | 85 | 81 | 42 | 1 | 4 | 15 | 449 | 445 | 20 |
| 4 | 2 | 13 | 145 | 134 | 53 | -1 | 4 | 13 | 217 | 217 | 8 | 3 | 3 | 14 | 168 | 180 | 11 | 2 | 4 | 15 | 99 | 121 | 15 |
| -4 | 3 | 13 | 101 | 70 | 24 | 0 | 4 | 13 | 222 | 217 | 25 | -3 | 3 | 14 | 94 | 131 | 19 | -2 | 4 | 15 | 139 | 139 | 14 |
| -3 | 3 | 13 | 64 | 65 | 21 | 1 | 4 | 13 | 37 | 33 | 13 | 4 | 3 | 14 | 226 | 208 | 13 | 3 | 4 | 15 | 58 | 22 | 46 |
| -2 | 3 | 13 | 508 | 488 | 23 | 2 | 4 | 13 | 171 | 181 | 16 | -4 | 3 | 14 | 100 | 100 | 52 | -3 | 4 | 15 | 91 | 109 | 25 |
| -1 | 3 | 13 | 1000 | 1007 | 35 | 3 | 4 | 13 | 141 | 154 | 9 | 0 | 4 | 14 | 83 | 15 | 37 | 4 | 4 | 15 | 221 | 184 | 19 |
| 0 | 3 | 13 | 125 | 65 | 32 | -3 | 5 | 13 | 83 | 60 | 40 | 1 | 4 | 14 | 856 | 821 | 13 | -4 | 4 | 15 | 325 | 315 | 14 |
| 1 | 3 | 13 | 525 | 488 | 28 | -2 | 5 | 13 | 166 | 161 | 18 | -1 | 4 | 14 | 127 | 80 | 12 | 0 | 5 | 15 | 175 | 167 | 11 |
| 2 | 3 | 13 | 73 | 69 | 37 | -1 | 5 | 13 | 41 | 61 | 13 | 2 | 4 | 14 | 887 | 821 | 34 | -1 | 5 | 15 | 331 | 315 | 15 |
| 3 | 3 | 13 | 66 | 175 | 9 | 0 | 5 | 13 | 100 | 106 | 14 | -2 | 4 | 14 | 65 | 168 | 20 | 1 | 5 | 15 | 181 | 176 | 10 |
| 4 | 3 | 13 | 187 | 64 | 26 | 1 | 5 | 13 | 141 | 154 | 40 | 3 | 4 | 14 | 124 | 15 | 30 | 2 | 5 | 15 | 197 | 182 | 12 |
| -4 | 4 | 13 | 65 | 222 | 17 | 2 | 5 | 13 | 129 | 119 | 18 | -3 | 4 | 14 | 60 | 52 | 25 | -2 | 5 | 15 | 105 | 109 | 18 |
| -3 | 4 | 13 | 237 | 300 | 15 | -3 | 5 | 13 | 229 | 206 | 13 | 4 | 4 | 14 | 355 | 357 | 30 | 3 | 5 | 15 | 113 | 111 | 19 |
| -2 | 4 | 13 | 293 | 497 | 13 | -2 | 5 | 13 | 97 | 82 | 14 | -4 | 4 | 14 | 374 | 365 | 28 | -3 | 5 | 15 | 242 | 230 | 20 |
| -1 | 4 | 13 | 501 | 299 | 22 | -1 | 5 | 13 | 60 | 30 | 15 | 0 | 5 | 14 | 104 | 109 | 11 | 4 | 5 | 15 | 334 | 328 | 9 |
| 0 | 4 | 13 | 301 | 223 | 25 | 0 | 5 | 13 | 103 | 82 | 12 | 1 | 5 | 14 | 373 | 364 | 14 | -4 | 5 | 15 | 0 | 47 | 1 |
| 1 | 4 | 13 | 223 | 64 | 38 | 1 | 5 | 13 | 216 | 206 | 20 | -1 | 5 | 14 | 143 | 172 | 10 | 0 | 6 | 15 | 165 | 165 | 9 |
| 2 | 4 | 13 | 81 | 176 | 49 | 2 | 5 | 13 | 131 | 119 | 27 | 2 | 5 | 14 | 64 | 35 | 17 | 1 | 6 | 15 | 62 | 45 | 31 |
| 3 | 4 | 13 | 159 | 87 | 38 | -3 | 5 | 13 | 137 | 128 | 21 | -2 | 5 | 14 | 118 | 123 | 16 | -1 | 6 | 15 | 350 | 328 | 14 |
| 4 | 4 | 13 | 147 | 87 | 49 | -4 | 5 | 13 | 121 | 119 | 21 | 3 | 5 | 14 | 83 | 91 | 19 | 2 | 6 | 15 | 227 | 230 | 10 |
| -4 | 5 | 13 |  |  |  | -1 | 5 | 13 | 154 | 110 | 13 | 4 | 5 | 14 | 93 | 75 | 13 | 3 | 6 | 15 | 89 | 111 | 16 |
|  |  |  |  |  |  |  |  |  |  |  |  | -4 | 5 | 14 | 315 | 315 | 42 |  |  |  |  |  |  |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| -3 | 5 | 13 | 182 | 169 | 11 | 0 | 15 | 13 | 193 | 161 | 10 | 4 | 5 | 14 | 71 | 86 | 50 | -4 | 7 | 15 | 67 | 74 | 40 |
| -2 | 5 | 13 | 298 | 283 | 8 | 1 | 15 | 13 | 92 | 109 | 20 | -4 | 6 | 14 | 91 | 113 | 29 | -3 | 7 | 15 | 83 | 91 | 21 |
| -1 | 5 | 13 | 160 | 168 | 9 | 2 | 15 | 13 | 107 | 119 | 18 | -3 | 6 | 14 | 106 | 114 | 10 | -2 | 7 | 15 | 143 | 123 | 12 |
| 0 | 5 | 13 | 58 | 79 | 17 | 3 | 15 | 13 | 111 | 127 | 15 | -2 | 6 | 14 | 121 | 109 | 9 | -1 | 7 | 15 | 112 | 125 | 55 |
| 1 | 5 | 13 | 158 | 166 | 12 | -3 | 16 | 13 | 65 | 58 | 52 | -1 | 6 | 14 | 452 | 428 | 16 | 0 | 7 | 15 | 139 | 137 | 12 |
| 2 | 5 | 13 | 295 | 281 | 7 | -1 | 16 | 13 | 158 | 152 | 15 | 0 | 6 | 14 | 112 | 109 | 15 | 1 | 7 | 15 | 83 | 61 | 18 |
| 3 | 5 | 13 | 167 | 170 | 12 | 0 | 16 | 13 | 225 | 207 | 9 | 1 | 6 | 14 | 446 | 427 | 9 | 2 | 7 | 15 | 112 | 122 | 21 |
| 4 | 5 | 13 | 71 | 87 | 47 | 1 | 16 | 13 | 171 | 171 | 16 | 2 | 6 | 14 | 127 | 109 | 20 | 3 | 7 | 15 | 60 | 61 | 38 |
| -3 | 6 | 13 | 17 | 21 | 17 | 2 | 16 | 13 | 196 | 207 | 16 | 3 | 6 | 14 | 115 | 115 | 17 | -3 | 8 | 15 | 128 | 138 | 18 |
| -2 | 6 | 13 | 53 | 67 | 17 | -2 | 17 | 13 | 147 | 153 | 16 | 4 | 6 | 14 | 109 | 114 | 15 | -2 | 8 | 15 | 141 | 125 | 14 |
| -1 | 6 | 13 | 153 | 161 | 36 | -1 | 17 | 13 | 68 | 58 | 17 | -3 | 7 | 14 | 103 | 93 | 22 | -1 | 8 | 15 | 128 | 143 | 11 |
| 0 | 6 | 13 | 450 | 417 | 7 | 0 | 17 | 13 | 119 | 107 | 18 | -2 | 7 | 14 | 48 | 34 | 47 | 0 | 8 | 15 | 76 | 101 | 20 |
| 1 | 6 | 13 | 221 | 238 | 20 | -2 | 18 | 13 | 110 | 128 | 12 | -1 | 7 | 14 | 240 | 203 | 8 | 1 | 8 | 15 | 139 | 130 | 14 |
| 2 | 6 | 13 | 452 | 417 | 9 | -1 | 18 | 13 | 114 | 138 | 13 | 0 | 7 | 14 | 112 | 101 | 13 | 2 | 8 | 15 | 110 | 102 | 15 |
| 3 | 6 | 13 | 157 | 162 | 20 | 0 | 18 | 13 | 67 | 69 | 1 | 1 | 7 | 14 | 189 | 209 | 9 | 3 | 8 | 15 | 100 | 142 | 51 |
| -2 | 6 | 13 | 52 | 66 | 18 | -1 | 19 | 13 | 122 | 138 | 15 | 2 | 7 | 14 | 102 | 100 | 17 | -3 | 9 | 15 | 50 | 45 | 42 |
| -1 | 7 | 13 | 52 | 21 | 51 | 0 | 19 | 13 | 129 | 128 | 14 | 3 | 7 | 14 | 253 | 203 | 10 | -2 | 9 | 15 | 195 | 212 | 11 |
| 0 | 7 | 13 | 190 | 196 | 34 | -1 | 20 | 13 | 93 | 106 | 18 | -4 | 8 | 14 | 0 | 35 | 1 | -1 | 9 | 15 | 143 | 172 | 21 |
| 1 | 7 | 13 | 27 | 62 | 16 | 0 | 20 | 13 | 85 | 103 | 15 | -3 | 8 | 14 | 82 | 92 | 17 | 0 | 9 | 15 | 205 | 212 | 12 |
| 2 | 7 | 13 | 362 | 352 | 27 | -1 | 2 | 16 | 171 | 144 | 25 | -2 | 8 | 14 | 65 | 61 | 64 | 1 | 9 | 15 | 88 | 44 | 29 |
| -2 | 7 | 13 | 473 | 475 | 10 | 0 | 2 | 16 | 206 | 186 | 16 | -1 | 8 | 14 | 94 | 77 | 13 | 2 | 9 | 15 | 0 | 1 | 1 |
| -1 | 7 | 13 | 376 | 357 | 17 | 1 | 2 | 16 | 131 | 144 | 14 | 0 | 8 | 14 | 197 | 172 | 8 | 3 | 9 | 15 | 101 | 90 | 21 |
| 0 | 7 | 13 | 488 | 474 | 14 | -2 | 3 | 16 | 67 | 103 | 67 | 1 | 8 | 14 | 0 | 19 | 0 | -2 | 10 | 15 | 0 | 5 | 1 |
| 1 | 7 | 13 | 372 | 352 | 21 | -1 | 3 | 16 | 68 | 76 | 21 | 2 | 8 | 14 | 36 | 43 | 35 | -1 | 10 | 15 | 83 | 90 | 21 |
| 2 | 7 | 13 | 58 | 62 | 11 | 0 | 3 | 16 | 109 | 116 | 13 | 3 | 8 | 14 | 62 | 19 | 62 | 0 | 10 | 15 | 55 | 2 | 55 |
| -4 | 8 | 13 | 199 | 197 | 33 | 1 | 3 | 16 | 209 | 223 | 35 | -3 | 9 | 14 | 205 | 172 | 9 | 1 | 10 | 15 | 95 | 72 | 17 |
| -3 | 8 | 13 | 91 | 68 | 11 | -2 | 4 | 16 | 120 | 116 | 14 | -2 | 9 | 14 | 160 | 77 | 32 | 2 | 10 | 15 | 79 | 6 | 1 |
| -2 | 8 | 13 | 139 | 114 | 29 | -1 | 4 | 16 | 51 | 75 | 50 | -1 | 9 | 14 | 42 | 61 | 42 | -2 | 11 | 15 | 67 | 72 | 21 |
| -1 | 8 | 13 | 260 | 239 | 41 | 0 | 4 | 16 | 0 | 51 | 1 | 0 | 9 | 14 | 117 | 135 | 21 | -1 | 11 | 15 | 42 | 23 | 27 |
| 0 | 8 | 13 | 79 | 60 | 3 | 1 | 4 | 16 | 71 | 42 | 22 | 1 | 9 | 14 | 27 | 35 | 27 | 0 | 11 | 15 | 194 | 162 | 42 |
| 1 | 8 | 13 | 141 | 134 | 19 | 2 | 4 | 16 | 63 | 58 | 37 | 2 | 9 | 14 | 135 | 149 | 9 | 1 | 11 | 15 | 233 | 215 | 12 |
| -4 | 9 | 13 | 81 | 60 | 10 | -2 | 5 | 16 | 78 | 42 | 59 | -3 | 10 | 14 | 224 | 224 | 11 | 2 | 11 | 15 | 30 | 249 | 9 |
| -3 | 9 | 13 | 248 | 239 | 23 | -1 | 5 | 16 | 29 | 51 | 28 | -2 | 10 | 14 | 101 | 106 | 14 | -2 | 12 | 15 | 251 | 247 | 21 |
| -2 | 9 | 13 | 189 | 197 | 11 | 0 | 5 | 16 | 284 | 284 | 9 | -1 | 10 | 14 | 136 | 146 | 9 | -1 | 12 | 15 | 118 | 138 | 12 |
| -1 | 9 | 13 | 0 | 16 | 1 | 1 | 5 | 16 | 391 | 412 | 17 | 0 | 10 | 14 | 206 | 214 | 13 | 0 | 12 | 15 | 108 | 71 | 9 |
| 0 | 9 | 13 | 62 | 60 | 22 | 2 | 5 | 16 | 292 | 314 | 11 | 1 | 10 | 14 | 151 | 83 | 49 | 1 | 12 | 15 | 47 | 12 | 13 |
| 1 | 9 | 13 | 0 | 26 | 1 | -2 | 6 | 16 | 124 | 124 | 11 | 2 | 10 | 14 | 48 | 68 | 47 | -3 | 13 | 15 | 89 | 71 | 12 |
| -4 | 10 | 13 | 109 | 91 | 11 | -1 | 6 | 16 | 57 | 52 | 14 | -3 | 11 | 14 | 107 | 97 | 11 | -2 | 13 | 15 | 78 | 127 | 26 |
| -3 | 10 | 13 | 79 | 84 | 11 | 0 | 6 | 16 | 61 | 69 | 9 | -2 | 11 | 14 | 238 | 241 | 14 | -1 | 13 | 15 | 0 | 51 | 20 |
| -2 | 10 | 13 | 225 | 200 | 29 | 1 | 6 | 16 | 150 | 154 | 12 | -1 | 11 | 14 | 194 | 197 | 9 | 0 | 13 | 15 | 53 | 0 | 1 |
| -1 | 10 | 13 | 184 | 168 | 8 | 2 | 6 | 16 | 375 | 368 | 10 | 0 | 11 | 14 | 259 | 266 | 12 | 1 | 13 | 15 | 184 | 208 | 23 |
| 0 | 10 | 13 | 223 | 200 | 8 | -1 | 7 | 16 | 266 | 278 | 15 | 1 | 11 | 14 | 190 | 198 | 8 | -2 | 14 | 15 | 114 | 38 | 24 |
| 1 | 10 | 13 | 96 | 83 | 19 | 0 | 7 | 16 | 219 | 223 | 15 | 2 | 11 | 14 | 239 | 241 | 16 | -1 | 14 | 15 | 99 | 48 | 23 |
| -3 | 11 | 13 | 73 | 91 | 21 | 1 | 7 | 16 | 265 | 277 | 11 | -2 | 12 | 14 | 102 | 97 | 16 | 0 | 14 | 15 | 79 | 38 | 19 |
| -2 | 11 | 13 | 125 | 127 | 13 | 2 | 7 | 16 | 368 | 368 | 13 | -1 | 12 | 14 | 126 | 115 | 31 | 1 | 14 | 15 | 153 | 207 | 47 |
| -1 | 11 | 13 | 124 | 114 | 20 | -1 | 8 | 16 | 166 | 154 | 9 | 0 | 12 | 14 | 137 | 152 | 13 | -3 | 15 | 15 | 119 | 139 | 19 |
| 0 | 11 | 13 | 171 | 169 | 21 | 0 | 8 | 16 | 75 | 68 | 13 | 1 | 12 | 14 | 261 | 240 | 12 | -2 | 15 | 15 | 141 | 137 | 23 |
| -3 | 12 | 13 | 233 | 215 | 10 | 1 | 8 | 16 | 132 | 138 | 17 | -1 | 13 | 14 | 0 | 10 | 19 | -1 | 15 | 15 | 82 | 54 | 10 |
| 0 | 12 | 13 | 192 | 170 | 8 | -4 | 9 | 16 | 88 | 107 | 20 | 0 | 13 | 14 | 257 | 239 | 12 | 0 | 15 | 15 | 150 | 137 | 12 |
| 1 | 12 | 13 | | | | | | | | | | 1 | 13 | 14 | 108 | 134 | 19 | | | | | | |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 2 | 12 | 15 | 114 | 113 | 16 | 2 | 4 | 16 | 199 | 198 | 9 | -3 | 6 | 16 | 136 | 152 | 14 | 2 | 17 | 17 | 129 | 139 | 84 |
| 3 | 12 | 15 | 121 | 128 | 12 | 3 | 4 | 16 | 420 | 415 | 16 | -2 | 6 | 16 | 91 | 115 | 17 | -2 | 17 | 17 | 146 | 148 | 15 |
| -3 | 13 | 15 | 101 | 89 | 36 | -3 | 4 | 16 | 426 | 432 | 15 | -1 | 6 | 16 | 62 | 40 | 62 | -1 | 18 | 17 | 48 | 54 | 48 |
| -2 | 13 | 15 | 143 | 128 | 11 | -2 | 4 | 16 | 439 | 415 | 18 | 0 | 6 | 16 | 87 | 107 | 26 | 0 | 18 | 17 | 0 | 40 | 1 |
| -1 | 13 | 15 | 89 | 71 | 16 | -1 | 4 | 16 | 193 | 199 | 8 | 1 | 6 | 16 | 172 | 142 | 10 | 1 | 18 | 17 | 39 | 55 | 38 |
| 0 | 13 | 15 | 185 | 163 | 10 | 0 | 4 | 16 | 104 | 108 | 18 | 2 | 6 | 16 | 0 | 15 | 1 | 2 | 18 | 17 | 170 | 149 | 17 |
| 1 | 13 | 15 | 94 | 72 | 18 | 1 | 4 | 16 | 124 | 138 | 18 | 3 | 6 | 16 | 155 | 141 | 13 | -2 | 19 | 17 | 5 | 58 | 4 |
| 2 | 13 | 15 | 116 | 128 | 17 | 2 | 4 | 16 | 76 | 41 | 31 | -4 | 7 | 16 | 96 | 107 | 21 | -1 | 19 | 17 | 63 | 18 | 23 |
| -3 | 14 | 15 | 83 | 89 | 17 | -3 | 5 | 16 | 223 | 216 | 14 | -3 | 7 | 16 | 57 | 40 | 13 | 0 | 19 | 17 | 60 | 91 | 34 |
| -2 | 14 | 15 | 87 | 91 | 21 | -2 | 5 | 16 | 45 | 40 | 45 | -2 | 7 | 16 | 38 | 49 | 21 | 1 | 19 | 17 | 0 | 19 | 1 |
| -1 | 14 | 15 | 238 | 263 | 12 | -1 | 5 | 16 | 220 | 212 | 10 | -1 | 7 | 16 | 133 | 120 | 38 | 2 | 19 | 17 | 67 | 58 | 54 |
| 0 | 14 | 15 | 226 | 210 | 9 | 0 | 5 | 16 | 39 | 19 | 39 | 0 | 7 | 16 | 274 | 273 | 37 | -1 | 20 | 17 | 51 | 32 | 50 |
| 1 | 14 | 15 | 215 | 182 | 15 | 1 | 5 | 16 | 213 | 213 | 17 | 1 | 7 | 16 | 61 | 59 | 21 | 0 | 20 | 17 | 139 | 130 | 12 |
| -3 | 15 | 15 | 215 | 209 | 15 | -3 | 6 | 16 | 61 | 39 | 61 | 2 | 7 | 16 | 280 | 272 | 10 | 1 | 20 | 17 | 45 | 32 | 45 |
| -2 | 15 | 15 | 237 | 263 | 16 | -2 | 6 | 16 | 210 | 216 | 12 | -4 | 8 | 16 | 91 | 120 | 30 | 2 | 20 | 17 | 0 | 3 | 1 |
| -1 | 15 | 15 | 113 | 90 | 17 | -1 | 6 | 16 | 60 | 41 | 38 | -3 | 8 | 16 | 188 | 184 | 15 | -3 | 0 | 18 | 125 | 87 | 18 |
| 0 | 15 | 15 | 76 | 54 | 32 | 0 | 6 | 16 | 109 | 110 | 18 | -2 | 8 | 16 | 151 | 135 | 14 | -2 | 0 | 18 | 64 | 78 | 23 |
| 1 | 15 | 15 | 95 | 65 | 13 | 1 | 6 | 16 | 290 | 283 | 13 | -1 | 8 | 16 | 33 | 55 | 15 | -1 | 1 | 18 | 225 | 235 | 7 |
| 2 | 15 | 15 | 131 | 112 | 15 | 2 | 6 | 16 | 115 | 116 | 11 | 0 | 8 | 16 | 50 | 69 | 32 | 0 | 1 | 18 | 210 | 173 | 10 |
| -3 | 15 | 15 | 295 | 251 | 16 | -3 | 7 | 16 | 349 | 355 | 13 | 1 | 8 | 16 | 204 | 195 | 16 | 1 | 1 | 18 | 142 | 217 | 20 |
| -1 | 15 | 15 | 145 | 113 | 15 | -2 | 7 | 16 | 189 | 189 | 9 | 2 | 8 | 16 | 164 | 167 | 9 | -3 | 2 | 18 | 110 | 121 | 23 |
| 1 | 15 | 15 | 74 | 65 | 73 | -1 | 7 | 16 | 356 | 355 | 16 | 3 | 8 | 16 | 181 | 166 | 16 | -2 | 2 | 18 | 313 | 294 | 22 |
| 3 | 15 | 15 | 96 | 54 | 16 | 0 | 7 | 16 | 117 | 117 | 15 | -3 | 9 | 16 | 193 | 193 | 15 | -1 | 2 | 18 | 98 | 95 | 10 |
| -3 | 16 | 15 | 118 | 102 | 20 | 1 | 7 | 16 | 302 | 283 | 14 | -2 | 9 | 16 | 177 | 165 | 8 | 0 | 2 | 18 | 51 | 55 | 34 |
| -2 | 16 | 15 | 180 | 224 | 22 | 2 | 7 | 16 | 109 | 111 | 21 | -1 | 9 | 16 | 180 | 167 | 9 | 1 | 2 | 18 | 139 | 126 | 9 |
| -1 | 16 | 15 | 240 | 232 | 9 | -4 | 8 | 16 | 47 | 67 | 47 | 0 | 9 | 16 | 216 | 195 | 10 | -2 | 3 | 18 | 77 | 55 | 33 |
| 0 | 16 | 15 | 43 | 18 | 43 | -3 | 8 | 16 | 310 | 313 | 11 | 1 | 9 | 16 | 40 | 69 | 39 | -1 | 3 | 18 | 98 | 94 | 9 |
| 1 | 16 | 15 | 229 | 232 | 14 | -2 | 8 | 16 | 175 | 171 | 8 | 2 | 9 | 16 | 27 | 44 | 27 | 0 | 3 | 18 | 303 | 295 | 12 |
| 2 | 16 | 15 | 187 | 224 | 31 | -1 | 8 | 16 | 88 | 102 | 18 | -3 | 9 | 16 | 288 | 308 | 12 | 1 | 3 | 18 | 126 | 121 | 12 |
| -3 | 16 | 15 | 97 | 102 | 17 | 0 | 8 | 16 | 158 | 176 | 10 | -2 | 9 | 16 | 54 | 69 | 51 | -3 | 4 | 18 | 120 | 135 | 31 |
| -1 | 17 | 15 | 86 | 86 | 14 | 1 | 8 | 16 | 109 | 101 | 17 | -1 | 9 | 16 | 105 | 88 | 19 | -2 | 4 | 18 | 185 | 176 | 17 |
| 0 | 17 | 15 | 0 | 6 | 1 | 2 | 8 | 16 | 173 | 170 | 9 | 0 | 9 | 16 | 465 | 487 | 15 | -1 | 4 | 18 | 103 | 108 | 10 |
| 1 | 17 | 15 | 313 | 305 | 13 | -3 | 9 | 16 | 315 | 314 | 12 | 1 | 9 | 16 | 104 | 89 | 11 | 0 | 4 | 18 | 189 | 202 | 27 |
| -2 | 17 | 15 | 46 | 6 | 46 | -2 | 9 | 16 | 53 | 67 | 28 | 2 | 9 | 16 | 85 | 70 | 36 | 1 | 4 | 18 | 769 | 776 | 12 |
| -1 | 18 | 15 | 54 | 86 | 54 | -1 | 9 | 16 | 87 | 64 | 28 | -3 | 10 | 16 | 305 | 308 | 14 | -2 | 5 | 18 | 196 | 202 | 9 |
| 0 | 18 | 15 | 66 | 94 | 21 | 0 | 9 | 16 | 223 | 232 | 9 | -2 | 10 | 16 | 43 | 44 | 42 | -1 | 5 | 18 | 113 | 108 | 7 |
| 1 | 18 | 15 | 118 | 112 | 13 | 1 | 9 | 16 | 163 | 153 | 10 | -1 | 10 | 16 | 101 | 89 | 12 | 0 | 5 | 18 | 190 | 176 | 14 |
| -2 | 18 | 15 | 98 | 277 | 22 | 2 | 9 | 16 | 209 | 226 | 10 | 0 | 10 | 16 | 121 | 124 | 13 | 1 | 5 | 18 | 146 | 135 | 21 |
| -1 | 19 | 15 | 269 | 112 | 14 | -3 | 10 | 16 | 205 | 204 | 10 | 1 | 10 | 16 | 178 | 177 | 9 | -2 | 6 | 18 | 97 | 95 | 8 |
| 0 | 19 | 15 | 123 | 89 | 27 | -2 | 10 | 16 | 225 | 227 | 10 | -3 | 10 | 16 | 147 | 205 | 17 | -1 | 6 | 18 | 249 | 218 | 16 |
| 1 | 19 | 15 | 79 | 94 | 47 | -1 | 10 | 16 | 161 | 152 | 24 | -2 | 10 | 16 | 180 | 177 | 8 | 0 | 6 | 18 | 239 | 247 | 12 |
| -2 | 19 | 15 | 57 | 38 | 26 | 0 | 10 | 16 | 208 | 232 | 10 | -1 | 10 | 16 | 103 | 124 | 17 | 1 | 6 | 18 | 207 | 227 | 10 |
| -1 | 19 | 15 | 47 | 59 | 24 | 1 | 10 | 16 | 61 | 64 | 24 | 0 | 10 | 16 | 72 | 88 | 24 | -2 | 7 | 18 | 216 | 238 | 12 |
| 0 | 19 | 15 | 68 | 44 | 26 | -3 | 11 | 16 | 59 | 69 | 58 | 1 | 10 | 16 | 173 | 179 | 18 | -1 | 7 | 18 | 202 | 226 | 7 |
| 2 | 19 | 15 | 73 | 58 | 1 | -2 | 11 | 16 | 97 | 91 | 12 | -3 | 11 | 16 | 88 | 28 | 19 | 0 | 7 | 18 | 229 | 247 | 10 |
| -2 | 20 | 15 | 0 | 37 | 35 | -1 | 11 | 16 | 129 | 134 | 13 | -2 | 11 | 16 | 145 | 132 | 9 | 1 | 7 | 18 | 233 | 218 | 12 |
| -1 | 20 | 15 | 161 | 108 | 16 | 0 | 11 | 16 | 143 | 118 | 8 | -1 | 11 | 16 | 139 | 72 | 56 | -1 | 8 | 18 | 100 | 95 | 50 |
| 0 | 20 | 15 | 92 | 104 | 1 | 1 | 11 | 16 | 94 | 73 | 14 | 0 | 11 | 16 | 25 | 132 | 10 | 0 | 8 | 18 | 51 | 80 | 11 |
| 1 | 20 | 15 | 82 | 104 | 37 | 2 | 11 | 16 | 127 | 119 | 10 | 1 | 11 | 16 | 133 | 180 | 13 | 1 | 8 | 18 | 174 | 145 | 12 |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| -1 | 0 | 21 | 15 | 27 | 7 | 27 | 2 | 9 | 16 | 141 | 133 | 11 | -3 | 1 | 17 | 154 | 155 | 11 | -2 | 4 | 18 | 252 | 239 | 9 |
| -0 | 0 | 21 | 15 | 8 | 21 | 8 | 3 | 9 | 16 | 71 | 92 | 23 | -2 | 2 | 17 | 223 | 243 | 22 | -1 | 4 | 18 | 283 | 293 | 14 |
| 1 | 0 | 21 | 15 | 34 | 6 | 34 | -4 | 9 | 16 | 70 | 69 | 26 | -1 | 2 | 17 | 280 | 273 | 18 | 0 | 4 | 18 | 172 | 167 | 9 |
| -0 | 0 | 22 | 15 | 31 | 24 | 31 | -3 | 9 | 16 | 98 | 100 | 25 | 0 | 2 | 17 | 120 | 105 | 9 | 1 | 4 | 18 | 278 | 292 | 15 |
| 0 | 0 | 22 | 15 | 163 | 155 | 11 | -2 | 9 | 16 | 0 | 58 | 1 | 1 | 2 | 17 | 127 | 145 | 11 | 2 | 4 | 18 | 234 | 239 | 9 |
| 0 | 1 | 16 | 16 | 259 | 267 | 6 | -1 | 9 | 16 | 160 | 165 | 11 | 2 | 2 | 17 | 315 | 318 | 12 | 3 | 4 | 18 | 172 | 146 | 19 |
| 1 | 1 | 16 | 16 | 37 | 6 | 37 | 0 | 9 | 16 | 98 | 56 | 13 | -3 | 3 | 17 | 118 | 145 | 39 | 4 | 4 | 18 | 62 | 81 | 61 |
| 2 | 2 | 0 | 16 | 32 | 57 | 31 | 1 | 9 | 16 | 291 | 295 | 12 | -2 | 3 | 17 | 104 | 106 | 8 | -3 | 4 | 18 | 53 | 54 | 52 |
| 3 | 3 | 0 | 16 | 157 | 198 | 31 | 2 | 9 | 16 | 72 | 57 | 17 | -1 | 3 | 17 | 296 | 274 | 11 | -2 | 4 | 18 | 144 | 153 | 12 |
| 4 | 4 | 1 | 16 | 62 | 84 | 54 | 3 | 9 | 16 | 160 | 164 | 18 | 0 | 3 | 17 | 262 | 243 | 19 | -1 | 5 | 18 | 96 | 93 | 20 |
| -3 | -1 | 1 | 16 | 71 | 63 | 9 | -4 | 10 | 16 | 84 | 59 | 19 | 1 | 3 | 17 | 110 | 121 | 20 | 0 | 5 | 18 | 182 | 197 | 11 |
| -2 | 1 | 16 | 308 | 287 | 10 | -3 | 10 | 16 | 94 | 101 | 20 | 2 | 3 | 17 | 213 | 183 | 31 | 1 | 5 | 18 | 271 | 283 | 17 |
| -1 | 1 | 16 | 140 | 136 | 38 | -2 | 10 | 16 | 84 | 99 | 14 | -3 | 4 | 17 | 219 | 194 | 7 | 2 | 5 | 18 | 199 | 197 | 14 |
| 0 | 1 | 16 | 39 | 28 | 12 | -1 | 10 | 16 | 0 | 9 | 1 | -2 | 4 | 17 | 311 | 316 | 12 | -3 | 5 | 18 | 92 | 93 | 15 |
| 1 | 1 | 16 | 67 | 51 | 13 | 0 | 10 | 16 | 60 | 39 | 26 | -1 | 4 | 17 | 155 | 141 | 9 | -2 | 5 | 18 | 143 | 152 | 11 |
| 2 | 1 | 16 | 135 | 137 | 12 | 1 | 10 | 16 | 205 | 205 | 10 | 0 | 4 | 17 | 309 | 315 | 15 | -1 | 5 | 18 | 0 | 54 | 1 |
| 3 | 2 | 16 | 318 | 286 | 13 | -4 | 11 | 16 | 214 | 98 | 17 | 1 | 4 | 17 | 195 | 195 | 7 | 0 | 6 | 18 | 35 | 72 | 34 |
| -4 | 2 | 16 | 74 | 62 | 19 | -3 | 11 | 16 | 56 | 68 | 22 | 2 | 4 | 17 | 198 | 183 | 11 | 1 | 6 | 18 | 238 | 264 | 12 |
| -3 | 2 | 16 | 100 | 84 | 15 | -2 | 11 | 16 | 48 | 84 | 30 | -4 | 5 | 17 | 139 | 121 | 22 | 2 | 6 | 18 | 121 | 130 | 23 |
| -2 | 2 | 16 | 67 | 51 | 40 | -1 | 11 | 16 | 83 | 213 | 1 | -3 | 5 | 17 | 91 | 67 | 30 | -3 | 6 | 18 | 133 | 123 | 12 |
| -1 | 2 | 16 | 116 | 124 | 15 | 0 | 11 | 16 | 62 | 68 | 28 | -2 | 5 | 17 | 0 | 46 | 1 | -2 | 6 | 18 | 52 | 53 | 51 |
| 0 | 2 | 16 | 291 | 314 | 8 | 1 | 11 | 16 | 151 | 84 | 8 | -1 | 5 | 17 | 26 | 40 | 26 | -1 | 6 | 18 | 123 | 122 | 9 |
| 1 | 2 | 16 | 406 | 410 | 19 | -4 | 12 | 16 | 226 | 213 | 39 | 0 | 5 | 17 | 54 | 60 | 29 | 0 | 6 | 18 | 71 | 73 | 21 |
| 2 | 2 | 16 | 124 | 129 | 11 | -3 | 12 | 16 | 65 | 64 | 22 | 1 | 5 | 17 | 130 | 123 | 16 | 1 | 6 | 18 | 136 | 127 | 12 |
| 3 | 2 | 16 | 269 | 264 | 15 | -2 | 12 | 16 | 72 | 40 | 13 | 2 | 5 | 17 | 111 | 111 | 13 | 2 | 6 | 18 | 289 | 258 | 14 |
| 4 | 2 | 16 | 69 | 71 | 31 | -1 | 12 | 16 | 48 | 64 | 48 | -3 | 6 | 18 | 195 | 184 | 10 | -3 | 6 | 18 | 141 | 127 | 17 |
| -4 | 3 | 16 | 71 | 75 | 37 | 0 | 12 | 16 | 63 | 54 | 28 | -2 | 6 | 18 | 136 | 112 | 9 | -2 | 6 | 18 | 0 | 73 | 1 |
| -3 | 3 | 16 | 230 | 231 | 12 | 1 | 12 | 16 | 105 | 70 | 17 | -1 | 6 | 18 | 203 | 123 | 32 | -1 | 7 | 18 | 64 | 62 | 27 |
| -2 | 3 | 16 | 110 | 106 | 15 | -3 | 13 | 16 | 164 | 176 | 7 | 0 | 6 | 18 | 31 | 40 | 30 | 0 | 7 | 18 | 118 | 124 | 13 |
| -1 | 3 | 16 | 62 | 53 | 43 | -2 | 13 | 16 | 66 | 19 | 30 | 1 | 6 | 18 | 91 | 105 | 14 | 1 | 7 | 18 | 124 | 122 | 18 |
| 0 | 3 | 16 | 110 | 69 | 17 | -1 | 13 | 16 | 64 | 37 | 37 | 2 | 6 | 18 | 157 | 157 | 11 | 2 | 7 | 18 | 469 | 461 | 19 |
| 1 | 3 | 16 | 103 | 106 | 14 | 0 | 13 | 16 | 51 | 79 | 51 | -3 | 7 | 18 | 212 | 230 | 8 | -3 | 7 | 18 | 99 | 122 | 18 |
| 2 | 3 | 16 | 243 | 232 | 37 | 1 | 13 | 16 | 266 | 268 | 17 | -2 | 7 | 18 | 116 | 91 | 19 | -2 | 7 | 18 | 104 | 124 | 20 |
| 3 | 3 | 16 | 83 | 76 | 14 | -2 | 0 | 18 | 80 | 71 | 22 | -1 | 7 | 18 | 240 | 230 | 11 | -1 | 8 | 20 | 99 | 78 | 23 |
| -4 | 4 | 16 | 110 | 115 | 10 | -1 | 0 | 18 | 42 | 71 | 42 | 0 | 7 | 18 | 138 | 158 | 20 | 0 | 8 | 20 | 155 | 170 | 10 |
| -3 | 4 | 16 | 172 | 156 | 25 | 0 | 0 | 18 | 205 | 231 | 12 | 1 | 7 | 18 | 209 | 180 | 14 | 1 | 8 | 20 | 211 | 253 | 13 |
| -2 | 4 | 16 | 117 | 116 | 14 | -3 | 1 | 18 | 95 | 69 | 18 | 2 | 7 | 18 | 101 | 106 | 17 | 2 | 8 | 20 | 157 | 170 | 15 |
| -1 | 4 | 16 | 270 | 227 | 20 | -2 | 1 | 18 | 91 | 79 | 10 | -3 | 8 | 18 | 75 | 79 | 20 | -3 | 8 | 20 | 74 | 77 | 73 |
| 0 | 4 | 16 | 174 | 150 | 23 | -1 | 1 | 18 | 267 | 269 | 33 | -2 | 8 | 18 | 202 | 183 | 18 | -2 | 8 | 20 | 62 | 55 | 25 |
| 1 | 4 | 16 | 351 | 339 | 8 | 0 | 1 | 18 | 89 | 79 | 22 | -1 | 8 | 18 | 314 | 301 | 1 | -1 | 8 | 20 | 45 | 64 | 44 |
| 2 | 4 | 16 | 181 | 181 | 1 | 1 | 1 | 18 | 69 | 30 | 11 | 0 | 8 | 18 | 209 | 180 | 17 | 0 | 8 | 20 | 59 | 87 | 59 |
| 3 | 4 | 16 | 257 | 227 | 17 | -3 | 2 | 18 | 298 | 256 | 33 | 1 | 8 | 18 | 312 | 301 | 20 | 1 | 9 | 20 | 61 | 64 | 32 |
| -3 | 5 | 16 | 139 | 116 | 14 | -2 | 2 | 18 | 105 | 94 | 22 | 2 | 8 | 18 | 148 | 183 | 18 | 2 | 9 | 20 | 81 | 55 | 80 |
| -2 | 5 | 16 | 66 | 60 | 25 | -1 | 2 | 18 | 86 | 514 | 11 | -3 | 9 | 18 | 76 | 79 | 11 | -3 | 9 | 20 | 17 | 46 | 31 |
| -1 | 5 | 16 | 87 | 65 | 14 | 0 | 2 | 18 | 504 | 94 | 22 | -2 | 9 | 18 | 154 | 148 | 20 | -2 | 9 | 20 | 32 | 67 | 16 |
| 0 | 5 | 16 | 210 | 178 | 20 | 1 | 2 | 18 | 84 | 103 | 11 | -1 | 9 | 18 | 126 | 136 | 17 | -1 | 9 | 20 | 0 | 9 | 1 |
| 1 | 5 | 16 | 0 | 38 | 1 | -3 | 3 | 18 | 113 | 256 | 14 | 0 | 9 | 18 | 89 | 88 | 20 | 0 | 0 | 20 | 67 | 67 | 31 |
| 2 | 5 | 16 | 195 | 179 | 52 | -2 | 3 | 18 | 274 | 103 | 17 | 1 | 9 | 18 | 0 | 56 | 1 | 1 | 0 | 20 | 108 | 80 | 12 |
| -3 | 9 | 18 | 52 | 64 | 22 | -1 | 3 | 18 | 36 | 32 | 36 | 2 | 9 | 18 | 107 | 88 | 17 | 2 | 0 | 20 | 23 | 13 | 22 |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 3 | 9 | 18 | 71 | 59 | 20 | -4 | 3 | 19 | 96 | 115 | 20 | 3 | 13 | 19 | 120 | 148 | 13 | 1 | 19 | 20 | 79 | 90 | 19 | 1 | 0 | 21 | 61 | 80 | 60 |
| -3 | 10 | 18 | 184 | 180 | 8 | -3 | 3 | 19 | 270 | 277 | 14 | -3 | 14 | 19 | 94 | 96 | 24 | -2 | 6 | 20 | 105 | 95 | 15 | 0 | 0 | 21 | 42 | 75 | 42 |
| -2 | 10 | 18 | 147 | 140 | 12 | -2 | 3 | 19 | 70 | 76 | 17 | -2 | 14 | 19 | 144 | 133 | 19 | -1 | 6 | 20 | 94 | 77 | 13 | -1 | 1 | 21 | 0 | 49 | 1 |
| -1 | 10 | 18 | 96 | 83 | 14 | -1 | 3 | 19 | 191 | 205 | 10 | -1 | 14 | 19 | 202 | 216 | 9 | 0 | 6 | 20 | 123 | 123 | 15 | 2 | 1 | 21 | 44 | 18 | 43 |
| 0 | 10 | 18 | 307 | 295 | 23 | 0 | 3 | 19 | 248 | 244 | 20 | 0 | 14 | 19 | 499 | 461 | 20 | 1 | 6 | 20 | 124 | 76 | 15 | 3 | 1 | 21 | 75 | 75 | 21 |
| 1 | 10 | 18 | 83 | 84 | 13 | 1 | 3 | 19 | 190 | 205 | 18 | 1 | 14 | 19 | 192 | 215 | 12 | 2 | 6 | 20 | 109 | 95 | 13 | 4 | 1 | 21 | 0 | 37 | 1 |
| 2 | 10 | 18 | 143 | 141 | 11 | 2 | 3 | 19 | 69 | 77 | 12 | 2 | 14 | 19 | 120 | 134 | 15 | -4 | 7 | 20 | 68 | 91 | 50 | -4 | 2 | 21 | 52 | 46 | 52 |
| 3 | 10 | 18 | 142 | 181 | 15 | 3 | 3 | 19 | 297 | 278 | 15 | 3 | 14 | 19 | 56 | 96 | 18 | -3 | 7 | 20 | 92 | 86 | 18 | -3 | 2 | 21 | 95 | 96 | 40 |
| -3 | 11 | 18 | 97 | 57 | 12 | -3 | 4 | 19 | 121 | 116 | 10 | -3 | 15 | 19 | 98 | 91 | 27 | -2 | 7 | 20 | 153 | 117 | 15 | -2 | 2 | 21 | 185 | 180 | 8 |
| -2 | 11 | 18 | 66 | 63 | 28 | -2 | 4 | 19 | 70 | 40 | 30 | -2 | 15 | 19 | 184 | 175 | 15 | -1 | 7 | 20 | 97 | 84 | 38 | -1 | 2 | 21 | 96 | 67 | 29 |
| -1 | 11 | 18 | 143 | 136 | 10 | -1 | 4 | 19 | 193 | 183 | 12 | -1 | 15 | 19 | 39 | 12 | 38 | 0 | 7 | 20 | 38 | 57 | 15 | 0 | 2 | 21 | 315 | 327 | 11 |
| 0 | 11 | 18 | 51 | 7 | 50 | 0 | 4 | 19 | 165 | 156 | 10 | 0 | 15 | 19 | 356 | 321 | 15 | 1 | 7 | 20 | 116 | 108 | 11 | 2 | 2 | 21 | 80 | 66 | 23 |
| 1 | 11 | 18 | 131 | 135 | 10 | 1 | 4 | 19 | 210 | 209 | 28 | 1 | 15 | 19 | 66 | 12 | 30 | 2 | 7 | 20 | 216 | 197 | 13 | -3 | 3 | 21 | 178 | 181 | 7 |
| 2 | 11 | 18 | 22 | 63 | 21 | 2 | 4 | 19 | 166 | 144 | 12 | 2 | 15 | 19 | 173 | 175 | 48 | -3 | 8 | 20 | 105 | 109 | 12 | -2 | 3 | 21 | 111 | 97 | 14 |
| 3 | 11 | 18 | 66 | 57 | 36 | 3 | 4 | 19 | 232 | 209 | 9 | 3 | 15 | 19 | 73 | 90 | 26 | -2 | 8 | 20 | 17 | 57 | 16 | -1 | 3 | 21 | 88 | 46 | 22 |
| -3 | 12 | 18 | 82 | 63 | 14 | -3 | 5 | 19 | 164 | 156 | 6 | -3 | 16 | 19 | 81 | 93 | 24 | -1 | 8 | 20 | 73 | 84 | 20 | 0 | 3 | 21 | 106 | 133 | 23 |
| -2 | 12 | 18 | 179 | 177 | 13 | -2 | 5 | 19 | 207 | 183 | 9 | -2 | 16 | 19 | 62 | 33 | 34 | 0 | 8 | 20 | 103 | 117 | 17 | 2 | 3 | 21 | 210 | 218 | 12 |
| -1 | 12 | 18 | 126 | 126 | 11 | -1 | 5 | 19 | 0 | 40 | 43 | -1 | 16 | 19 | 300 | 288 | 28 | 1 | 8 | 20 | 85 | 93 | 15 | -2 | 4 | 21 | 11 | 31 | 11 |
| 0 | 12 | 18 | 101 | 75 | 18 | 0 | 5 | 19 | 43 | 52 | 23 | 0 | 16 | 19 | 54 | 33 | 53 | 2 | 8 | 20 | 165 | 139 | 16 | -1 | 4 | 21 | 40 | 89 | 40 |
| 1 | 12 | 18 | 139 | 127 | 16 | 1 | 5 | 19 | 73 | 70 | 10 | 1 | 16 | 19 | 87 | 94 | 75 | -3 | 9 | 20 | 207 | 216 | 8 | 0 | 4 | 21 | 92 | 74 | 14 |
| -3 | 13 | 18 | 161 | 177 | 12 | -3 | 6 | 19 | 258 | 253 | 10 | -3 | 17 | 19 | 52 | 69 | 51 | -2 | 9 | 20 | 86 | 83 | 16 | -3 | 5 | 21 | 90 | 88 | 13 |
| -2 | 13 | 18 | 42 | 63 | 41 | -2 | 6 | 19 | 142 | 123 | 21 | -2 | 17 | 19 | 0 | 6 | 1 | -1 | 9 | 20 | 212 | 215 | 11 | -2 | 5 | 21 | 53 | 31 | 21 |
| -1 | 13 | 18 | 62 | 69 | 41 | -1 | 6 | 19 | 59 | 59 | 18 | -1 | 17 | 19 | 105 | 94 | 18 | 0 | 9 | 20 | 140 | 139 | 12 | -1 | 5 | 21 | 206 | 218 | 24 |
| 0 | 13 | 18 | 198 | 198 | 11 | 0 | 6 | 19 | 129 | 123 | 6 | 0 | 17 | 19 | 0 | 6 | 1 | 1 | 9 | 20 | 67 | 93 | 20 | 0 | 5 | 21 | 122 | 133 | 10 |
| 1 | 13 | 18 | 282 | 267 | 10 | 1 | 6 | 19 | 256 | 253 | 9 | 1 | 17 | 19 | 82 | 69 | 34 | 2 | 9 | 20 | 118 | 109 | 10 | -2 | 6 | 21 | 97 | 99 | 22 |
| -3 | 14 | 18 | 105 | 104 | 21 | -3 | 7 | 19 | 48 | 70 | 47 | -2 | 0 | 20 | 0 | 5 | 1 | -3 | 10 | 20 | 178 | 168 | 10 | -1 | 6 | 21 | 104 | 107 | 29 |
| -2 | 14 | 18 | 289 | 267 | 27 | -2 | 7 | 19 | 73 | 52 | 27 | -1 | 0 | 20 | 173 | 164 | 11 | -2 | 10 | 20 | 274 | 263 | 9 | 0 | 6 | 21 | 137 | 126 | 11 |
| -1 | 14 | 18 | 152 | 198 | 38 | -1 | 7 | 19 | 70 | 67 | 11 | 0 | 0 | 20 | 41 | 5 | 41 | -1 | 10 | 20 | 35 | 25 | 34 | -3 | 7 | 21 | 71 | 63 | 19 |
| 0 | 14 | 18 | 70 | 70 | 16 | 0 | 7 | 19 | 101 | 131 | 41 | -2 | 1 | 20 | 53 | 26 | 53 | 0 | 10 | 20 | 270 | 264 | 9 | -2 | 7 | 21 | 177 | 170 | 15 |
| 1 | 14 | 18 | 66 | 62 | 22 | 1 | 7 | 19 | 135 | 140 | 53 | -1 | 1 | 20 | 57 | 71 | 35 | 1 | 10 | 20 | 145 | 169 | 13 | -1 | 7 | 21 | 91 | 64 | 22 |
| -3 | 15 | 18 | 76 | 81 | 29 | -3 | 8 | 19 | 271 | 277 | 24 | 0 | 1 | 20 | 71 | 86 | 24 | -3 | 11 | 20 | 68 | 108 | 20 | 0 | 7 | 21 | 131 | 125 | 7 |
| -2 | 15 | 18 | 179 | 162 | 10 | -2 | 8 | 19 | 488 | 460 | 23 | -2 | 2 | 20 | 60 | 71 | 59 | -2 | 11 | 20 | 101 | 85 | 22 | -3 | 8 | 21 | 91 | 107 | 16 |
| -1 | 15 | 18 | 250 | 224 | 11 | -1 | 8 | 19 | 277 | 277 | 9 | -1 | 2 | 20 | 97 | 107 | 12 | -1 | 11 | 20 | 95 | 71 | 10 | -2 | 8 | 21 | 109 | 99 | 10 |
| 0 | 15 | 18 | 177 | 162 | 16 | 0 | 8 | 19 | 127 | 140 | 13 | 0 | 2 | 20 | 88 | 82 | 13 | 0 | 11 | 20 | 163 | 141 | 15 | -1 | 8 | 21 | 0 | 54 | 1 |
| 1 | 15 | 18 | 68 | 81 | 17 | 1 | 8 | 19 | 131 | 131 | 10 | 1 | 2 | 20 | 90 | 106 | 11 | 1 | 11 | 20 | 144 | 145 | 21 | 0 | 8 | 21 | 34 | 49 | 33 |
| -3 | 16 | 18 | 64 | 62 | 32 | -3 | 9 | 19 | 59 | 67 | 17 | -3 | 3 | 20 | 468 | 470 | 30 | -3 | 12 | 20 | 161 | 141 | 13 | -3 | 9 | 21 | 165 | 152 | 11 |
| -2 | 16 | 18 | 240 | 264 | 19 | -2 | 9 | 19 | 184 | 177 | 32 | -2 | 3 | 20 | 136 | 119 | 18 | -2 | 12 | 20 | 70 | 71 | 14 | -2 | 9 | 21 | 115 | 97 | 15 |
| -1 | 16 | 18 | 116 | 108 | 12 | -1 | 9 | 19 | 101 | 102 | 15 | -1 | 3 | 20 | 230 | 227 | 8 | -1 | 12 | 20 | 83 | 85 | 23 | -1 | 9 | 21 | 71 | 61 | 21 |
| 0 | 16 | 18 | 64 | 62 | 14 | 0 | 9 | 19 | 242 | 228 | 11 | 0 | 3 | 20 | 321 | 299 | 1 | 0 | 12 | 20 | 70 | 67 | 26 | 0 | 9 | 21 | 116 | 97 | 11 |
| 1 | 16 | 18 | 66 | 104 | 26 | 1 | 9 | 19 | 181 | 169 | 14 | -3 | 4 | 20 | 0 | 38 | 1 | -3 | 13 | 20 | 105 | 113 | 25 | -3 | 10 | 21 | 163 | 152 | 7 |
| -2 | 16 | 18 | 156 | 131 | 17 | -3 | 10 | 19 | 102 | 93 | 30 | -2 | 4 | 20 | 87 | 70 | 26 | -2 | 13 | 20 | 234 | 234 | 13 | -2 | 10 | 21 | 68 | 49 | 21 |
| -2 | 16 | 18 | 131 | 107 | 21 | -2 | 10 | 19 | 161 | 168 | 18 | -1 | 4 | 20 | 160 | 138 | 17 | -1 | 13 | 20 | 129 | 114 | 14 | -1 | 10 | 21 | 39 | 54 | 20 |
| -1 | 16 | 18 | 254 | 263 | 17 | -1 | 10 | 19 | 229 | 228 | 13 | 0 | 4 | 20 | 76 | 74 | 15 | 0 | 13 | 20 | 68 | 63 | 13 | 0 | 10 | 21 | 104 | 40 | 39 |
| 2 | 16 | 18 | 90 | 104 | 27 | 1 | 10 | 19 | 100 | 101 | 14 | -3 | 5 | 20 | 108 | 101 | 14 | -3 | 14 | 20 | 61 | 67 | 26 | -3 | 11 | 21 | 86 | 122 | 14 |
| -2 | 16 | 18 | 108 | 96 | 19 | -3 | 11 | 19 | 108 | 115 | 16 | -2 | 5 | 20 | 310 | 319 | 30 | -2 | 14 | 20 | 39 | 64 | 15 | -2 | 11 | 21 | 347 | 332 | 19 |
| -1 | 16 | 18 | 118 | 115 | 14 | -2 | 11 | 19 | 229 | 228 | 10 | -1 | 5 | 20 | 130 | 102 | 18 | -1 | 14 | 20 | 115 | 125 | 10 | -1 | 11 | 21 | 94 | 55 | 26 |
| 2 | 16 | 18 | 168 | 183 | 16 | -1 | 11 | 19 | 181 | 177 | 7 | 0 | 5 | 20 | 101 | 73 | 15 | 0 | 14 | 20 | 68 | 107 | 11 | 0 | 11 | 21 | 346 | 332 | 12 |
| -2 | 17 | 18 | 88 | 82 | 14 | 1 | 11 | 19 | 138 | 153 | 15 | -3 | 6 | 20 | 229 | 207 | 13 | -2 | 15 | 20 | 183 | 201 | 14 | -2 | 12 | 21 | 96 | 98 | 10 |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| -1 | 17 | 18 | 135 | 128 | 11 | 0 | 8 | 19 | 218 | 211 | 14 | 4 | 1 | 20 | 62 | 70 | 41 | 1 | 5 | 20 | 27 | 29 | 26 |
| 0 | 17 | 18 | 259 | 279 | 29 | 1 | 8 | 19 | 101 | 73 | 14 | -4 | 2 | 20 | 57 | 35 | 56 | 2 | 5 | 20 | 175 | 201 | 16 |
| -1 | 17 | 18 | 121 | 127 | 17 | 2 | 8 | 19 | 73 | 89 | 22 | -3 | 2 | 20 | 185 | 181 | 24 | 3 | 6 | 20 | 94 | 119 | 14 |
| 1 | 17 | 18 | 109 | 82 | 27 | 3 | 8 | 19 | 51 | 46 | 34 | -2 | 2 | 20 | 144 | 148 | 9 | -2 | 6 | 20 | 179 | 177 | 12 |
| -2 | 18 | 18 | 67 | 36 | 21 | -3 | 9 | 19 | 96 | 89 | 13 | -1 | 2 | 20 | 132 | 114 | 16 | -1 | 6 | 20 | 0 | 45 | 1 |
| -1 | 18 | 18 | 104 | 86 | 13 | -1 | 9 | 19 | 97 | 63 | 17 | 0 | 2 | 20 | 503 | 539 | 32 | 0 | 6 | 20 | 266 | 252 | 9 |
| 0 | 18 | 18 | 43 | 37 | 43 | 0 | 9 | 19 | 137 | 118 | 10 | 1 | 2 | 20 | 132 | 113 | 10 | 1 | 6 | 20 | 61 | 71 | 60 |
| 1 | 18 | 18 | 95 | 86 | 31 | 1 | 9 | 19 | 0 | 24 | 1 | 2 | 2 | 20 | 150 | 148 | 7 | 2 | 6 | 20 | 246 | 252 | 13 |
| -1 | 18 | 18 | 58 | 36 | 57 | 2 | 9 | 19 | 130 | 118 | 10 | 3 | 2 | 20 | 185 | 181 | 9 | -3 | 7 | 20 | 44 | 45 | 43 |
| 1 | 18 | 18 | 44 | 60 | 43 | -2 | 1 | 19 | 80 | 63 | 20 | -4 | 3 | 20 | 0 | 34 | 1 | -2 | 7 | 20 | 136 | 178 | 12 |
| -1 | 19 | 18 | 23 | 38 | 20 | -1 | 1 | 19 | 83 | 90 | 16 | -1 | 3 | 20 | 96 | 91 | 25 | -1 | 7 | 20 | 79 | 63 | 29 |
| 0 | 19 | 18 | 175 | 156 | 38 | 0 | 1 | 19 | 64 | 68 | 38 | 1 | 3 | 20 | 222 | 224 | 12 | 0 | 7 | 20 | 37 | 53 | 37 |
| -1 | 7 | 21 | 106 | 97 | 33 | 2 | 1 | 22 | 85 | 77 | 33 | 2 | 3 | 20 | 153 | 163 | 14 | 1 | 7 | 20 | 161 | 147 | 11 |
| 0 | 7 | 21 | 162 | 157 | 34 | -1 | 13 | 22 | 35 | 76 | 34 | -2 | 13 | 20 | 86 | 73 | 36 | 2 | 7 | 20 | 84 | 98 | 21 |
| 2 | 7 | 21 | 187 | 212 | 10 | -3 | 13 | 22 | 149 | 134 | 10 | -1 | 13 | 20 | 77 | 78 | 17 | -3 | 8 | 20 | 233 | 221 | 9 |
| 3 | 7 | 21 | 0 | 41 | 17 | -2 | 14 | 22 | 18 | 49 | 18 | 0 | 13 | 20 | 111 | 124 | 13 | -2 | 8 | 20 | 254 | 229 | 15 |
| -3 | 8 | 21 | 95 | 117 | 16 | -1 | 14 | 22 | 49 | 3 | 49 | 1 | 13 | 20 | 333 | 317 | 15 | -1 | 8 | 20 | 232 | 221 | 12 |
| -1 | 8 | 21 | 0 | 27 | 25 | 0 | 14 | 22 | 70 | 48 | 20 | -3 | 14 | 20 | 133 | 123 | 12 | 0 | 8 | 20 | 117 | 93 | 19 |
| 2 | 8 | 21 | 64 | 28 | 16 | -3 | 15 | 22 | 136 | 134 | 9 | -1 | 14 | 20 | 105 | 78 | 20 | 1 | 8 | 20 | 118 | 146 | 12 |
| -1 | 0 | 21 | 100 | 96 | 25 | -2 | 15 | 22 | 78 | 76 | 21 | 0 | 14 | 20 | 307 | 318 | 16 | 2 | 8 | 20 | 95 | 84 | 16 |
| 0 | 0 | 21 | 28 | 96 | 16 | 0 | 15 | 22 | 73 | 77 | 33 | -2 | 15 | 20 | 86 | 19 | 22 | -3 | 9 | 20 | 106 | 77 | 24 |
| -1 | 0 | 21 | 27 | 27 | 11 | -2 | 16 | 22 | 83 | 96 | 25 | 0 | 15 | 20 | 114 | 129 | 16 | -2 | 9 | 20 | 37 | 12 | 37 |
| 2 | 0 | 21 | 117 | 117 | 17 | -1 | 16 | 22 | 88 | 112 | 21 | 1 | 15 | 20 | 0 | 19 | 17 | 0 | 9 | 20 | 98 | 101 | 55 |
| 3 | 0 | 21 | 159 | 159 | 13 | -2 | 16 | 22 | 89 | 85 | 21 | -2 | 16 | 20 | 305 | 318 | 49 | 1 | 9 | 20 | 74 | 12 | 49 |
| -3 | 9 | 21 | 241 | 213 | 10 | 0 | 16 | 22 | 124 | 99 | 11 | 0 | 16 | 20 | 34 | 29 | 20 | 2 | 9 | 20 | 82 | 77 | 20 |
| -2 | 9 | 21 | 174 | 127 | 9 | -2 | 17 | 22 | 162 | 174 | 13 | 2 | 16 | 20 | 115 | 110 | 22 | -3 | 0 | 20 | 81 | 84 | 34 |
| -1 | 9 | 21 | 155 | 152 | 11 | -1 | 17 | 22 | 105 | 98 | 18 | -3 | 17 | 20 | 125 | 114 | 34 | -1 | 0 | 20 | 108 | 114 | 12 |
| 0 | 9 | 21 | 151 | 126 | 11 | 0 | 18 | 22 | 97 | 85 | 11 | -1 | 17 | 20 | 146 | 110 | 29 | 0 | 0 | 20 | 29 | 17 | 29 |
| 1 | 9 | 21 | 195 | 212 | 13 | -2 | 18 | 22 | 92 | 92 | 13 | 2 | 17 | 20 | 59 | 29 | 59 | 1 | 0 | 20 | 206 | 176 | 12 |
| 2 | 9 | 21 | 133 | 159 | 11 | -1 | 19 | 22 | 100 | 96 | 15 | -3 | 18 | 20 | 100 | 109 | 23 | 2 | 0 | 20 | 108 | 83 | 1 |
| -3 | 10 | 21 | 92 | 81 | 14 | 0 | 0 | 22 | 61 | 37 | 15 | -2 | 18 | 20 | 118 | 143 | 11 | 3 | 0 | 20 | 202 | 176 | 18 |
| -2 | 10 | 21 | 110 | 77 | 9 | -2 | 0 | 22 | 59 | 59 | 49 | -1 | 19 | 20 | 35 | 33 | 35 | -3 | 1 | 20 | 114 | 17 | 15 |
| 0 | 10 | 21 | 210 | 190 | 46 | -1 | 0 | 22 | 114 | 102 | 15 | 2 | 0 | 20 | 177 | 143 | 1 | -2 | 1 | 20 | 78 | 78 | 11 |
| 2 | 10 | 21 | 46 | 60 | 12 | 0 | 0 | 22 | 75 | 70 | 30 | -1 | 0 | 20 | 35 | 54 | 59 | -1 | 1 | 20 | 137 | 139 | 11 |
| 3 | 10 | 21 | 224 | 190 | 55 | -2 | 1 | 22 | 85 | 60 | 21 | 0 | 0 | 20 | 0 | 63 | 1 | 0 | 1 | 20 | 345 | 336 | 26 |
| -3 | 11 | 21 | 55 | 77 | 49 | -1 | 1 | 22 | 68 | 70 | 20 | 1 | 0 | 20 | 60 | 54 | 23 | 1 | 1 | 20 | 126 | 122 | 16 |
| -2 | 11 | 21 | 49 | 81 | 43 | 0 | 1 | 22 | 86 | 102 | 13 | 2 | 0 | 20 | 0 | 70 | 17 | 2 | 1 | 20 | 362 | 336 | 51 |
| -1 | 11 | 21 | 44 | 18 | 19 | 2 | 1 | 22 | 0 | 60 | 1 | 3 | 0 | 20 | 24 | 9 | 43 | -3 | 2 | 20 | 151 | 139 | 12 |
| 0 | 11 | 21 | 91 | 100 | 43 | -3 | 1 | 22 | 98 | 86 | 15 | -4 | 1 | 20 | 84 | 13 | 77 | -2 | 2 | 20 | 283 | 282 | 11 |
| 3 | 11 | 21 | 62 | 47 | 30 | -2 | 1 | 22 | 50 | 41 | 30 | -2 | 1 | 20 | 175 | 163 | 9 | -1 | 2 | 20 | 63 | 78 | 25 |
| 0 | 11 | 21 | 424 | 384 | 21 | 0 | 1 | 22 | 297 | 271 | 20 | -1 | 1 | 20 | 73 | 22 | 43 | 0 | 2 | 20 | 95 | 107 | 40 |
| 1 | 11 | 21 | 0 | 47 | 1 | 1 | 1 | 22 | 31 | 38 | 13 | 0 | 1 | 20 | 78 | 72 | 77 | 1 | 2 | 20 | 304 | 282 | 80 |
| 2 | 11 | 21 | 99 | 100 | 15 | 2 | 1 | 22 | 288 | 271 | 15 | 1 | 1 | 20 | 99 | 101 | 43 | 2 | 2 | 20 | 223 | 229 | 15 |
| 3 | 11 | 21 | 41 | 19 | 41 | -3 | 1 | 22 | 55 | 40 | 41 | 2 | 1 | 20 | 114 | 112 | 12 | -3 | 3 | 20 | 283 | 282 | 21 |
| 0 | 11 | 21 | 43 | 26 | 42 | -1 | 1 | 22 | 67 | 86 | 42 | -4 | 1 | 20 | 103 | 92 | 24 | -2 | 3 | 20 | 119 | 107 | 22 |
| 1 | 11 | 21 | 43 | 51 | 43 | 0 | 1 | 22 | 108 | 109 | 43 | -2 | 1 | 20 | 66 | 102 | 54 | -1 | 3 | 20 | 131 | 143 | 20 |
| 2 | 12 | 21 | 69 | 67 | 35 | -3 | 1 | 22 | 51 | 41 | 35 | -1 | 1 | 20 | 117 | 93 | 12 | 0 | 3 | 20 | 74 | 78 | 1 |
| 0 | 12 | 21 | 124 | 120 | 17 | 1 | 1 | 22 | 22 | 49 | 17 | 0 | 1 | 20 | 119 | 112 | 11 | 1 | 3 | 20 | 128 | 142 | 29 |
| 1 | 12 | 21 | 96 | 67 | 27 | 2 | 1 | 22 | 230 | 213 | 8 | 1 | 1 | 20 | 100 | 101 | 14 | 2 | 3 | 20 | 105 | 122 | 14 |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 2 | 12 | 21 | 43 | 50 | 43 | 1 | 6 | 22 | 80 | 49 | 33 | 4 | 1 | 23 | 124 | 71 | 28 | 2 | 10 | 24 | 197 | 168 | 12 |
| 3 | 12 | 21 | 26 | 26 | 25 | 2 | 6 | 22 | 0 | 41 | 1 | -3 | 2 | 23 | 60 | 51 | 30 | 3 | 10 | 24 | 205 | 179 | 18 |
| -3 | 13 | 21 | 45 | 60 | 45 | 3 | 6 | 22 | 112 | 109 | 11 | -2 | 2 | 23 | 232 | 221 | 15 | -1 | 10 | 24 | 192 | 167 | 12 |
| -2 | 13 | 21 | 123 | 116 | 20 | -2 | 7 | 22 | 0 | 20 | 1 | -1 | 2 | 23 | 225 | 229 | 19 | 0 | 10 | 24 | 100 | 122 | 45 |
| -1 | 13 | 21 | 178 | 164 | 10 | -1 | 7 | 22 | 119 | 135 | 14 | 0 | 2 | 23 | 110 | 94 | 10 | 1 | 10 | 24 | 102 | 103 | 22 |
| 0 | 13 | 21 | 268 | 241 | 13 | 0 | 7 | 22 | 275 | 265 | 9 | 1 | 2 | 23 | 240 | 229 | 9 | 2 | 10 | 24 | 13 | 7 | 12 |
| 1 | 13 | 21 | 178 | 164 | 17 | 1 | 7 | 22 | 225 | 236 | 8 | 2 | 2 | 23 | 213 | 221 | 9 | -3 | 11 | 24 | 112 | 111 | 13 |
| 2 | 13 | 21 | 108 | 116 | 15 | 2 | 7 | 22 | 263 | 266 | 10 | -3 | 3 | 23 | 7 | 52 | 7 | -2 | 11 | 24 | 112 | 117 | 14 |
| 3 | 13 | 21 | 73 | 61 | 21 | -3 | 8 | 22 | 131 | 135 | 13 | -2 | 3 | 23 | 96 | 95 | 16 | -1 | 11 | 24 | 212 | 204 | 15 |
| -3 | 14 | 21 | 90 | 78 | 15 | -2 | 8 | 22 | 21 | 20 | 20 | -1 | 3 | 23 | 59 | 76 | 34 | 0 | 11 | 24 | 125 | 118 | 25 |
| -2 | 14 | 21 | 78 | 75 | 20 | -1 | 8 | 22 | 99 | 103 | 15 | 0 | 3 | 23 | 61 | 66 | 29 | 1 | 11 | 24 | 80 | 111 | 33 |
| 0 | 14 | 21 | 41 | 87 | 40 | 0 | 8 | 22 | 47 | 40 | 46 | 1 | 3 | 23 | 294 | 260 | 13 | 2 | 11 | 24 | 67 | 7 | 23 |
| 1 | 14 | 21 | 65 | 75 | 29 | 1 | 8 | 22 | 171 | 139 | 9 | 2 | 3 | 23 | 92 | 65 | 17 | -2 | 12 | 24 | 63 | 58 | 26 |
| 2 | 14 | 21 | 98 | 78 | 21 | 2 | 8 | 22 | 163 | 159 | 20 | -3 | 4 | 23 | 91 | 77 | 13 | -1 | 12 | 24 | 126 | 81 | 23 |
| -3 | 15 | 21 | 93 | 67 | 15 | 3 | 8 | 22 | 150 | 138 | 13 | -2 | 4 | 23 | 108 | 94 | 13 | 0 | 12 | 24 | 54 | 74 | 53 |
| -1 | 15 | 21 | 71 | 71 | 22 | -3 | 9 | 22 | 68 | 40 | 28 | -1 | 4 | 23 | 52 | 16 | 12 | 1 | 12 | 24 | 109 | 80 | 15 |
| 0 | 15 | 21 | 106 | 118 | 20 | -2 | 9 | 22 | 77 | 104 | 16 | 0 | 4 | 23 | 173 | 156 | 45 | 2 | 12 | 24 | 60 | 58 | 59 |
| 1 | 15 | 21 | 73 | 71 | 40 | -1 | 9 | 22 | 110 | 104 | 23 | 1 | 4 | 23 | 99 | 83 | 10 | -2 | 13 | 24 | 124 | 130 | 12 |
| 2 | 15 | 21 | 89 | 67 | 88 | 0 | 9 | 22 | 200 | 176 | 10 | 2 | 4 | 23 | 122 | 124 | 34 | -1 | 13 | 24 | 275 | 287 | 9 |
| -2 | 16 | 21 | 76 | 71 | 37 | 1 | 9 | 22 | 122 | 103 | 17 | -3 | 5 | 23 | 104 | 83 | 9 | 0 | 13 | 24 | 70 | 57 | 46 |
| -1 | 16 | 21 | 65 | 84 | 24 | 2 | 9 | 22 | 99 | 95 | 17 | -2 | 5 | 23 | 149 | 156 | 13 | 1 | 13 | 24 | 266 | 287 | 34 |
| 0 | 16 | 21 | 22 | 46 | 21 | -2 | 10 | 22 | 112 | 102 | 13 | -1 | 5 | 23 | 0 | 16 | 12 | 2 | 13 | 24 | 141 | 130 | 15 |
| 1 | 16 | 21 | 94 | 84 | 19 | -1 | 10 | 22 | 130 | 176 | 15 | 0 | 5 | 23 | 61 | 66 | 1 | -2 | 14 | 24 | 48 | 16 | 47 |
| 2 | 16 | 21 | 83 | 70 | 27 | 0 | 10 | 22 | 163 | 103 | 13 | 1 | 5 | 23 | 164 | 165 | 29 | -1 | 14 | 24 | 152 | 138 | 17 |
| -3 | 17 | 21 | 90 | 78 | 16 | 1 | 10 | 22 | 93 | 222 | 15 | 2 | 5 | 23 | 219 | 183 | 9 | 0 | 14 | 24 | 42 | 46 | 42 |
| -2 | 17 | 21 | 112 | 78 | 14 | 2 | 10 | 22 | 218 | 206 | 11 | -3 | 6 | 23 | 64 | 76 | 16 | 1 | 14 | 24 | 137 | 138 | 20 |
| -1 | 17 | 21 | 95 | 112 | 27 | -2 | 11 | 22 | 205 | 34 | 36 | -2 | 6 | 23 | 205 | 182 | 20 | 2 | 14 | 24 | 78 | 16 | 30 |
| 0 | 17 | 21 | 76 | 38 | 18 | -1 | 11 | 22 | 58 | 25 | 62 | -1 | 6 | 23 | 156 | 164 | 9 | -2 | 15 | 24 | 105 | 91 | 18 |
| 1 | 17 | 21 | 129 | 112 | 22 | 0 | 11 | 22 | 63 | 35 | 56 | 0 | 6 | 23 | 60 | 66 | 12 | -1 | 15 | 24 | 167 | 203 | 11 |
| 2 | 17 | 21 | 113 | 78 | 19 | 1 | 11 | 22 | 57 | 206 | 12 | 1 | 6 | 23 | 82 | 69 | 24 | 0 | 15 | 24 | 218 | 194 | 14 |
| -2 | 18 | 21 | 73 | 61 | 52 | 2 | 11 | 22 | 166 | 222 | 15 | 2 | 6 | 23 | 122 | 111 | 19 | 1 | 15 | 24 | 222 | 203 | 14 |
| -1 | 18 | 21 | 53 | 20 | 45 | -2 | 12 | 22 | 168 | 172 | 15 | -3 | 7 | 23 | 134 | 123 | 12 | 2 | 15 | 24 | 131 | 91 | 16 |
| 0 | 18 | 21 | 46 | 61 | 24 | -1 | 12 | 22 | 186 | 191 | 14 | -2 | 7 | 23 | 318 | 291 | 11 | -1 | 16 | 24 | 81 | 27 | 80 |
| 1 | 18 | 21 | 25 | 17 | 18 | 0 | 12 | 22 | 181 | 228 | 10 | -1 | 7 | 23 | 133 | 123 | 17 | 0 | 16 | 24 | 61 | 75 | 44 |
| -1 | 19 | 21 | 135 | 143 | 49 | 1 | 12 | 22 | 235 | 323 | 19 | 0 | 7 | 23 | 105 | 111 | 17 | 1 | 16 | 24 | 0 | 18 | 1 |
| 0 | 19 | 21 | 50 | 17 | 28 | 2 | 12 | 22 | 367 | 228 | 11 | 1 | 7 | 23 | 48 | 70 | 47 | 2 | 16 | 24 | 74 | 75 | 34 |
| 1 | 19 | 21 | 109 | 48 | 19 | -1 | 0 | 22 | 253 | 228 | 15 | 2 | 7 | 23 | 45 | 16 | 45 | -1 | 17 | 24 | 104 | 98 | 13 |
| 0 | 20 | 21 | 390 | 413 | 40 | 0 | 0 | 22 | 170 | 190 | 12 | -3 | 8 | 23 | 118 | 122 | 12 | 0 | 17 | 24 | 36 | 57 | 35 |
| -1 | 0 | 22 | 41 | 23 | 10 | -1 | 0 | 22 | 146 | 172 | 15 | -2 | 8 | 23 | 162 | 146 | 26 | 1 | 17 | 24 | 87 | 99 | 24 |
| -2 | 0 | 22 | 230 | 213 | 23 | 2 | 0 | 22 | 38 | 64 | 37 | -1 | 8 | 23 | 63 | 48 | 14 | 2 | 17 | 24 | 54 | 56 | 53 |
| 3 | 0 | 22 | 210 | 222 | 52 | 3 | 0 | 22 | 80 | 66 | 18 | 0 | 8 | 23 | 161 | 145 | 1 | -1 | 18 | 24 | 0 | 52 | 1 |
| 4 | 0 | 22 | 113 | 78 | 45 | 4 | 0 | 22 | 81 | 94 | 20 | 1 | 8 | 23 | 120 | 122 | 14 | 0 | 18 | 24 | 122 | 111 | 15 |
| -4 | 1 | 22 | 46 | 20 | 24 | -4 | 1 | 22 | 14 | 50 | 13 | -3 | 9 | 23 | 0 | 66 | 1 | 1 | 18 | 24 | 82 | 34 | 18 |
| -3 | 1 | 22 | 25 | 61 | 18 | -3 | 1 | 22 | 127 | 95 | 14 | -2 | 9 | 23 | 78 | 53 | 28 | 2 | 0 | 25 | 200 | 195 | 17 |
| -1 | 1 | 22 | 132 | 125 | 31 | -2 | 1 | 22 | 56 | 66 | 36 | -1 | 9 | 23 | 63 | 22 | 24 | 3 | 1 | 25 | 105 | 95 | 14 |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 0 | 1 | 1 | 22 | 273 | 267 | 13 | -3 | 8 | 22 | 62 | 73 | 21 | -1 | 8 | 23 | 51 | 37 | 51 | -1 | 4 | 24 | 0 | 29 | 1 |
| -1 | 1 | 1 | 22 | 111 | 126 | 20 | -2 | 8 | 22 | 126 | 163 | 12 | 0 | 8 | 23 | 153 | 138 | 12 | 0 | 4 | 24 | 283 | 280 | 8 |
| -2 | 1 | 1 | 22 | 135 | 128 | 9 | -1 | 8 | 22 | 227 | 225 | 9 | 1 | 8 | 23 | 90 | 37 | 19 | -1 | 4 | 24 | 66 | 28 | 25 |
| 2 | 1 | 1 | 22 | 141 | 162 | 11 | 0 | 8 | 25 | 88 | 80 | 25 | 2 | 8 | 23 | 45 | 22 | 44 | 2 | 4 | 24 | 136 | 124 | 10 |
| 3 | 1 | 1 | 22 | 179 | 164 | 18 | 1 | 8 | 25 | 86 | 64 | 32 | 2 | 8 | 26 | 103 | 99 | 20 | 2 | 9 | 24 | 135 | 153 | 19 |
| -3 | 1 | 2 | 25 | 100 | 95 | 16 | 2 | 8 | 25 | 150 | 162 | 18 | -2 | 8 | 26 | 79 | 78 | 20 | -2 | 9 | 24 | 51 | 59 | 51 |
| -2 | 2 | 2 | 25 | 0 | 9 | 1 | 3 | 8 | 25 | 30 | 21 | 29 | -1 | 11 | 26 | 158 | 164 | 10 | -1 | 10 | 24 | 167 | 139 | 13 |
| -1 | 2 | 2 | 25 | 60 | 14 | 50 | -3 | 9 | 25 | 31 | 46 | 31 | 0 | 12 | 26 | 124 | 120 | 19 | 0 | 10 | 24 | 54 | 60 | 53 |
| 0 | 2 | 2 | 25 | 227 | 206 | 13 | -2 | 9 | 25 | 148 | 190 | 22 | 1 | 12 | 26 | 166 | 164 | 14 | 1 | 10 | 24 | 128 | 140 | 18 |
| 1 | 2 | 2 | 25 | 61 | 36 | 21 | -1 | 9 | 25 | 59 | 45 | 58 | 2 | 12 | 26 | 107 | 78 | 23 | 2 | 10 | 24 | 86 | 59 | 23 |
| 2 | 2 | 2 | 25 | 224 | 206 | 14 | 0 | 9 | 25 | 61 | 49 | 24 | -2 | 12 | 26 | 110 | 97 | 14 | -2 | 10 | 24 | 49 | 69 | 49 |
| 3 | 2 | 2 | 25 | 45 | 14 | 45 | 1 | 9 | 25 | 0 | 30 | 1 | -1 | 13 | 26 | 0 | 35 | 1 | -1 | 11 | 24 | 106 | 106 | 14 |
| -3 | 2 | 3 | 25 | 47 | 10 | 47 | 2 | 9 | 25 | 30 | 49 | 29 | 0 | 13 | 26 | 101 | 111 | 22 | 0 | 11 | 24 | 52 | 92 | 52 |
| -2 | 3 | 3 | 25 | 45 | 39 | 44 | 3 | 9 | 25 | 167 | 22 | 1 | 1 | 13 | 26 | 37 | 35 | 37 | 1 | 11 | 24 | 110 | 105 | 26 |
| -1 | 3 | 3 | 25 | 101 | 65 | 15 | -3 | 9 | 26 | 101 | 153 | 14 | 2 | 13 | 26 | 115 | 97 | 18 | 2 | 11 | 24 | 84 | 68 | 26 |
| 0 | 3 | 3 | 25 | 91 | 91 | 31 | -2 | 10 | 26 | 146 | 36 | 24 | -2 | 13 | 26 | 28 | 34 | 27 | -2 | 11 | 24 | 86 | 125 | 36 |
| 1 | 3 | 3 | 25 | 70 | 5 | 18 | -1 | 0 | 26 | 78 | 116 | 15 | -1 | 14 | 26 | 43 | 39 | 43 | -1 | 12 | 24 | 94 | 111 | 16 |
| 2 | 3 | 3 | 25 | 110 | 92 | 21 | 0 | 0 | 26 | 56 | 35 | 67 | 0 | 14 | 26 | 92 | 47 | 25 | 0 | 12 | 24 | 59 | 6 | 59 |
| 3 | 3 | 3 | 25 | 51 | 65 | 36 | 1 | 0 | 26 | 76 | 48 | 29 | 1 | 14 | 26 | 30 | 39 | 29 | -2 | 12 | 24 | 108 | 110 | 19 |
| -3 | 3 | 3 | 25 | 0 | 38 | 1 | 2 | 0 | 26 | 79 | 80 | 20 | -2 | 14 | 26 | 0 | 35 | 1 | -1 | 13 | 24 | 119 | 125 | 17 |
| -2 | 4 | 4 | 25 | 84 | 90 | 33 | 3 | 1 | 26 | 324 | 319 | 35 | -1 | 15 | 26 | 74 | 57 | 19 | 0 | 15 | 27 | 0 | 53 | 1 |
| -1 | 4 | 4 | 25 | 57 | 44 | 31 | -3 | 1 | 26 | 82 | 43 | 10 | 0 | 15 | 27 | 132 | 124 | 17 | 1 | 15 | 27 | 197 | 213 | 15 |
| 0 | 4 | 4 | 25 | 185 | 172 | 15 | -2 | 1 | 26 | 69 | 81 | 40 | 1 | 15 | 27 | 69 | 57 | 38 | -1 | 16 | 27 | 54 | 36 | 53 |
| 1 | 4 | 4 | 25 | 272 | 278 | 9 | 0 | 2 | 26 | 0 | 49 | 1 | -2 | 15 | 27 | 0 | 51 | 1 | -2 | 16 | 27 | 78 | 53 | 77 |
| 2 | 4 | 4 | 25 | 175 | 172 | 12 | 1 | 2 | 26 | 46 | 49 | 46 | -1 | 16 | 27 | 58 | 66 | 58 | -3 | 16 | 27 | 56 | 65 | 31 |
| 3 | 4 | 4 | 25 | 54 | 45 | 27 | 2 | 2 | 26 | 119 | 132 | 13 | 0 | 16 | 27 | 53 | 51 | 52 | 0 | 17 | 27 | 60 | 31 | 60 |
| -3 | 4 | 4 | 25 | 85 | 90 | 15 | 3 | 2 | 26 | 141 | 132 | 12 | 1 | 17 | 27 | 17 | 67 | 1 | -3 | 0 | 28 | 91 | 76 | 15 |
| -2 | 5 | 5 | 25 | 0 | 11 | 1 | -3 | 2 | 26 | 159 | 105 | 15 | -1 | 0 | 27 | 104 | 67 | 24 | -2 | 0 | 28 | 52 | 17 | 52 |
| -1 | 5 | 5 | 25 | 118 | 114 | 12 | -2 | 3 | 26 | 146 | 129 | 10 | 0 | 0 | 27 | 198 | 166 | 13 | -1 | 0 | 28 | 78 | 76 | 28 |
| 0 | 5 | 5 | 25 | 83 | 101 | 31 | -1 | 3 | 26 | 126 | 104 | 20 | 1 | 0 | 27 | 74 | 56 | 19 | 0 | 0 | 28 | 28 | 22 | 27 |
| 1 | 5 | 5 | 25 | 171 | 175 | 9 | 0 | 3 | 26 | 141 | 132 | 13 | 2 | 0 | 27 | 124 | 125 | 12 | 1 | 0 | 28 | 110 | 119 | 20 |
| 2 | 5 | 5 | 25 | 89 | 101 | 24 | 1 | 3 | 26 | 117 | 133 | 11 | 3 | 0 | 27 | 135 | 127 | 11 | 2 | 0 | 28 | 38 | 23 | 11 |
| 3 | 5 | 5 | 25 | 135 | 114 | 13 | 2 | 3 | 26 | 81 | 51 | 20 | -3 | 0 | 27 | 124 | 129 | 20 | -3 | 0 | 28 | 376 | 331 | 18 |
| -3 | 5 | 5 | 25 | 32 | 11 | 32 | -3 | 3 | 26 | 68 | 79 | 11 | -2 | 0 | 27 | 136 | 123 | 18 | -2 | 1 | 28 | 132 | 99 | 21 |
| -2 | 6 | 6 | 25 | 101 | 68 | 10 | -2 | 4 | 26 | 120 | 91 | 18 | -1 | 1 | 27 | 142 | 129 | 18 | -1 | 1 | 28 | 49 | 36 | 49 |
| -1 | 6 | 6 | 25 | 146 | 155 | 20 | -1 | 4 | 26 | 82 | 51 | 15 | 0 | 1 | 27 | 155 | 127 | 12 | 0 | 1 | 28 | 71 | 71 | 19 |
| 0 | 6 | 6 | 25 | 104 | 89 | 16 | 0 | 4 | 26 | 125 | 91 | 21 | 1 | 1 | 27 | 141 | 125 | 13 | 1 | 1 | 28 | 102 | 106 | 13 |
| 1 | 6 | 6 | 25 | 107 | 83 | 14 | 1 | 4 | 26 | 80 | 79 | 16 | 2 | 1 | 27 | 103 | 106 | 15 | 2 | 1 | 28 | 97 | 67 | 24 |
| 2 | 6 | 6 | 25 | 122 | 88 | 14 | 2 | 4 | 26 | 0 | 51 | 1 | 3 | 1 | 27 | 106 | 87 | 36 | -3 | 1 | 28 | 175 | 128 | 15 |
| 3 | 6 | 6 | 25 | 128 | 154 | 17 | -3 | 4 | 26 | 146 | 112 | 20 | -3 | 1 | 27 | 79 | 66 | 13 | -2 | 1 | 28 | 50 | 17 | 50 |
| -3 | 6 | 6 | 25 | 77 | 69 | 11 | -2 | 5 | 26 | 102 | 64 | 13 | -2 | 2 | 27 | 126 | 122 | 15 | -1 | 2 | 28 | 130 | 128 | 20 |
| -2 | 7 | 7 | 25 | 151 | 150 | 12 | -1 | 5 | 26 | 181 | 168 | 15 | -1 | 2 | 27 | 92 | 66 | 36 | 0 | 2 | 28 | 69 | 67 | 21 |
| -1 | 7 | 7 | 25 | 136 | 111 | 24 | 0 | 5 | 26 | 78 | 62 | 26 | 0 | 2 | 27 | 107 | 87 | 14 | 1 | 2 | 28 | 132 | 106 | 12 |
| 0 | 7 | 7 | 25 | 89 | 41 | 46 | 2 | 5 | 26 | 161 | 168 | 16 | 1 | 2 | 27 | 112 | 107 | 14 | 2 | 2 | 28 | 124 | 140 | 10 |
| 0 | 7 | 7 | 25 | 46 | 66 | 46 | 3 | 6 | 26 | 61 | 64 | 22 | -3 | 2 | 27 | 168 | 152 | 15 | 3 | 2 | 29 | | | |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 1 | 7 | 25 | 96 | 42 | 35 | 3 | 4 | 26 | 107 | 113 | 13 | -2 | 3 | 27 | 135 | 139 | 11 | 3 | 1 | 29 | 87 | 54 | 20 |
| 2 | 7 | 25 | 127 | 111 | 14 | -3 | 5 | 26 | 84 | 69 | 18 | -1 | 3 | 27 | 229 | 239 | 14 | -3 | 2 | 29 | 109 | 104 | 12 |
| 3 | 7 | 25 | 130 | 150 | 10 | -2 | 5 | 26 | 166 | 151 | 10 | 0 | 3 | 27 | 98 | 100 | 27 | -2 | 2 | 29 | 126 | 88 | 14 |
| -3 | 8 | 25 | 49 | 60 | 49 | -1 | 5 | 26 | 109 | 42 | 23 | 1 | 3 | 27 | 226 | 240 | 30 | -1 | 2 | 29 | 301 | 291 | 33 |
| -2 | 8 | 25 | 104 | 91 | 15 | 0 | 5 | 26 | 13 | 5 | 13 | 2 | 3 | 27 | 116 | 140 | 13 | 0 | 2 | 29 | 120 | 99 | 17 |
| -1 | 8 | 25 | 191 | 203 | 11 | 1 | 5 | 26 | 86 | 42 | 32 | 3 | 3 | 27 | 143 | 151 | 11 | 1 | 2 | 29 | 252 | 291 | 26 |
| 0 | 8 | 25 | 26 | 43 | 26 | 2 | 5 | 26 | 151 | 150 | 17 | -3 | 4 | 27 | 66 | 56 | 25 | 2 | 2 | 29 | 90 | 88 | 13 |
| 1 | 8 | 25 | 200 | 202 | 15 | 3 | 5 | 26 | 69 | 69 | 20 | -2 | 4 | 27 | 110 | 112 | 12 | 3 | 2 | 29 | 126 | 104 | 14 |
| 2 | 8 | 25 | 101 | 91 | 16 | -3 | 6 | 26 | 70 | 26 | 22 | -1 | 4 | 27 | 49 | 43 | 18 | -3 | 3 | 29 | 114 | 124 | 12 |
| 3 | 8 | 25 | 80 | 59 | 18 | -2 | 6 | 26 | 0 | 31 | 1 | 0 | 4 | 27 | 310 | 274 | 40 | -2 | 3 | 29 | 70 | 42 | 27 |
| -3 | 9 | 25 | 0 | 35 | 2 | -1 | 6 | 26 | 195 | 185 | 15 | 1 | 4 | 27 | 0 | 43 | 15 | -1 | 3 | 29 | 62 | 38 | 61 |
| -2 | 9 | 25 | 20 | 45 | 20 | 0 | 6 | 26 | 127 | 131 | 15 | 2 | 4 | 27 | 133 | 113 | 22 | 0 | 3 | 29 | 297 | 282 | 11 |
| -1 | 9 | 25 | 200 | 188 | 10 | 1 | 6 | 26 | 183 | 184 | 14 | 3 | 4 | 27 | 63 | 56 | 14 | 1 | 3 | 29 | 55 | 39 | 55 |
| 0 | 9 | 25 | 153 | 164 | 26 | 2 | 6 | 26 | 6 | 31 | 5 | -3 | 5 | 27 | 0 | 41 | 43 | 2 | 3 | 29 | 0 | 41 | 1 |
| 1 | 9 | 25 | 208 | 188 | 21 | 3 | 6 | 26 | 0 | 26 | 1 | -2 | 5 | 27 | 102 | 67 | 10 | 3 | 3 | 29 | 113 | 124 | 15 |
| 2 | 9 | 25 | 65 | 44 | 29 | -3 | 7 | 26 | 87 | 75 | 38 | -1 | 5 | 27 | 191 | 175 | 18 | -3 | 4 | 29 | 50 | 73 | 50 |
| 3 | 9 | 25 | 72 | 34 | 71 | -2 | 7 | 26 | 77 | 25 | 19 | 0 | 5 | 27 | 69 | 18 | 16 | -2 | 4 | 29 | 53 | 60 | 53 |
| -3 | 10 | 25 | 68 | 73 | 34 | -1 | 7 | 26 | 39 | 59 | 12 | 1 | 5 | 27 | 192 | 174 | 29 | -1 | 4 | 29 | 94 | 90 | 25 |
| -2 | 10 | 25 | 24 | 37 | 23 | 0 | 7 | 26 | 86 | 165 | 50 | 2 | 5 | 27 | 64 | 67 | 32 | 0 | 4 | 29 | 84 | 62 | 22 |
| -1 | 10 | 25 | 132 | 115 | 12 | 1 | 7 | 26 | 51 | 25 | 16 | 3 | 5 | 27 | 16 | 41 | 62 | 1 | 4 | 29 | 113 | 90 | 15 |
| 0 | 10 | 25 | 101 | 79 | 27 | 2 | 7 | 26 | 167 | 165 | 19 | -3 | 6 | 27 | 51 | 36 | 16 | 2 | 4 | 29 | 70 | 59 | 18 |
| 1 | 10 | 25 | 114 | 116 | 54 | 3 | 7 | 26 | 86 | 60 | 1 | -2 | 6 | 27 | 176 | 182 | 50 | -3 | 5 | 29 | 82 | 73 | 24 |
| 2 | 10 | 25 | 81 | 37 | 20 | -3 | 8 | 26 | 0 | 25 | 17 | -1 | 6 | 27 | 130 | 91 | 12 | -2 | 5 | 29 | 105 | 108 | 17 |
| 3 | 10 | 25 | 75 | 73 | 10 | -2 | 8 | 26 | 87 | 75 | 22 | 0 | 6 | 27 | 174 | 174 | 24 | -1 | 5 | 29 | 173 | 154 | 15 |
| -2 | 11 | 25 | 176 | 147 | 10 | -1 | 8 | 26 | 77 | 25 | 17 | 1 | 6 | 27 | 387 | 341 | 13 | 0 | 5 | 29 | 238 | 233 | 17 |
| -1 | 11 | 25 | 334 | 282 | 16 | 0 | 8 | 26 | 46 | 39 | 22 | 2 | 6 | 27 | 99 | 90 | 38 | 1 | 5 | 29 | 46 | 23 | 25 |
| 0 | 11 | 25 | 92 | 85 | 10 | 1 | 8 | 26 | 72 | 52 | 46 | 3 | 6 | 27 | 175 | 182 | 13 | 2 | 5 | 29 | 215 | 234 | 46 |
| 1 | 11 | 25 | 289 | 282 | 30 | 2 | 8 | 26 | 0 | 40 | 1 | -3 | 7 | 27 | 53 | 36 | 1 | -3 | 6 | 29 | 128 | 154 | 14 |
| 2 | 11 | 25 | 137 | 147 | 19 | 3 | 8 | 26 | 40 | 25 | 39 | -2 | 7 | 27 | 51 | 32 | 17 | -2 | 6 | 29 | 81 | 108 | 18 |
| -2 | 12 | 25 | 129 | 139 | 16 | -3 | 9 | 26 | 97 | 74 | 15 | -1 | 7 | 27 | 68 | 21 | 28 | -1 | 6 | 29 | 0 | 24 | 22 |
| -1 | 12 | 25 | 119 | 110 | 12 | -2 | 9 | 26 | 131 | 76 | 15 | 0 | 7 | 27 | 183 | 175 | 1 | 0 | 6 | 29 | 0 | 44 | 1 |
| 0 | 12 | 25 | 132 | 113 | 20 | -1 | 9 | 26 | 61 | 80 | 30 | 1 | 7 | 27 | 265 | 251 | 26 | 1 | 6 | 29 | 129 | 150 | 15 |
| 1 | 12 | 25 | 109 | 111 | 49 | 0 | 9 | 26 | 153 | 127 | 11 | 2 | 7 | 27 | 160 | 174 | 13 | 2 | 6 | 29 | 0 | 43 | 1 |
| -2 | 13 | 25 | 156 | 139 | 14 | 1 | 9 | 26 | 112 | 70 | 18 | -2 | 8 | 27 | 21 | 31 | 18 | -2 | 7 | 29 | 61 | 24 | 56 |
| -1 | 13 | 25 | 177 | 187 | 11 | 2 | 9 | 26 | 122 | 127 | 27 | -1 | 8 | 27 | 31 | 32 | 53 | -1 | 7 | 29 | 69 | 52 | 29 |
| 0 | 13 | 25 | 78 | 77 | 20 | 3 | 9 | 26 | 116 | 80 | 19 | 0 | 8 | 27 | 53 | 49 | 55 | 0 | 7 | 29 | 66 | 50 | 32 |
| 1 | 13 | 25 | 222 | 210 | 28 | -3 | 10 | 26 | 110 | 76 | 13 | 1 | 8 | 27 | 200 | 206 | 22 | 1 | 7 | 29 | 189 | 159 | 12 |
| -2 | 14 | 25 | 64 | 77 | 64 | -2 | 10 | 26 | 114 | 34 | 42 | 2 | 8 | 27 | 217 | 209 | 10 | 2 | 7 | 29 | 0 | 50 | 1 |
| -1 | 14 | 25 | 198 | 188 | 13 | -1 | 10 | 26 | 127 | 101 | 23 | -2 | 9 | 27 | 74 | 58 | 10 | -1 | 8 | 29 | 62 | 52 | 30 |
| 0 | 14 | 25 | 43 | 45 | 18 | 0 | 10 | 26 | 99 | 71 | 21 | -1 | 9 | 27 | 202 | 209 | 29 | 0 | 8 | 29 | 53 | 59 | 53 |
| 1 | 14 | 25 | 179 | 177 | 42 | 1 | 10 | 26 | 61 | 117 | 25 | 0 | 9 | 27 | 218 | 207 | 15 | 1 | 8 | 29 | 45 | 16 | 45 |
| 0 | 14 | 25 | 244 | 266 | 14 | 2 | 10 | 26 | 153 | 72 | 23 | 1 | 9 | 27 | 57 | 50 | 48 | 2 | 8 | 29 | 87 | 59 | 33 |
| 1 | 14 | 25 | 184 | 176 | 17 | -2 | 11 | 26 | 100 | 101 | 16 | -2 | 9 | 27 | 0 | 69 | 1 | -1 | 8 | 29 | 53 | 16 | 52 |
| 2 | 14 | 25 | 0 | 44 | 1 | -1 | 11 | 26 | 107 | 99 | 19 | -1 | 9 | 27 | 139 | 153 | 11 | 0 | 8 | 29 | 54 | 60 | 53 |
| | | | | | | 0 | 11 | 26 | 84 | 176 | 13 | 2 | 9 | 27 | 114 | 126 | 14 | | | | | | |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| -2 | 15 | 25 | 39 | 22 | 39 | 0 | 11 | 26 | 63 | 119 | 62 | 0 | 9 | 27 | 194 | 140 | 15 | -2 | 9 | 29 | 68 | 24 | 25 |
| -1 | 15 | 25 | 178 | 162 | 9 | 1 | 11 | 26 | 167 | 176 | 29 | 1 | 9 | 27 | 117 | 126 | 28 | -1 | 9 | 29 | 17 | 2 | 17 |
| 0 | 9 | 29 | 95 | 67 | 19 | -1 | 8 | 30 | 104 | 96 | 26 | -1 | 9 | 31 | 96 | 99 | 15 | 0 | 9 | 29 | 111 | 115 | 19 |
| 1 | 9 | 29 | 0 | 2 | 1 | 0 | 8 | 30 | 126 | 95 | 18 | 0 | 9 | 31 | 71 | 30 | 37 | 1 | 9 | 29 | 63 | 61 | 28 |
| -2 | 10 | 29 | 0 | 24 | 45 | 1 | 8 | 30 | 75 | 96 | 35 | 1 | 9 | 31 | 126 | 98 | 16 | -2 | 9 | 29 | 0 | 17 | 1 |
| -1 | 10 | 29 | 46 | 46 | 10 | -1 | 9 | 30 | 83 | 133 | 51 | -2 | 10 | 31 | 115 | 71 | 33 | -1 | 9 | 29 | 107 | 62 | 20 |
| 0 | 10 | 29 | 161 | 167 | 22 | 0 | 9 | 30 | 0 | 0 | 1 | -1 | 10 | 31 | 63 | 62 | 28 | 0 | 9 | 29 | 60 | 72 | 36 |
| 1 | 10 | 29 | 79 | 35 | 61 | 1 | 9 | 30 | 135 | 51 | 18 | 0 | 10 | 31 | 87 | 85 | 25 | 1 | 9 | 29 | 37 | 52 | 37 |
| -1 | 10 | 29 | 163 | 167 | 1 | -1 | 10 | 30 | 206 | 129 | 16 | 1 | 10 | 31 | 84 | 62 | 20 | -2 | 9 | 29 | 61 | 73 | 61 |
| 0 | 10 | 29 | 0 | 46 | 17 | 0 | 10 | 30 | 144 | 209 | 40 | -1 | 11 | 31 | 54 | 43 | 37 | -1 | 9 | 29 | 0 | 37 | 1 |
| 1 | 10 | 29 | 96 | 55 | 32 | 1 | 10 | 30 | 83 | 129 | 61 | 0 | 11 | 31 | 78 | 62 | 1 | 0 | 9 | 29 | 100 | 86 | 17 |
| -1 | 11 | 29 | 97 | 79 | 21 | -1 | 11 | 30 | 30 | 51 | 29 | 1 | 11 | 31 | 15 | 43 | 32 | 1 | 9 | 29 | 73 | 37 | 32 |
| 0 | 11 | 29 | 143 | 97 | 17 | 0 | 11 | 30 | 142 | 20 | 11 | -1 | 11 | 31 | 0 | 13 | 14 | -2 | 9 | 29 | 81 | 62 | 21 |
| -1 | 11 | 29 | 82 | 79 | 26 | 1 | 11 | 30 | 14 | 136 | 14 | 0 | 12 | 31 | 33 | 33 | 1 | -1 | 9 | 29 | 0 | 42 | 1 |
| 0 | 11 | 29 | 0 | 0 | 46 | -1 | 12 | 30 | 129 | 24 | 17 | -1 | 12 | 31 | 14 | 14 | 32 | 0 | 9 | 29 | 78 | 62 | 33 |
| 1 | 11 | 29 | 46 | 54 | 16 | 0 | 12 | 30 | 137 | 20 | 75 | -1 | 13 | 31 | 92 | 107 | 40 | 1 | 9 | 29 | 83 | 63 | 27 |
| -2 | 12 | 29 | 17 | 42 | 15 | 0 | 13 | 30 | 76 | 33 | 50 | -1 | 13 | 31 | 41 | 17 | 18 | -2 | 9 | 29 | 0 | 6 | 1 |
| 0 | 12 | 29 | 227 | 193 | 17 | -1 | 12 | 30 | 50 | 59 | 26 | 0 | 13 | 31 | 185 | 180 | 15 | -1 | 9 | 29 | 61 | 24 | 54 |
| -1 | 12 | 29 | 49 | 49 | 18 | 0 | 12 | 30 | 65 | 7 | 39 | -1 | 13 | 31 | 139 | 166 | 44 | 0 | 9 | 29 | 89 | 39 | 25 |
| 0 | 12 | 29 | 0 | 66 | 47 | 1 | 12 | 30 | 39 | 60 | 36 | 0 | 0 | 32 | 46 | 38 | 55 | 1 | 9 | 29 | 62 | 24 | 45 |
| -1 | 13 | 29 | 47 | 42 | 1 | -1 | 13 | 30 | 75 | 54 | 45 | -1 | 0 | 32 | 128 | 126 | 19 | -2 | 9 | 29 | 75 | 63 | 74 |
| 0 | 13 | 29 | 0 | 66 | 28 | 0 | 13 | 30 | 46 | 25 | 34 | -2 | 1 | 32 | 92 | 124 | 12 | -1 | 9 | 29 | 0 | 71 | 1 |
| -1 | 14 | 29 | 81 | 92 | 21 | -1 | 14 | 30 | 34 | 55 | 40 | -1 | 1 | 32 | 105 | 106 | 21 | 0 | 9 | 29 | 106 | 63 | 21 |
| 0 | 14 | 29 | 97 | 66 | 54 | 0 | 14 | 30 | 40 | 10 | 34 | 0 | 1 | 32 | 98 | 124 | 17 | 1 | 9 | 29 | 0 | 30 | 1 |
| 1 | 14 | 29 | 55 | 92 | 21 | 1 | 14 | 30 | 72 | 88 | 1 | 1 | 1 | 32 | 125 | 126 | 24 | -2 | 9 | 29 | 96 | 80 | 20 |
| -2 | 14 | 29 | 92 | 26 | 28 | -1 | 0 | 31 | 0 | 4 | 33 | -2 | 2 | 32 | 77 | 79 | 25 | -1 | 9 | 29 | 0 | 30 | 1 |
| 0 | 14 | 29 | 0 | 30 | 12 | 0 | 0 | 31 | 69 | 87 | 33 | -1 | 2 | 32 | 63 | 50 | 39 | 0 | 9 | 29 | 89 | 93 | 19 |
| 1 | 15 | 29 | 95 | 91 | 13 | -1 | 0 | 31 | 85 | 87 | 33 | 0 | 2 | 32 | 93 | 84 | 19 | 1 | 9 | 29 | 0 | 18 | 1 |
| -1 | 0 | 30 | 12 | 14 | 16 | 0 | 0 | 31 | 33 | 10 | 40 | 1 | 2 | 32 | 69 | 70 | 36 | -2 | 9 | 29 | 109 | 93 | 21 |
| 0 | 0 | 30 | 144 | 143 | 27 | -2 | 1 | 31 | 23 | 11 | 34 | -2 | 3 | 32 | 62 | 79 | 61 | -1 | 9 | 29 | 46 | 50 | 45 |
| 1 | 0 | 30 | 104 | 93 | 16 | -1 | 1 | 31 | 128 | 146 | 25 | -1 | 3 | 32 | 181 | 163 | 11 | 0 | 9 | 29 | 0 | 6 | 1 |
| -2 | 1 | 30 | 70 | 70 | 70 | 0 | 1 | 31 | 123 | 115 | 15 | 0 | 3 | 32 | 66 | 70 | 36 | 1 | 9 | 29 | 27 | 49 | 26 |
| -1 | 1 | 30 | 71 | 120 | 32 | 1 | 1 | 31 | 159 | 177 | 28 | 1 | 3 | 32 | 34 | 39 | 34 | -1 | 9 | 29 | 107 | 115 | 16 |
| 0 | 1 | 30 | 203 | 200 | 54 | -2 | 2 | 31 | 187 | 200 | 15 | -2 | 4 | 32 | 77 | 70 | 30 | 0 | 9 | 29 | 70 | 54 | 27 |
| 1 | 1 | 30 | 54 | 39 | 38 | -1 | 2 | 31 | 173 | 177 | 21 | -1 | 4 | 32 | 121 | 163 | 11 | 1 | 9 | 29 | 126 | 115 | 17 |
| -2 | 2 | 30 | 182 | 200 | 12 | 0 | 2 | 31 | 108 | 116 | 15 | 0 | 4 | 32 | 81 | 70 | 21 | -2 | 9 | 29 | 0 | 56 | 1 |
| -1 | 2 | 30 | 126 | 120 | 53 | 1 | 2 | 31 | 72 | 95 | 24 | 1 | 4 | 32 | 225 | 263 | 11 | -1 | 9 | 29 | 77 | 84 | 24 |
| 0 | 2 | 30 | 53 | 70 | 48 | -2 | 3 | 31 | 0 | 79 | 1 | -2 | 5 | 32 | 96 | 98 | 20 | 0 | 9 | 29 | 48 | 56 | 48 |
| 1 | 2 | 30 | 49 | 33 | 36 | -1 | 3 | 31 | 25 | 15 | 24 | -1 | 5 | 32 | 219 | 263 | 14 | 1 | 9 | 29 | 80 | 26 | 38 |
| -3 | 2 | 30 | 37 | 64 | 23 | 0 | 3 | 31 | 87 | 79 | 24 | 0 | 5 | 32 | 89 | 71 | 24 | -2 | 9 | 29 | 46 | 50 | 46 |
| -2 | 2 | 30 | 143 | 136 | 12 | 1 | 3 | 31 | 56 | 94 | 55 | 1 | 5 | 32 | 42 | 55 | 41 | -1 | 9 | 29 | 0 | 7 | 1 |
| -1 | 2 | 30 | 146 | 144 | 20 | -1 | 3 | 31 | 165 | 165 | 18 | 0 | 5 | 32 | 96 | 113 | 19 | 0 | 9 | 29 | 97 | 106 | 35 |
| 0 | 2 | 30 | 106 | 136 | 20 | 0 | 3 | 31 | 71 | 87 | 32 | -1 | 5 | 32 | 138 | 131 | 14 | 1 | 9 | 29 | 55 | 1 | 55 |
| 1 | 2 | 30 | 63 | 64 | 23 | 1 | 3 | 31 | 103 | 113 | 20 | 0 | 5 | 32 | 104 | 113 | 45 | -2 | 9 | 29 | 23 | 76 | 22 |
| 2 | 2 | 30 | 52 | 33 | 51 | -2 | 3 | 31 | 88 | 86 | 31 | | | | | | | | | | | | |

TABLE 7-continued

Observed and calculated structure factors for 051810.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|
| -3 | 3 | 30 | 0 | 21 | 1 | 2 | 5 | 31 | 117 | 166 | 19 | 2 | 5 | 32 | 0 | 55 | 1 | 0 | 1 | 33 | 48 | 11 | 48 |
| -2 | 3 | 30 | 54 | 63 | 49 | -2 | 6 | 31 | 126 | 122 | 13 | -2 | 6 | 32 | 61 | 30 | 32 | -1 | 1 | 33 | 46 | 50 | 45 |
| -1 | 3 | 30 | 57 | 68 | 56 | -1 | 6 | 31 | 69 | 68 | 36 | -1 | 6 | 32 | 134 | 146 | 12 | -1 | 2 | 33 | 132 | 125 | 13 |
| 0 | 3 | 30 | 300 | 302 | 11 | 0 | 6 | 31 | 103 | 87 | 18 | 0 | 6 | 32 | 96 | 116 | 17 | 0 | 2 | 33 | 254 | 258 | 25 |
| 1 | 3 | 30 | 43 | 68 | 43 | 1 | 6 | 31 | 100 | 69 | 20 | 1 | 6 | 32 | 145 | 146 | 15 | -1 | 2 | 33 | 57 | 41 | 56 |
| 2 | 3 | 30 | 0 | 63 | 1 | -2 | 6 | 31 | 110 | 122 | 19 | -2 | 7 | 32 | 0 | 30 | 1 | 1 | 2 | 34 | 0 | 45 | 1 |
| -2 | 4 | 30 | 134 | 121 | 16 | -1 | 7 | 31 | 109 | 93 | 15 | -1 | 7 | 32 | 49 | 23 | 49 | -2 | 3 | 34 | 51 | 20 | 50 |
| -1 | 4 | 30 | 99 | 113 | 27 | 0 | 7 | 31 | 159 | 179 | 32 | 0 | 7 | 32 | 99 | 115 | 18 | -1 | 3 | 34 | 120 | 141 | 17 |
| 0 | 4 | 30 | 229 | 206 | 10 | 1 | 7 | 31 | 0 | 25 | 1 | 1 | 7 | 32 | 106 | 82 | 52 | 0 | 3 | 34 | 150 | 131 | 13 |
| 1 | 4 | 30 | 98 | 113 | 19 | -2 | 7 | 31 | 167 | 178 | 14 | -2 | 7 | 32 | 115 | 115 | 17 | 1 | 3 | 34 | 131 | 141 | 17 |
| -2 | 4 | 30 | 85 | 121 | 29 | -1 | 7 | 31 | 0 | 93 | 1 | -1 | 7 | 32 | 0 | 23 | 1 | -1 | 4 | 34 | 33 | 20 | 32 |
| 2 | 4 | 30 | 110 | 114 | 17 | 0 | 8 | 31 | 140 | 145 | 13 | 0 | 8 | 32 | 50 | 83 | 49 | 0 | 4 | 34 | 84 | 76 | 26 |
| -2 | 5 | 30 | 78 | 81 | 22 | -1 | 8 | 31 | 80 | 33 | 21 | -1 | 8 | 32 | 81 | 91 | 21 | 1 | 4 | 34 | 92 | 103 | 21 |
| -1 | 5 | 30 | 125 | 120 | 14 | 0 | 8 | 31 | 167 | 181 | 12 | 0 | 8 | 32 | 70 | 38 | 28 | -1 | 5 | 34 | 123 | 120 | 15 |
| 0 | 5 | 30 | 52 | 81 | 52 | 1 | 8 | 31 | 42 | 33 | 41 | 1 | 8 | 32 | 82 | 90 | 28 | 0 | 5 | 34 | 103 | 103 | 20 |
| 1 | 5 | 30 | 105 | 114 | 20 | 2 | 8 | 31 | 151 | 145 | 34 | 2 | 8 | 32 | 112 | 83 | 33 | 1 | 5 | 34 | 0 | 76 | 1 |
| -2 | 6 | 30 | 135 | 142 | 13 | -2 | 7 | 31 | 78 | 57 | 22 | -2 | 9 | 32 | 36 | 39 | 35 | -1 | 6 | 34 | 51 | 39 | 50 |
| -1 | 6 | 30 | 109 | 121 | 15 | -1 | 7 | 31 | 77 | 100 | 48 | -1 | 9 | 32 | 50 | 68 | 50 | 0 | 6 | 34 | 95 | 103 | 17 |
| 0 | 6 | 30 | 47 | 48 | 47 | 0 | 7 | 31 | 142 | 140 | 12 | 0 | 9 | 32 | 65 | 39 | 42 | 1 | 6 | 34 | 161 | 176 | 24 |
| 1 | 6 | 30 | 111 | 121 | 18 | 1 | 7 | 31 | 86 | 99 | 34 | 1 | 9 | 32 | 60 | 63 | 29 | -1 | 6 | 34 | 101 | 103 | 21 |
| -2 | 7 | 30 | 121 | 142 | 33 | -2 | 8 | 31 | 0 | 57 | 1 | -2 | 10 | 32 | 25 | 31 | 24 | 0 | 7 | 34 | 0 | 39 | 1 |
| -1 | 7 | 30 | 63 | 54 | 33 | -1 | 8 | 31 | 0 | 37 | 1 | -1 | 10 | 32 | 63 | 63 | 63 | -1 | 7 | 34 | 42 | 45 | 42 |
| 0 | 7 | 30 | 70 | 95 | 23 | 0 | 8 | 31 | 88 | 88 | 20 | 0 | 10 | 32 | 80 | 66 | 19 | 0 | 7 | 34 | 107 | 135 | 15 |
| 1 | 7 | 30 | 70 | 45 | 30 | 1 | 8 | 31 | 74 | 23 | 27 | 1 | 11 | 32 | 0 | 42 | 1 | 1 | 7 | 34 | 75 | 89 | 37 |
| -1 | 7 | 30 | 77 | 95 | 28 | -1 | 8 | 31 | 100 | 88 | 70 | -1 | 11 | 32 | 19 | 66 | 19 | -2 | 8 | 34 | 130 | 135 | 34 |
| -2 | 8 | 30 | 64 | 54 | 44 | -2 | 9 | 31 | 0 | 37 | 1 | -1 | 12 | 32 | 0 | 42 | 1 | -1 | 8 | 34 | 115 | 116 | 14 |
| -1 | 8 | 30 | 130 | 134 | 14 | -1 | 9 | 31 | 83 | 71 | 22 | 0 | 12 | 32 | 55 | 87 | 54 | 0 | 5 | 34 | 0 | 4 | 1 |

EXAMPLE 2

Synthesis of 051810

The preparation of 051810 having the basic structure I can be accomplished by a common general method, i.e. the condensation of a bicyclic Windaus-Grundmann type ketone II with the allylic phosphine oxide III to the corresponding 2-methylene-19-nor-vitamin D analog IV followed by deprotection at C-1 and C-3 in the latter compound IV to obtain compound I, i.e. 05180.

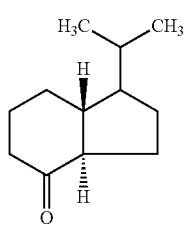

II

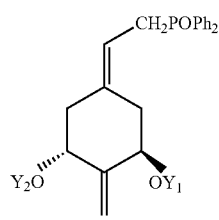

III

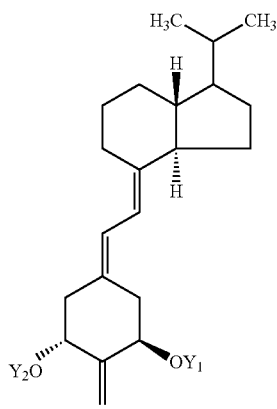

IV

In phosphine oxide III, $Y_1$ and $Y_2$ are preferably hydroxy-protecting groups such as silyl protecting groups. The t-butyldimethylsilyl (TMDMS) group is an example of a particularly useful hydroxy-protecting group. The process described above represents an application of the convergent synthesis concept, which has been applied effectively to the preparation of numerous vitamin D compounds (see Lythgoe et al., *J. Chem. Soc. Perkin Trans. I,* 590 (1978); Lythgoe, *Chem. Soc. Rev.* 9, 449 (1983); Toh et al., *J. Org. Chem.* 48, 1414 (1983); Baggiolini et al., *J. Org. Chem.* 51, 3098 (1986); Sardina et al., *J. Org. Chem.* 51, 1264 (1986); *J. Org. Chem.* 51, 1269 (1986); DeLuca et al., U.S. Pat. No. 5,086,191; DeLuca et al., U.S. Pat. No. 5,536,713; and DeLuca et al, U.S. Pat. No. 5,843,928 all of which are hereby incorporated by reference in their entirety and for all purposes as if fully set forth herein.

Phosphine oxide III is a convenient reagent that can be used to prepare a large number of 19-nor-vitamin D compounds and is prepared according to the procedures described by Sicinski et al., *J. Med. Chem.,* 41, 4662 (1998), DeLuca et al., U.S. Pat. No. 5,843,928; Perlman et al., *Tetrahedron Lett.* 32, 7663 (1991); and DeLuca et al., U.S. Pat. No. 5,086,191 which are hereby incorporated by reference in their entirety as if fully set forth herein.

The overall process of the synthesis of compound I is illustrated and described more completely in U.S. Pat. No. 5,843,928 entitled "2-Alkylidene-19-Nor-Vitamin D Compounds" and in U.S. Pat. No. 7,238,681, entitled "2-Methylene-18,19-Dinor-1α-Hydroxy-Homopregnacalciferol and Its Uses" the specifications of which are specifically incorporated herein by reference.

We claim:

1. 1α-hydroxy-2-methylene-18,19-dinor-homopregnacalciferol in crystalline form.

2. The crystalline form of 1α-hydroxy-2-methylene-18,19-dinor-homopregnacalciferol having molecular packing arrangement defined by space group P2 and unit cell dimensions a=4.8 Å, b=22.9 Å, c=36.1 Å, α=90°, β=90° and γ=90°.

3. A three dimensional structure for 1α-hydroxy-2-methylene-18,19-dinor-homopregnacalciferol as defined by the molecular packing arrangement set forth in claim 2.

4. A method of purifying 1α-hydroxy-2-methylene-18,19-dinor-homopregnacalciferol, comprising the steps of:
   (a) dissolving a product containing 1α-hydroxy-2-methylene-18,19-dinor-homopregnacalciferol to be purified in a solvent comprising ethyl acetate;
   (b) adding hexane to said solvent and dissolved product to form a mixture;
   (c) cooling said mixture containing said dissolved product below ambient temperature for a sufficient amount of time to form a precipitate of 1α-hydroxy-2-methylene-18,19-dinor-homopregnacalciferol crystals; and
   (d) separating the 1α-hydroxy-2-methylene-18,19-dinor-homopregnacalciferol crystals from the mixture.

5. The method of claim 4 wherein the step of separating comprises filtering the mixture and precipitate to obtain the crystals.

6. The method of claim 4 including a further step (d) comprising repeating steps (a) through (c) using the recovered crystals from step (c) as the product of step (a).

7. The method of claim 4 wherein a ratio of ethyl acetate and hexane is about 1:99, by volume.

8. A method of preparing 1α-hydroxy-2-methylene-18,19-dinor-homopregnacalciferol crystals by diffusive exchange of solvents, comprising the steps of:
   (a) dissolving a product containing 1α-hydroxy-2-methylene-18,19-dinor-homopregnacalciferol in a first solvent comprising benzene;
   (b) providing a second solvent comprising hexane;
   (c) allowing said first solvent with dissolved product and said second solvent to diffuse together for a sufficient amount of time to form a precipitate of 1α-hydroxy-2-methylene-18,19-dinor-homopregnacalciferol crystals; and
   (d) recovering the 1α-hydroxy-2-methylene-18,19-dinor-homopregnacalciferol crystals.

9. The method of claim 8 wherein a ratio of benzene and hexane is about 13:87, by volume.

10. The method of claim 8 wherein the step of recovering comprises filtering to obtain the crystals.

11. The method of claim 8 wherein the step of allowing said first solvent with dissolved product and said second solvent to diffuse together takes place in a closed system purged with argon.

12. The method of claim 8 wherein the step of allowing said first solvent with dissolved product and said second solvent to diffuse together takes place at room temperature.

\* \* \* \* \*